(12) United States Patent
Maki et al.

(10) Patent No.: US 6,901,284 B1
(45) Date of Patent: May 31, 2005

(54) OPTICAL MEASURING INSTRUMENT

(75) Inventors: Atsushi Maki, Fuchu (JP); Tsuyoshi Yamamoto, Hatoyama (JP); Hideaki Koizumi, Tokyo (JP); Yuichi Yamashita, Kawagoe (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/913,323

(22) PCT Filed: Feb. 18, 2000

(86) PCT No.: PCT/JP00/00913

§ 371 (c)(1),
(2), (4) Date: Aug. 10, 2001

(87) PCT Pub. No.: WO00/49394

PCT Pub. Date: Aug. 24, 2000

(30) Foreign Application Priority Data

Feb. 19, 1999 (JP) .............................. 11-41820

(51) Int. Cl.[7] ................................. A61B 6/00
(52) U.S. Cl. ........................ 600/476; 600/473; 600/310
(58) Field of Search ................................ 600/310, 322, 600/473, 476, 477, 407; 356/338–343, 456–458, 39–42; 382/128, 131; 128/920, 922; 345/798, 799, 800

(56) References Cited

U.S. PATENT DOCUMENTS

| | | | | |
|---|---|---|---|---|
| 5,803,909 A | * | 9/1998 | Maki et al. | ................. 600/310 |
| 6,282,438 B1 | * | 8/2001 | Maki et al. | ................. 600/476 |
| 6,542,763 B1 | * | 4/2003 | Yamashita et al. | ........... 600/310 |
| 6,575,969 B1 | * | 6/2003 | Rittman et al. | ................ 606/41 |
| 2002/0091323 A1 | * | 7/2002 | Dreher | ....................... 600/476 |
| 2002/0183603 A1 | * | 12/2002 | Yamamoto et al. | .......... 600/323 |

OTHER PUBLICATIONS

"Near–Infrared Topographic Measurement System: Imaging of Absorbers Localized in a Scattering Medium", by Y. Yamashita et al, Instrum., vol. 67, pps. 730–732 (1996).
"Intracerebral Penetration of Infrared Light", by P. W. McCormic et al, Journal of Neuro–Surgery, vol. 76, pps. 315–318, (1992).
"Spatial and Temporal Analysis of Human Motor Activity Using Non–Invasive NIR Topography", by A. Maki et al, Medical Physics, vol. 22, pps. 1997–2005, (1995).

* cited by examiner

*Primary Examiner*—Eleni Mantis Mercader
(74) *Attorney, Agent, or Firm*—Antonelli, Terry, Stout & Kraus, LLP

(57) ABSTRACT

An optical measuring apparatus for optically measuring a sample includes a plurality of parts for applying light beams to the sample, a plurality of detecting parts for detecting light beams from the light applying parts which come through the sample, a memory part which receives signals from the detecting parts, converts them into digital signals and stores the digital signals as measuring positions between the light applying part and the light detecting part. Further, there is provided a first display part which shows a relationship between positions on the sample and measuring positions corresponding to the positions of the detecting parts on the sample, and a second display part which shows a relationship between positions on the sample and measuring positions corresponding to the positions of the detecting parts which are shown on the first display part.

10 Claims, 43 Drawing Sheets

FIG. 20

| | | |
|---|---|---|
| Edit Mark (Sub) | | |
| 1 ☑ 141 | ☑ 156 | |
| 2 ☑ 218 | ☑ 233 | |
| 3 ☑ 298 | ☑ 313 | |
| 4 ☑ 391 | ☑ 406 | |
| 5 ☑ 469 | ☑ 484 | |
| 6 ☑ 547 | ☑ 562 | |
| 7 ☑ 624 | ☑ 640 | |
| 8 ☑ 713 | ☑ 728 | |
| 9 ☑ 802 | ☑ 817 | |
| 10 ☐ | ☐ | |
| 11 ☐ | ☐ | |
| 12 ☐ | ☐ | |
| 13 ☐ | ☐ | |
| 14 ☐ | ☐ | |
| 15 ☐ | ☐ | |
| 16 ☐ | ☐ | |
| 17 ☐ | ☐ | |
| 18 ☐ | ☐ | |
| 19 ☐ | ☐ | |
| 20 ☐ | ☐ | |
| 21 ☐ | ☐ | |
| 22 ☐ | ☐ | |
| 23 ☐ | ☐ | |
| 24 ☐ | ☐ | |
| 25 ☐ | ☐ | |
| 26 ☐ | ☐ | |
| 27 ☐ | ☐ | |
| 28 ☐ | ☐ | |
| 29 ☐ | ☐ | |
| 30 ☐ | ☐ | |
| 31 ☐ | ☐ | |
| 32 ☐ | ☐ | |
| 33 ☐ | ☐ | |
| 34 ☐ | ☐ | |
| 35 ☐ | ☐ | |
| 36 ☐ | ☐ | |
| 37 ☐ | ☐ | |
| 38 ☐ | ☐ | |
| 39 ☐ | ☐ | |
| 40 ☐ | ☐ | |
| | | ☐ |
| | Reflect | ADD |

2001 — column 1
2002 — column 2
2003 — box
2004 — ADD
2005 — Reflect

OPTICAL MEASURING INSTRUMENT

FIELD OF THE INVENTION

The present invention relates to an optical measuring apparatus, and in particular, to an optical measuring apparatus which optically measures the inside of a living body, collects resulting information signals, and reconstructs the signals into images of the living body.

BACKGROUND OF THE INVENTION

The clinical and medical fields have longed for easy and simple technologies which measure insides of living bodies without giving any damage to them. An optical measurement is one of such technologies. The first reason for it is that the oxygen metabolism is related to specific chromatophores (hemoglobin, cytochrome a a3, myoglobin, etc.) or the concentration of light absorber and the concentration of the specific chromatophore can be obtained from the quantity of light absorption (between the visible ray and the near infrared ray). The second reason is that light rays can be easily handled by optical fibers. The third reason is that optical measurement is not harmful to living bodies when light rays are used correctly according to the Safety Standards (ANSIZ 136-1973 and JISC6802: 2 milliwatt per square millimeter).

An apparatus using such merits of the optical measurement and measuring the inside of a living body which applies light beams of visible wavelengths to near infrared wavelengths to a living body and collects the reflected light at a position 10 mm to 50 mm away from the illuminated position was disclosed for example by Japanese Non-examined Patent Publications No.63-277038 (1988) and No.H-5300887. Another apparatus which measures CT images of oxygen metabolism from light rays passing through a living body of 100 mm to 200 mm thick, or an optical CT apparatus was disclosed for example by Japanese Non-examined Patent Publications No.60-72542 (1985) and No.62-231625.

In application of the optical measurement which measures the characteristics due to living bodies to clinical fields, for example in measurement of a head, we can get the activation status of oxygen metabolism of a brain and local hemorrhage (breeding) in the brain. It is also possible to measure functions related to cerebral oxygen metabolism such as exercising, sensing, and further higher cerebral functions (e.g. thinking). In such measurements, images are much more powerful in analysis than data of measurement. For example, measurement and display using images are preferable for detection of positions which have a local oxygen metabolism change.

A multi-channel optical measuring apparatus is required to collect images. A multi-channel optical measuring system is disclosed by Japanese Non-examined Patent Publication H9-98972 (1997). However, it is substantially very important that we can check whether every channel of the system is normal before starting the multi-channel measurement.

An object of the present invention is to provide a multi-channel optical measuring apparatus which optically measures samples without causing any channel problem, processes information obtained by the measurement, and displays the selected items as images.

SUMMARY OF THE INVENTION

The optical measuring apparatus in accordance with the present invention which comprises means for optically measuring samples is characterized by further comprising a display unit which displays an area for selecting a measuring mode, an area for displaying positions of measurement, a measurement starting button, an area for displaying the result of measurement at the positions of measurement, and a button for saving the result of measurement.

From another point of view, the optical measuring apparatus in accordance with the present invention which comprises means for optically measuring samples is characterized by further comprising a display unit which displays an area for selecting an analysis mode, a button for loading a data file which is already registered, an area for setting a method of processing data, an area for editing and displaying images, and a button for saving the edited images.

From yet a further point of view, the optical measuring apparatus in accordance with the present invention which comprises means for optically measuring samples is characterized by further comprising a display unit which displays an area for selecting a display mode, a button for loading a data file which is already registered, an area for selecting a graph for display, and an area for displaying the selected graph.

From a more particular point of view, the optical measuring apparatus in accordance with the present invention which comprises means for optically measuring samples is characterized by further comprising a display unit which displays baselines (e.g., fitting graphs) corresponding to the positions of measurement on an identical screen.

BRIEF DESCRIPTION OF THE DRAWINGS

FIG. 11 is a graphical example representing how a relationship between a measurement signal obtained at a selected position of detection and an estimated no-load signal calculated from said measurement signal varies as the time goes by.

FIG. 12 is a graphical example representing how the concentration of oxidation/reduction hemoglobin at a selected position of measurement varies as the time goes by.

FIG. 20 is a subsidiary mark edition widow displayed on the display unit.

DETAILED DESCRIPTION OF THE PREFERRED EMBODIMENT

Figure 1:
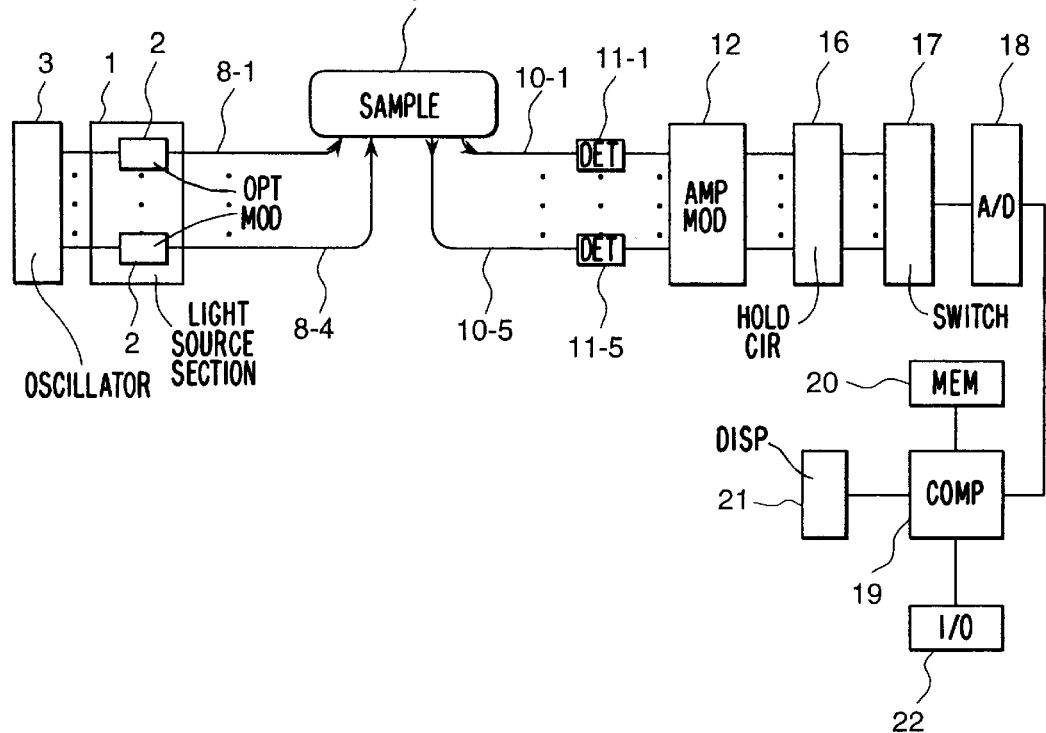
FIG. 1 is a block diagram of a main part of an optical measuring apparatus which is an embodiment of the present invention.

FIG. 1 shows a block diagram of a main part of an optical measuring apparatus which is an embodiment of the present invention. This embodiment applies light beams to a sample for example a brain skin, detects lights reflected in the sample and lights passing through the sample, and generates images of the inside of the cerebrum. This embodiment uses 12 channels of measurement (or 12 positions of measurement) and 24 measurement signals (or 24 analog/digital conversion channels). Naturally, the present invention is not intended to be limited to heads. The present invention can be applied to living bodies and the others.

The light source section 1 consists of four optical modules 2. Each optical module comprises two semiconductor lasers which respectively emit a plurality of wavelengths, for examples, 780 nm and 830 nm in a range of "visible" to "infrared" wavelengths.

It is to be understood that the invention is not intended to be limited to 780 nm and 830 nm and to two wavelengths. Said light source section 1 can use light emitting diodes instead of semiconductor lasers. The light beams from these eight semiconductor lasers in the light source section are respectively modulated by the oscillator section 3 which comprises eight oscillators having different oscillation frequencies.

Figure 8:
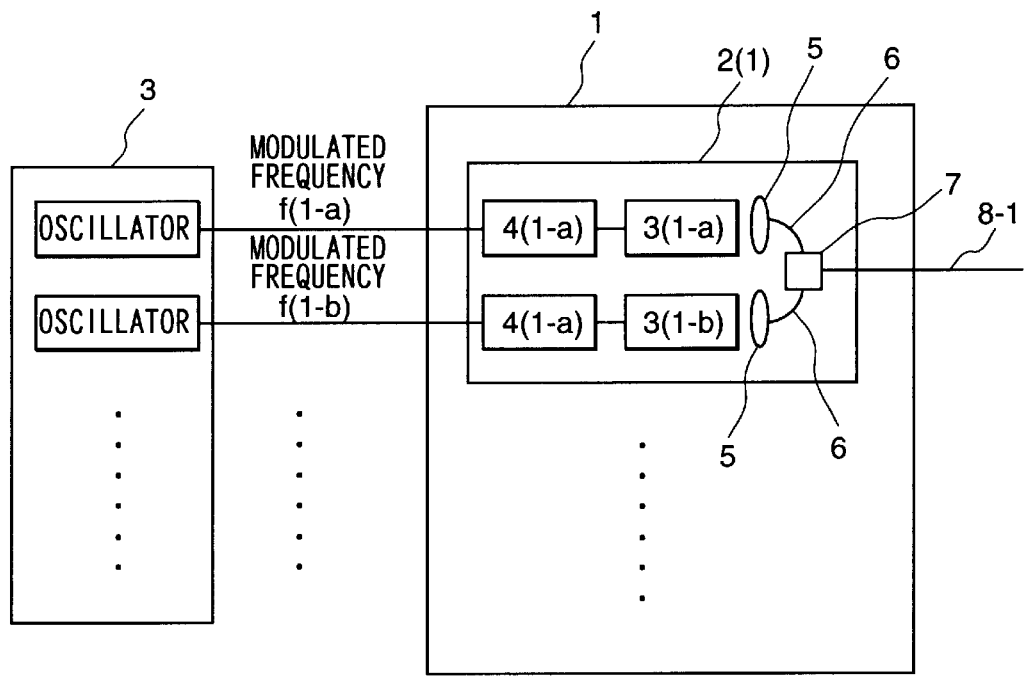
FIG. 8 is a block diagram of an optical module, as shown in FIG. 1.

FIG. 8 shows the internal configuration of the optical module with optical module 2(1) as an example. The optical module 2(1) contains semiconductor lasers 3(1-a) and 3(1-b) and their driving circuits 4(1-a) and 4(1-b). A numeric character in the parentheses indicates a module number of an optical module which includes the semiconductor laser and the driving circuit. Alphabetic characters "a" and "b" in the parentheses respectively indicate wavelengths 780 nm and 830 nm. These semiconductor laser driving circuits 4(1-a) and 4(1-b) feed direct-current bias currents to the semiconductor lasers 3(1-a) and 3(1-b). The oscillator 3 applies signals of different frequencies f(1-a) and f(1-b) respectively to the semiconductor lasers 3(1-a) and 3(1-b). These bias currents and signals cause the semiconductor lasers 3(1-a) and 3(1-b) to modulate the light beams emitted therefrom. Although this embodiment employs analog modulation by sine waves, the present invention can use a digital modulation by square waves of different time intervals, that is a digital modulation which flashes light at different time intervals. Such modulated light beams are respectively fed to optical fibers 6 by condenser lenses 5 placed one-to-one before the semiconductor lasers. The light beams of two different waveforms fed to each optical fiber are coupled into one optical fiber, for example into an irradiating optical fiber 8-1 by an optical fiber coupler 7 provided for each optical module. The light beams of two different wavelengths from each optical module are applied to four different positions on the surface of the sample 9 through the irradiating optical fibers 8-1 to 8-4.

The light beams which are reflected inside the sample and pass through the sample are collected by five detecting optical fibers 10-1 to 10-5 provided on the preset positions of detection on the surface of the sample and detected by photodiodes 11-1 to 11-5 connected to the detecting optical fibers 10-1 to 10-5.

The free end of each optical fiber is in slight contact with the surface of the sample 9. For example as disclosed by Japanese Non-examined Patent Publications H09-149903 (1997), these optical fibers are assembled into a probe to be applied to a sample.

Figure 9:
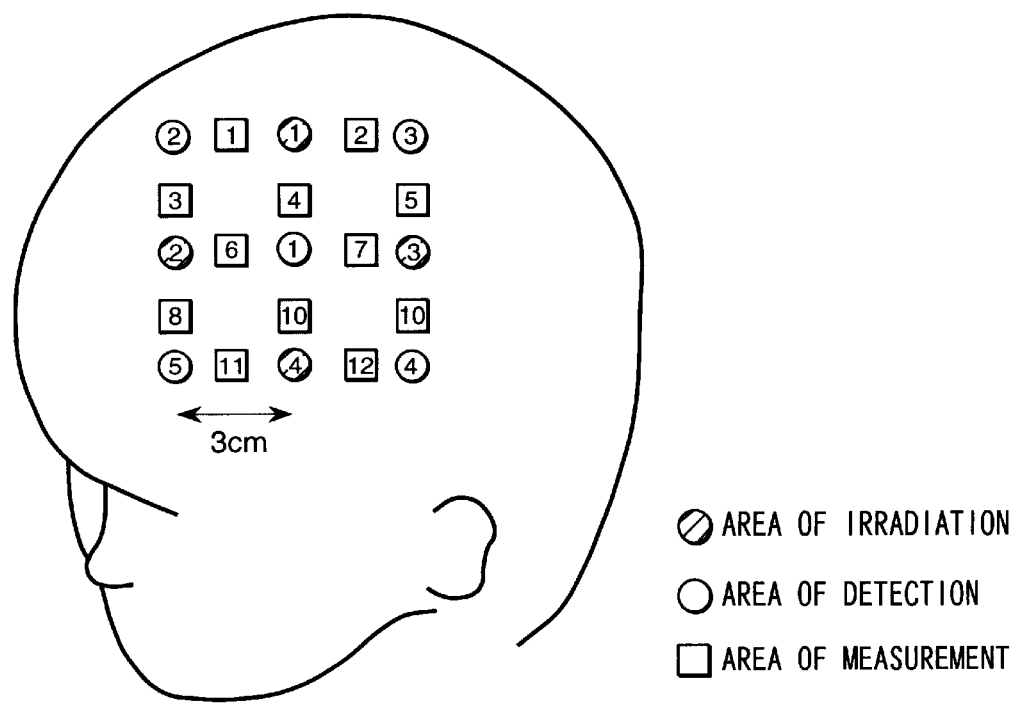
FIG. 9 is an example of a geometrical layout of positions of irradiation and positions of detection on the surface of a sample.

FIG. 9 shows a geometrical layout of positions of irradiation 1 to 4 and positions of detection 1 to 5 on the surface of the sample 9. In this embodiment, these positions are alternately disposed in a square array. A position of measurement is placed between every two irradiating and detecting positions which are adjoining to each other. There are 12 positions of measurement, or channels as there are 12 ways of selecting two positions from a group of irradiating and detecting positions. The layout of these radiating and detecting positions is described for example by Japanese Non-examined Patent Publications H09-149903 (1997) and by "Near-infrared Topographic Measurement System: Imaging of absorbers localized in a scattering medium" written by Yuichi Yamashita, et al. 1996, Review of Scientific Instruments Vol. 67, P. 730–P. 732. When the irradiating and detecting positions are spaced at intervals of 3 cm, the light beams detected at the detecting positions contain cerebral information as they pass through the skin and skull, which has been reported by "Intracerebral Penetration of Infrared Light" written by P. W. McCormic, et al. 1992, Journal of Neuro-Surgery Volume 76, P. 315–P. 318.

As seen from the above, 12 channels of measurement by this layout of positions enable measurement of a cerebral area of 6 centimeters square. Although this embodiment uses 12 measuring channels for simple explanation, it is possible to use more measuring channels and widen the area of measurement by providing more irradiating and detecting positions in an array.

In FIG. 1, the light beams detected by the optical fibers 10-1 to 10-5 are further detected respectively by five photo detectors such as photodiodes 11-1 to 11-5 which are one-to-one connected to the optical fibers 10-1 to 10-5. These photodiodes are preferably the avalanche photodiodes which enable high-sensitivity optical measurement. The photo detectors can be photoelectric multipliers. After the light signals are converted into electric signals by these photodiodes, the modulated signals are selectively detected according to the irradiating positions and wavelengths by a circuit which selectively detects modulated signals, for example a lock-in amplifier module 12 comprising a plurality of lock-in amplifiers. Although this embodiment uses a lock-in amplifier as a modulated signal detecting circuit for analog modulation, this embodiment uses a digital filter or digital signal processor to detect modulated signals for digital modulation.

Figure 10:
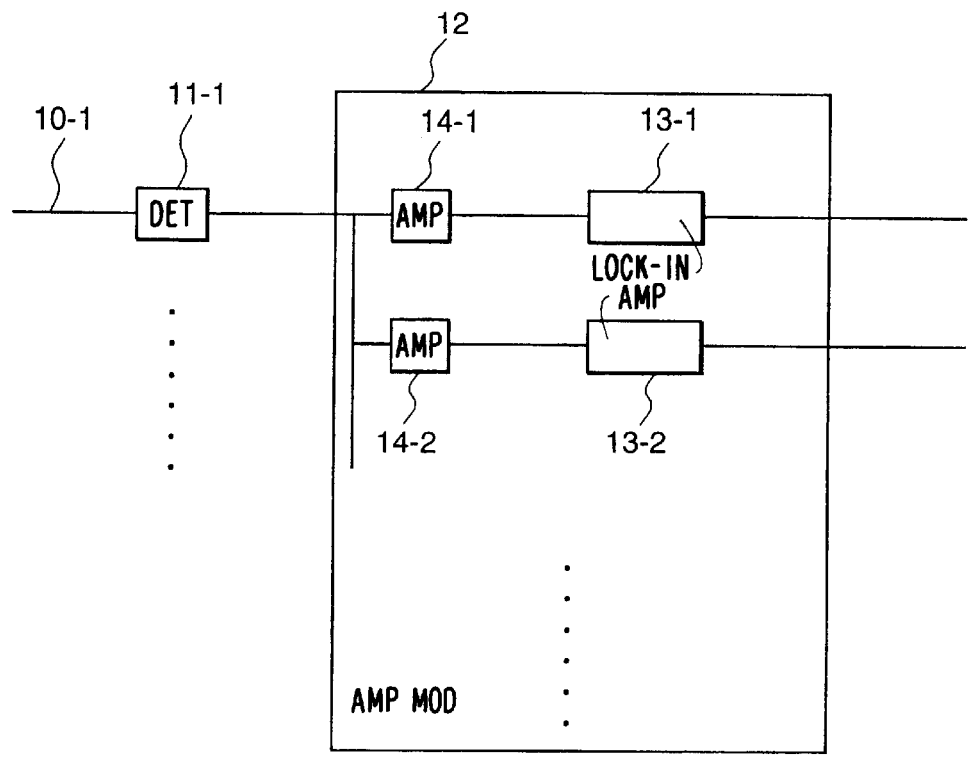
FIG. 10 is a block diagram of a lock-in amplifier module, as shown in FIG. 1.

FIG. 10 shows the configuration of the clock-in amplifier module 12 as shown in FIG. 1. First we explain modulation and separation of a signal detected at a detecting position 1 (in FIG. 9) by a photodiode 11-1. The detecting position 1 can detect light beams which are applied to the adjoining positions of irradiation 1 to 4. Therefore measurement is done at measuring positions 4, 6, 7 and 9. The light detected at the detecting position 1 by the photodiode 11-1 contains eight signal components whose modulation frequencies are f(1-a), f(1-b), f(2-a), f(2-b), f(3-a), f(3-b), f(4-a) and f(4-b) for light beams (two wavelengths each) applied to the irradiating positions 1 to 4. The light signals containing these eight signal components are fed to eight lock-in amplifiers 13-1 to 13-8 via eight amplifiers 14-1 to 14-8. The modulation frequency signals f(1-a), f(1-b), f(2-a), f(2-b), f(3-a), f(3-b), f(4-a) and f(4-b) are respectively given as reference signals to eight lock-in amplifiers 13-1 to 13-8. Therefore, the light signal components 780 nm and 830 nm applied to the irradiating position 1 are selectively separated and detected by the lock-in amplifiers 13-1 and 13-2. Similarly, the light signal components 780 nm and 830 nm applied to the irradiating position 2, the light signal components 780 nm and 830 nm applied to the irradiating position 3, and the light signal components 780 nm and 830 nm applied to the irradiating position 3 are selectively separated and detected by the lock-in amplifiers 13-3 and 13-4, the lock-in amplifiers 13-5 and 13-6, and the lock-in amplifiers 13-7 and 13-8 in that order Similarly, desired optical signal components are selectively separated from signals detected at the detecting positions 2, 3, 4, and 5 by photodiodes 11-2 to 1-5 and detected by the lock-in amplifiers. In other words, the optical signals detected at the detecting position 2 by the photodiode 11-2 are fed to four lock-in amplifiers 13-9 to 13-12 via four amplifiers 14-9 to 14-12. The optical signal components of 780 nm and 830 nm applied to the irradiating position 1 and the optical signal components of 780 nm and 830 nm applied to the irradiating position 2 are selectively separated and detected by the lock-in amplifiers. The optical signals detected at the detecting position 3 by the photodiode 11-3 are fed to four lock-in amplifiers 13-13 to 13-16 via four amplifiers 14-13 to 14-16. The optical signal components of 780 nm and 830 nm applied to the irradiating position 1 and the optical signal components of 780 nm and 830 nm applied to the irradiating position 3 are selectively separated and detected by the lock-in amplifiers. The optical signals detected at the detecting position 4 by the photodiode 11-4 are fed to four lock-in amplifiers 13-14 to 13-20 via four amplifiers 14-17 to 14-20. The optical signal components of 780 nm and 830 nm applied to the irradiating position 3 and the optical signal components of 780 nm and 830 nm applied to the irradiating position 4 are selectively separated and detected by the lock-in amplifiers. The optical signals detected at the detecting position 5 by the photodiode 11-5 are fed to four lock-in amplifiers 13-21 to 13-24 via four amplifiers 14-21 to 14-24. The optical signal components of 780 nm and 830 nm applied to the irradiating position 2 and the optical signal components of 780 nm and 830 nm applied to the irradiating position 4 are selectively separated and detected by the lock-in amplifiers.

As explained above, when two wavelengths and 12 measuring positions are used, there are 24 signals to be measured. Therefore, the lock-in amplifier module 12 uses a total of 24 lock-in amplifiers 13-1 to 13-24. The analog signals output from these lock-in amplifiers 13-1 to 13-24 (channel 1 to channel 24) are respectively summed up for a preset time period by channel-correspondent sample holding circuits in the sample holding circuit module 16. After the summation is completed, the signals stored in the sample holding circuits are sequentially switched by a switch (a multiplexer) 17, converted into digital signals, for example, by a 12-bit analog/digital (A/D) converter 18, and stored in a memory unit which is outside the computer 19. Naturally, these digital signals can be stored in a memory unit which is inside the computer 19. The channel numbers are one-to-one related to memory addresses.

In case the sample holding circuit module 16 is not used, the switch 17 is repeatedly switched fast. In this fast switching, the analog signal of each channel is converted into a digital signal by the analog/digital (A/D) converter 18, and stored in a memory unit 20. The digital signal of each channel which is summed up by a predetermined number of times is averaged by the computer 19 and stored in the memory unit 20. This method can also reduce noises in the high-frequency components.

The computer 19 calculates the stored data into a change in the concentration of oxygenating hemoglobin, a change in the concentration of deoxygenating hemoglobin, and a change in the concentration of all hemoglobins for example by a method disclosed by Japanese Non-examined Patent Publications H09-19408 (1997) and by "Spatial and Temporal Analysis of Human Moter Activity Using Noninvasive NIR Topography" written by Atsushi Maki, et al. 1995, Medical Physics Volume 22 P. 1997–P. 2005 and displays topographic images and the like on the display unit 20.

In FIG. 1, the computer 19 can be a personal computer. An operator section 22 is connected to the computer 19. The operator section 22 contains a keyboard, a mouse, and so on to input and output various information, add or delete data.

Figure 11:
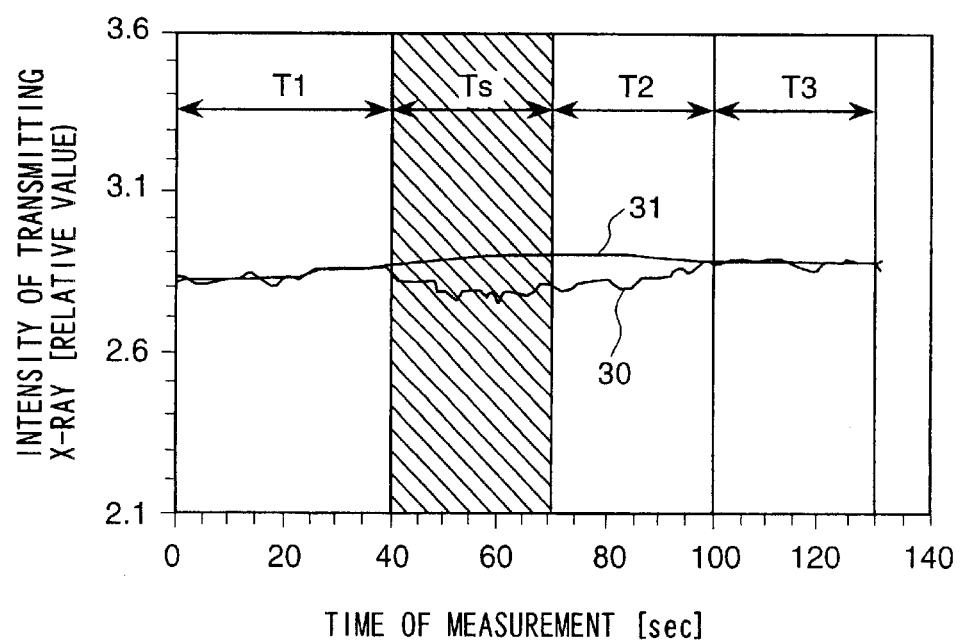

FIG. 11 is a graph representing how a measuring signal 30 at a detecting position and a non-load signal 31 estimated from said measuring signal change as the time goes by. This graph is displayed on the display unit 21. The horizontal axis (X-axis) of the graph represents a time of measurement and the vertical axis (Y axis) represents a relative change rate of the concentration of hemoglobin, that is, a change in the concentration of hemoglobin of a specific part in the brain due to the exercise of a specific function (e.g. moving part of living body such as fingers) of a living body. The estimated non-load signal 31 is obtained by fitting, by a method of least squares, an arbitrary function (base line) to a measuring signal 31 in a time period T1 before loading and a time period T3 after loading, excluding a signal in a loading time Ts during which a load is applied and a signal in a releasing time T2 elapsed for signal recovery from the measuring time 30. This embodiment uses a quadratic linear polynominal as the arbitrary function, T1 of 40 seconds, T2 of 30 seconds, and T3 of 30 seconds.

Figure 12:
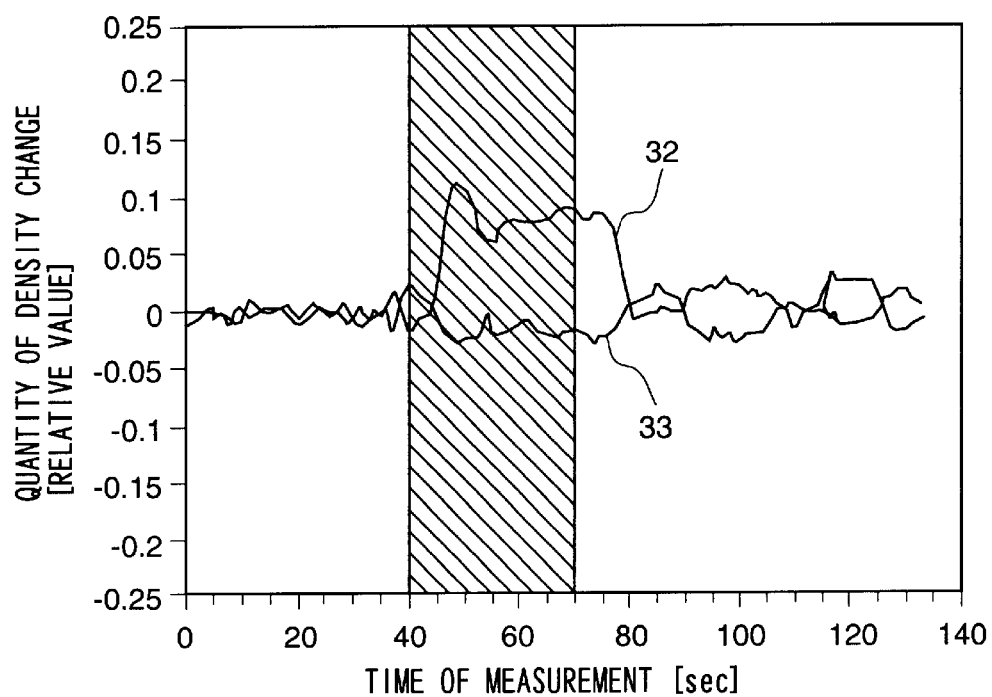

FIG. 12 is a graph representing how the relative concentrations of oxidizing and reducing hemoglobins change at a selected measuring position as the time goes by. This graph is displayed on the display unit 21. The relative concentration changes are given by lines 32 and 33. The horizontal axis (X-axis) represents a time of measurement and the vertical line (Y-axis) represents a relative concentration change. The hatched time period in the graph indicates a time period during which a load is applied (while right fingers are exercised). The relative change rates in FIG. 11 are computed from the non-load signal 31 and the expected non-load signal 32. The relative change rates in the concentrations of oxidizing and reducing hemoglobins (HbO2 and Hb) are computed by preset operations.

Figure 13:
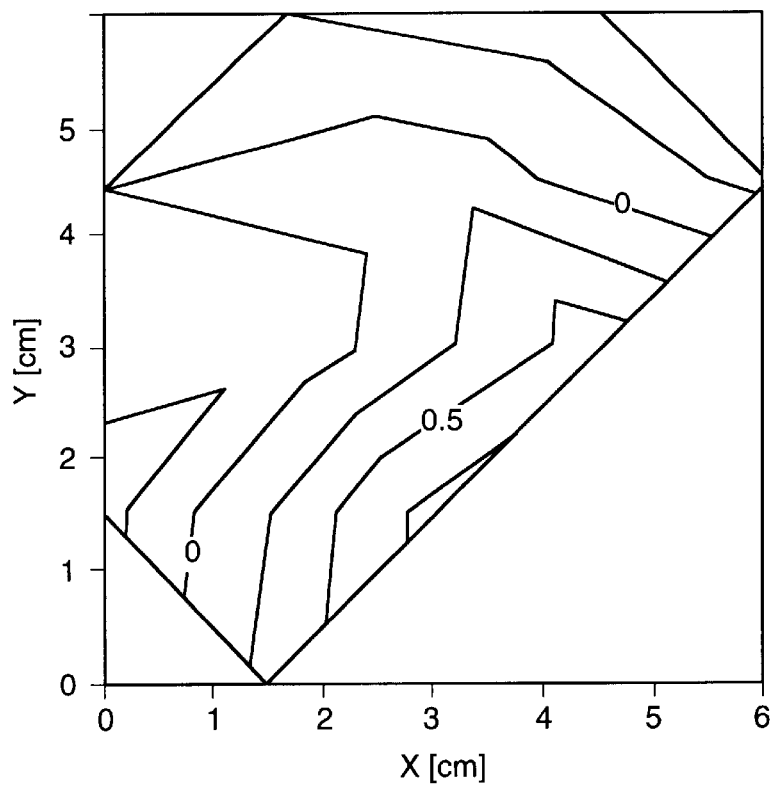
FIG. 13 is a contour image (topographic image) created from the relative change rate of the concentration of oxidation hemoglobin at each point of measurement according to a time lapse with the movement of the left hand of a tested person as a load.
Figure 14:
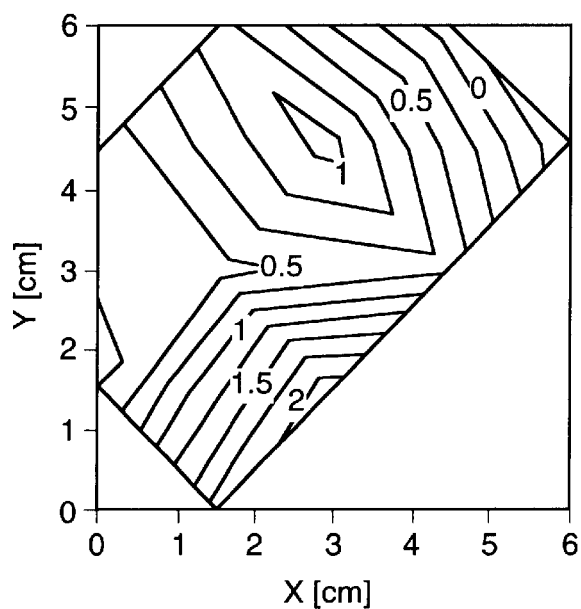
FIG. 14 is a contour image (topographic image) created from the relative change rate of the concentration of oxidation hemoglobin at each point of measurement according to a time lapse with the movement of the right hand of a tested person as a load.

FIG. 13 and FIG. 14 are contour images (topographic images) created from the relative change rates of the concentration of oxygenating hemoglobin at each measuring position relative to time, using the exercises of right and left fingers of the sample as the loads. Topographic images are created by integrating the relative change rate signal 32 with respect to time during a load time period (the hatched time period in FIG. 12) (or averaging the relative change rate signal 32 with respect to time) and linearly interpolating the intermediate values between every two adjoining measuring positions in the X- and Y-axes. The topographic images can be contour images, monochromatic contrast images or colored images. As seen from the images of FIG. 13 and FIG. 14 in comparison, it is apparent that the concentration of oxygenating hemoglobin at a specific position increases for the exercise of the right fingers. The visualization of information of such spatial distribution enables fast and easy recognition of the result of measurement.

Although the images of FIG. 13 and FIG. 14 are created by integrating the relative change rate with respect to time during a load time period, it is also possible to create topographic images from the relative change rate of the concentration of oxygenating hemoglobin at each measuring position for an identical measuring time period. We can visually obtain the relative change rate of the concentration of oxygenating hemoglobin with respect to time by displaying the created topographic images sequentially in the order of measurement or an animated or video sequence of the images.

Although the above description uses the relative change rate of the concentration of oxygenating hemoglobin as a typical example, we can also use the relative change rate of the concentration of deoxygenating hemoglobin or in the total concentration of oxygenating hemoglobin and deoxygenating hemoglobin to generate topographic images.

Figure 58:
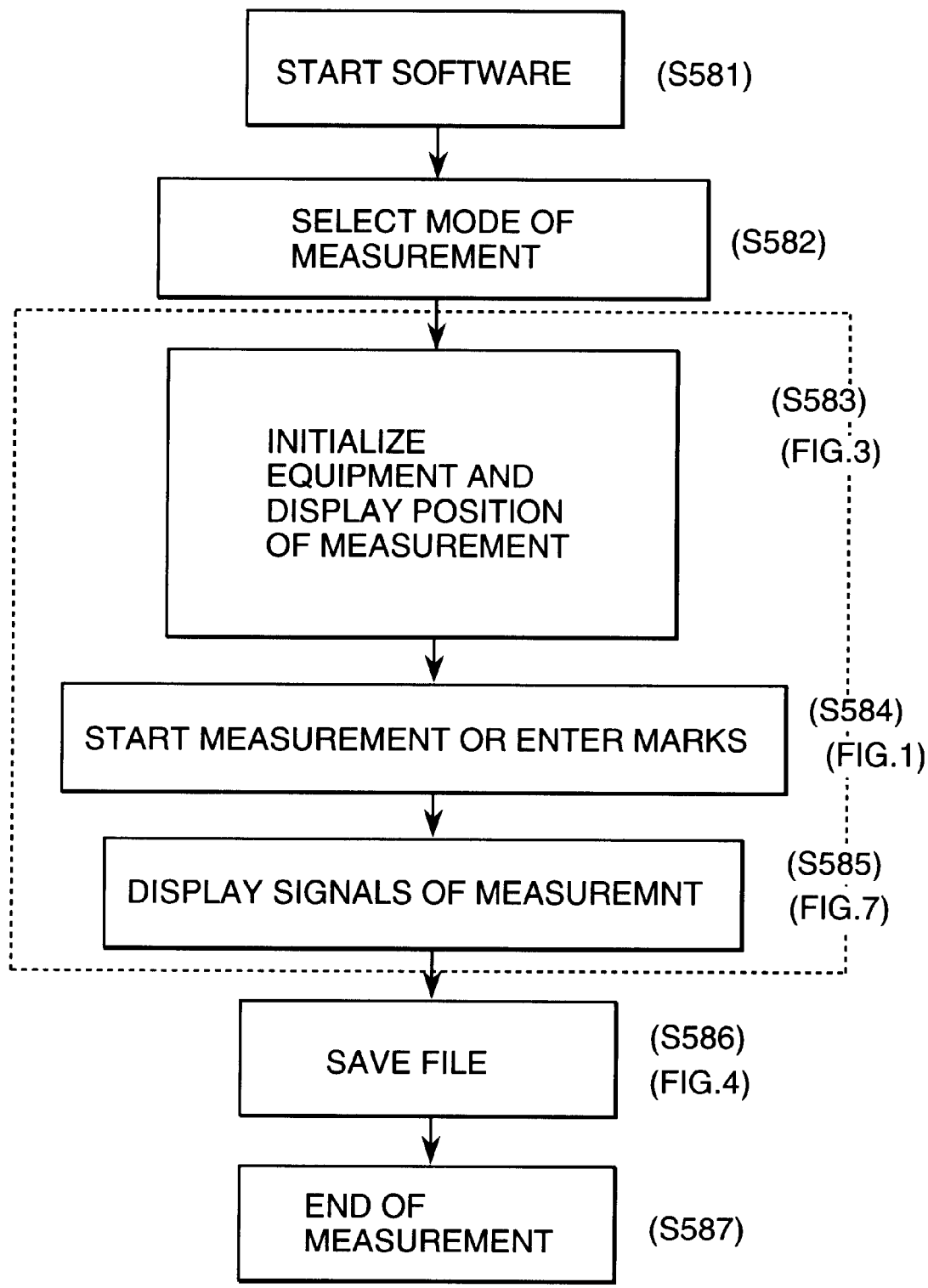
FIG. 58 is a flow of measurement of a sample by an optical measuring apparatus shown in FIG. 1, which is one embodiment of the present invention.

FIG. 58 shows a process flow for measuring a sample by an optical measuring apparatus of FIG. 1 which is an embodiment of the present invention. As seen from FIG. 58, this measurement flow loosely comprises the steps of starting up an optical measuring program at step S581, changing windows at steps S582 to S586, and ending measurement at step S587.

Figure 2:
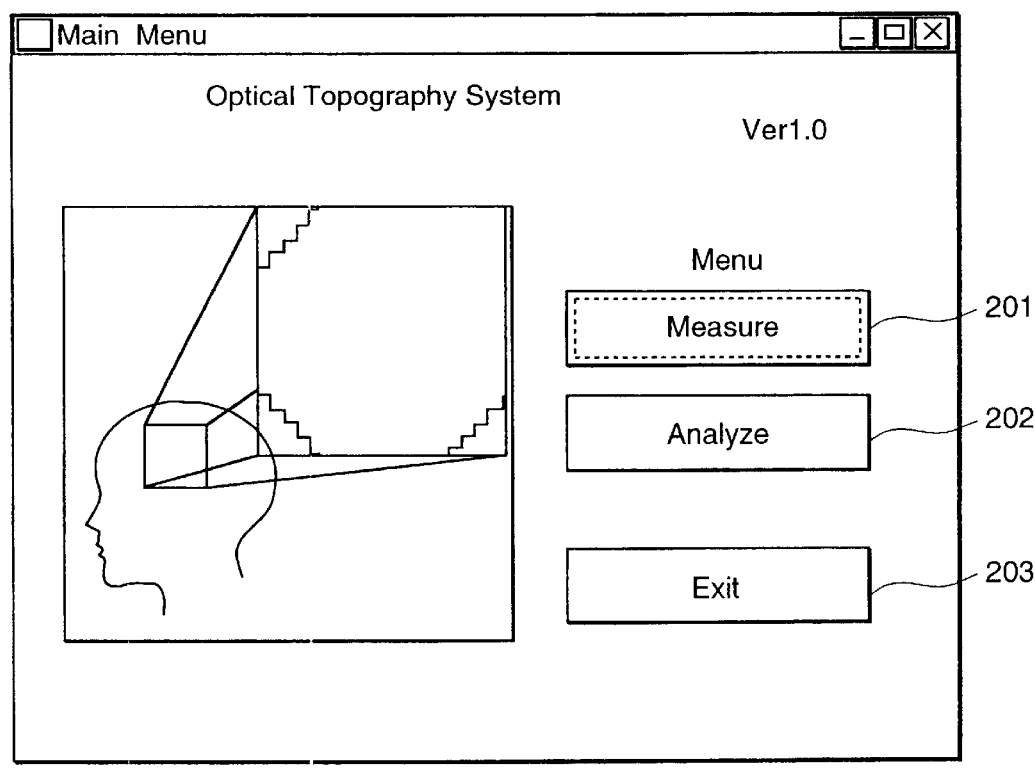
FIG. 2 is an initial window displayed on the screen of the display unit.
Figure 3:
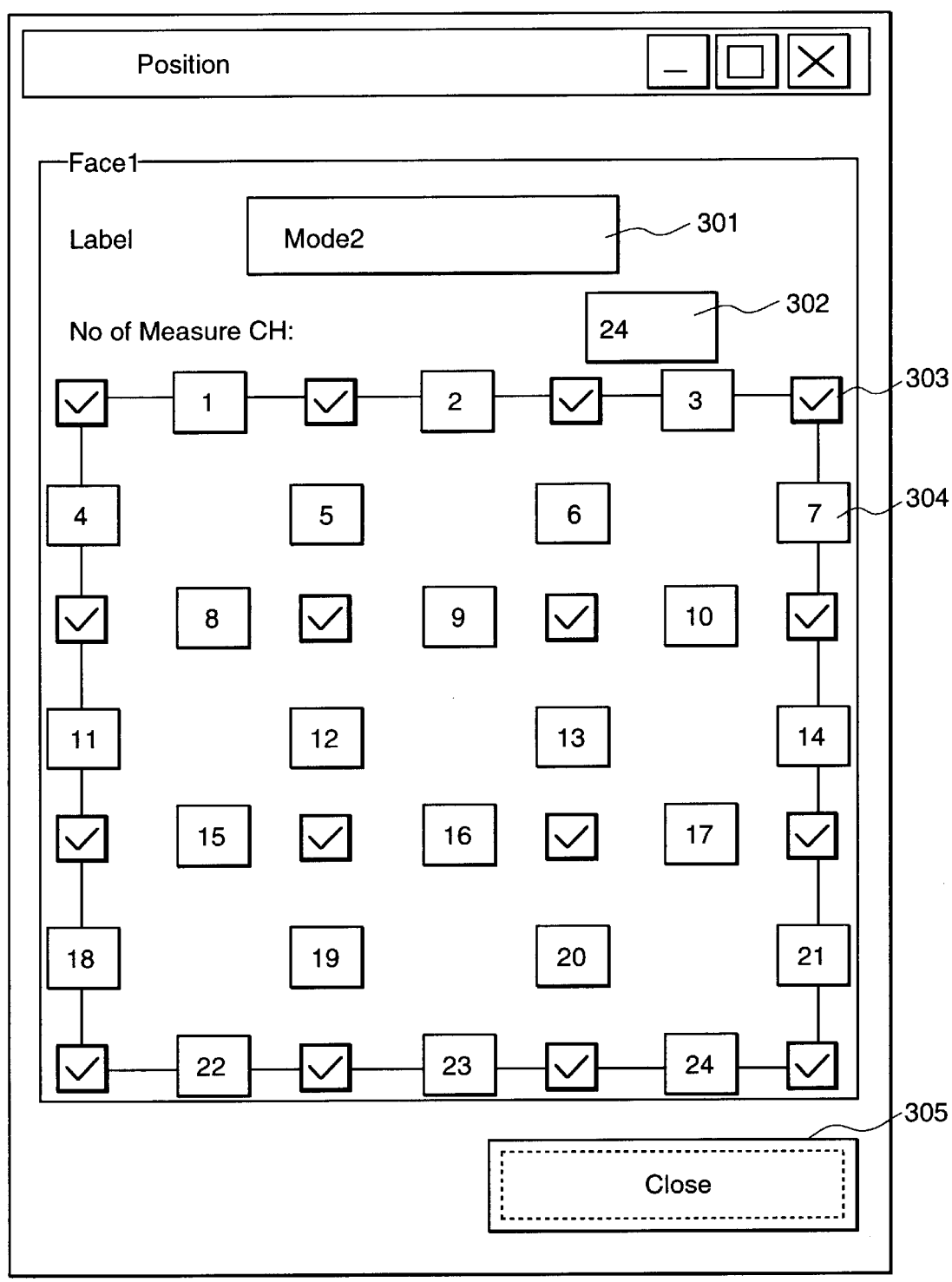
FIG. 3 is a window which displays positions of measurement on the display unit.
Figure 4:
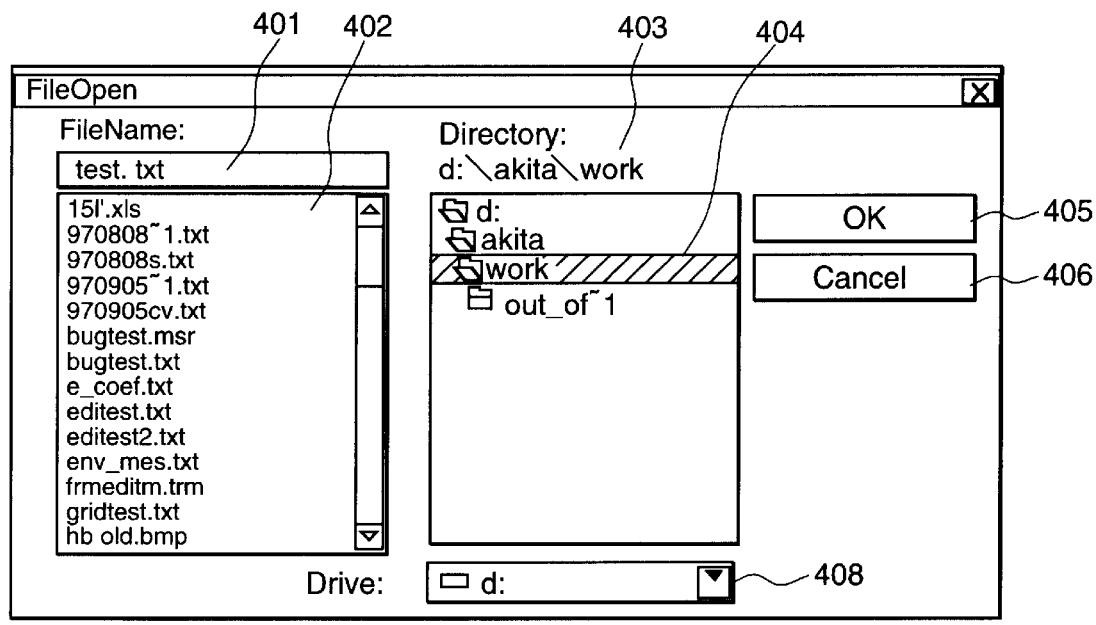
FIG. 4 is a dialog box for creating a file on the display unit.
Figure 7:
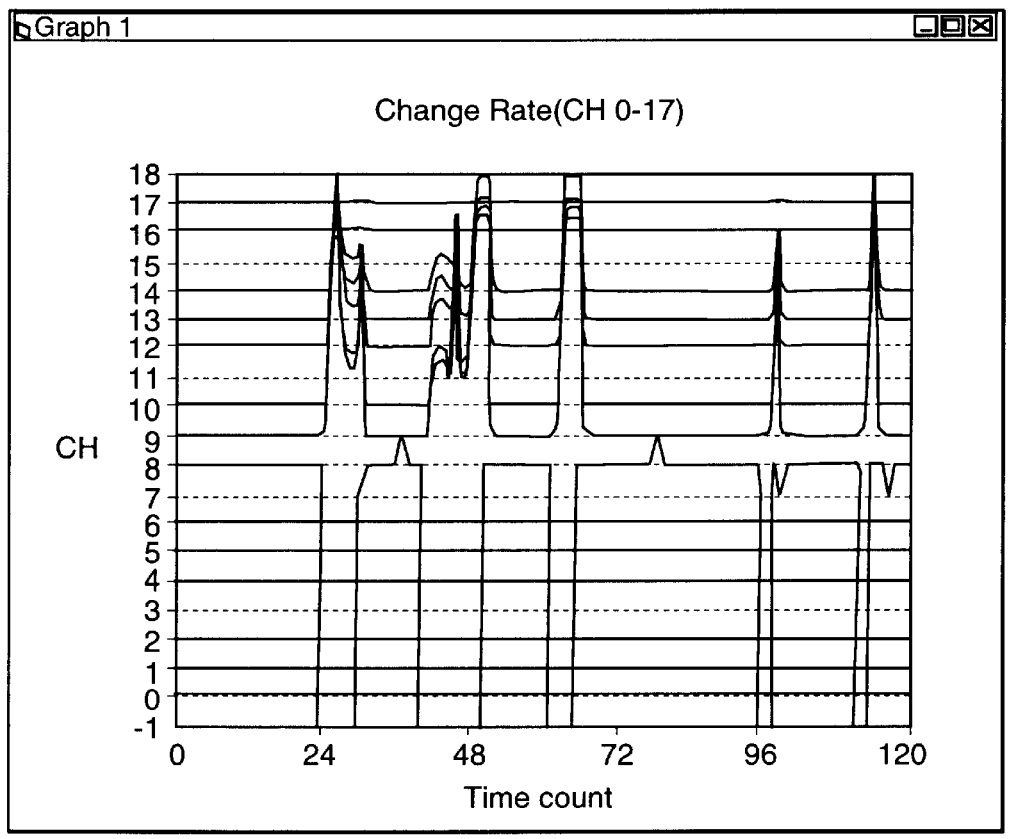
FIG. 7 is a window displaying a time-series graph of measurement data on the display unit.
Figure 5:
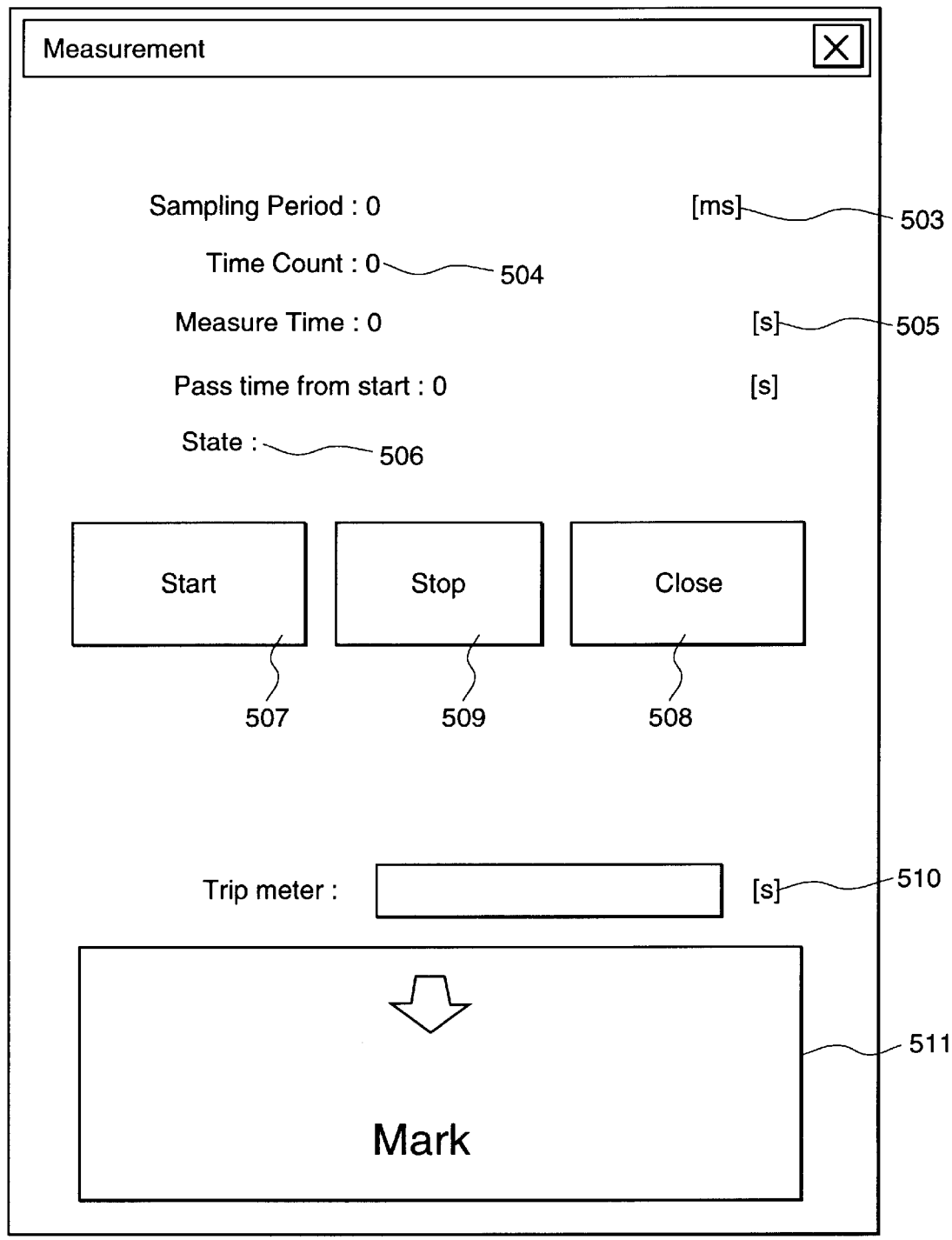
FIG. 5 is a window displaying items of measurement on the display unit.
Figure 59:
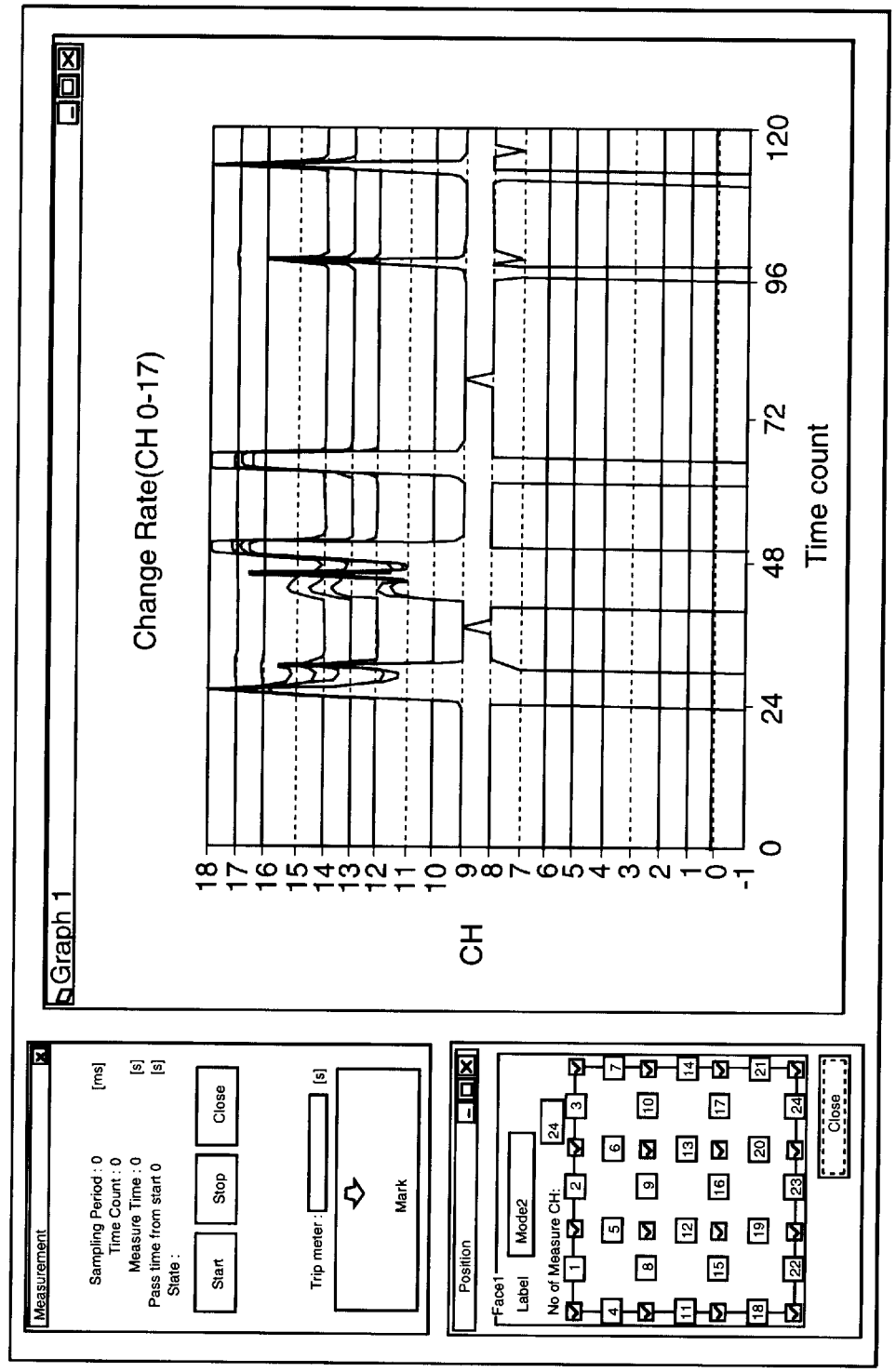
FIG. 59 is a window showing a graph of data of measurement in progress, which is displayed on the display unit.

The window appearing at step S582 in FIG. 58 is for selection of a measurement mode as shown in FIG. 2. The window appearing at step S583 is for initial apparatus setting and display of measuring positions with the measuring positions well-related to measuring signals, as shown in FIG. 3. The window appearing at step S584 is used to start measurement and enter marks (as shown in FIG. 5). The window appearing at step S585 shows the behavior of measuring signals (as shown in FIG. 7). The window appearing at step S586 is used to register, as a file, the signals measured at step S584, as shown in FIG. 4. Windows appearing at steps S583 to S585 are displayed at a time on the screen of the display unit as shown in FIG. 59.

When the operating system of the apparatus starts up, the initial window "Main Menu" (see FIG. 2) appears on-screen. In FIG. 2, the operator clicks button 201 to start measurement, button 202 to start data analysis, or button 203 to quit the program.

When the operator clicks button 201, a "Position" window (see FIG. 3) appears in the center of the screen. From now on, this window is basically always on a preset position of the screen of the display unit 21 in FIG. 1. At a glance of this "Position" window, the operator can see the relationship between measuring signals and actual measuring positions easily and quickly. Usually, the irradiating optical fibers 8-1 to 8-4 and the detecting optical fibers 10-1 to 10-5 in FIG. 1 are fixed to a helmet which is put on the head of an examinee. Accordingly, for the operator's convenience, the measuring channel numbers are marked on the helmet and the assignment of the channel numbers to measuring positions (see 304 in FIG. 3) is recorded in advance.

The box 301 in FIG. 3 displays a selected measurement mode. The position layout of the selected mode is displayed below the box 301. The box 302 displays the number of channels used for measurement of an area to be measured. The boxes 303 represent the alternate preset positions of irradiating and detecting optical fibers, that is, positions selected from a group of irradiating positions and detecting positions.

When the File Open window (see FIG. 4) appears on-screen, the position moves to the lower left part on the screen. With this, the operator can always watch a condition to be entered.

FIG. 4 contains the following items and functions:

401: A filename entry box

402: A pane showing a list of all files in a hierarchical level selected by a bar 404 in the right pane. For example, a name of data which was measured before is listed here.

403: Displays a current path.

404: Displays a directory list (a "tree" list)

405: Click this button to start a measurement.

406: Click this button to cancel the setting on this window and return to the window of FIG. 3.

408: Click this button to open a drop-down list of drives and select a drive.

When the operator clicks the button 405 in FIG. 4, the File Open window disappears and the Measurement window (see FIG. 5) appears on the upper left part of the screen. One or more graph windows (see FIG. 7) appear on the remaining right part of the screen. The Measurement window of FIG. 5 is used to control execution of the measurement. FIG. 5 contains the following items and functions:

503: A field displaying a specified data sampling time interval

504: A field displaying a number of data sampling times

505: A field displaying a time period of measurement (a time elapsed from the beginning of measurement)

506: A field displaying the status of measurement which is one of the following:

Run: Measurement in progress

Completion: Measurement is completed.

Overrun: Abnormal termination of measurement due to an overflow of the A/D converter Stop: Abnormal termination of measurement due to the other factor File error: An error in saving a measurement file Back up file error: An error in making a backup copy of a measurement file

507: A button to start measurement

When the operator clicks this button, the system starts measurement and displays graphs representing the relationship between measurement data and time as shown in FIG. 7. The graph of FIG. 7 shows change rates, but it can be source signals or concentrations of hemoglobin.

508: A button to end measurement and inspection

509: A button to stop acquisition of data

510: A field displaying a time period elapsed after the Mark button is clicked This frees the operator from counting a stimulation time by a stopwatch

511: A Mark button

This button is used to add a vertical line as a mark to the graph of FIG. 7 during measurement. Usually, this mark is added at the start or end of stimulation for reference in data analysis. It can be added when the operator wants to record times in the graph while measurement is in progress.

When the marks are automatically added to FIG. 7 from an external unit, the operator need not click the Mark button. In some cases, the marks are added together with beeps.

Figure 17:
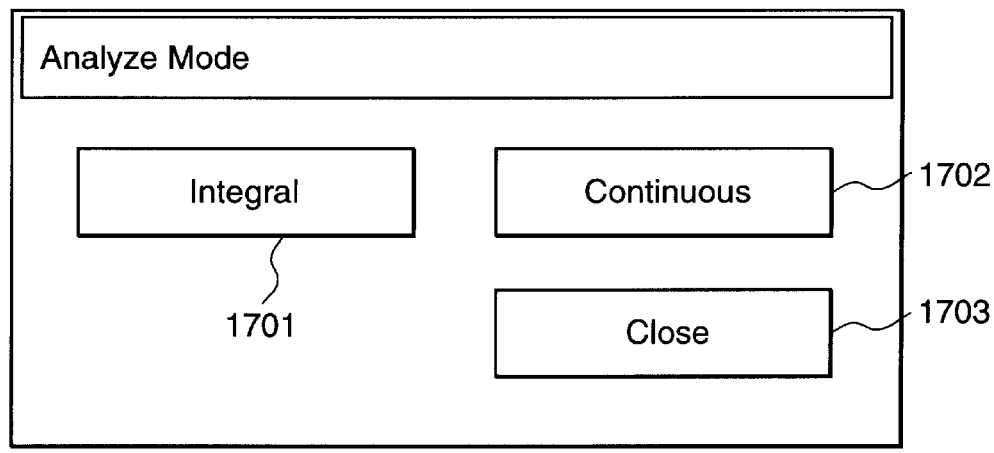
FIG. 17 is a dialog box for selecting an analysis mode for display
Figure 18:
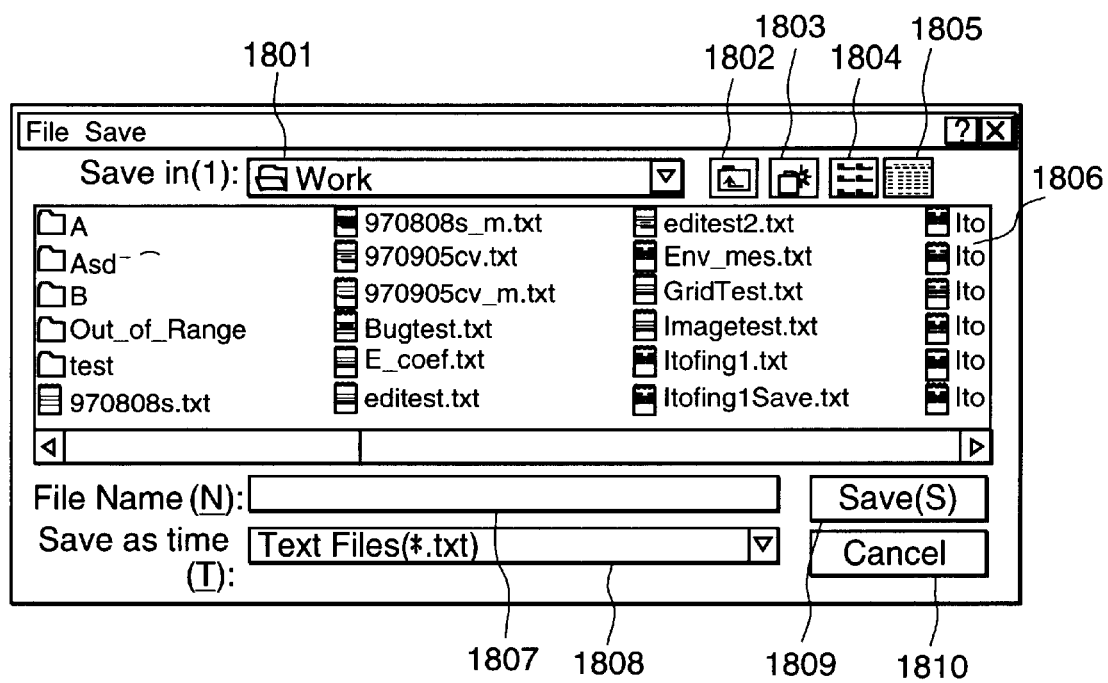
FIG. 18 is a dialog box for loading a file for display.
Figure 60:
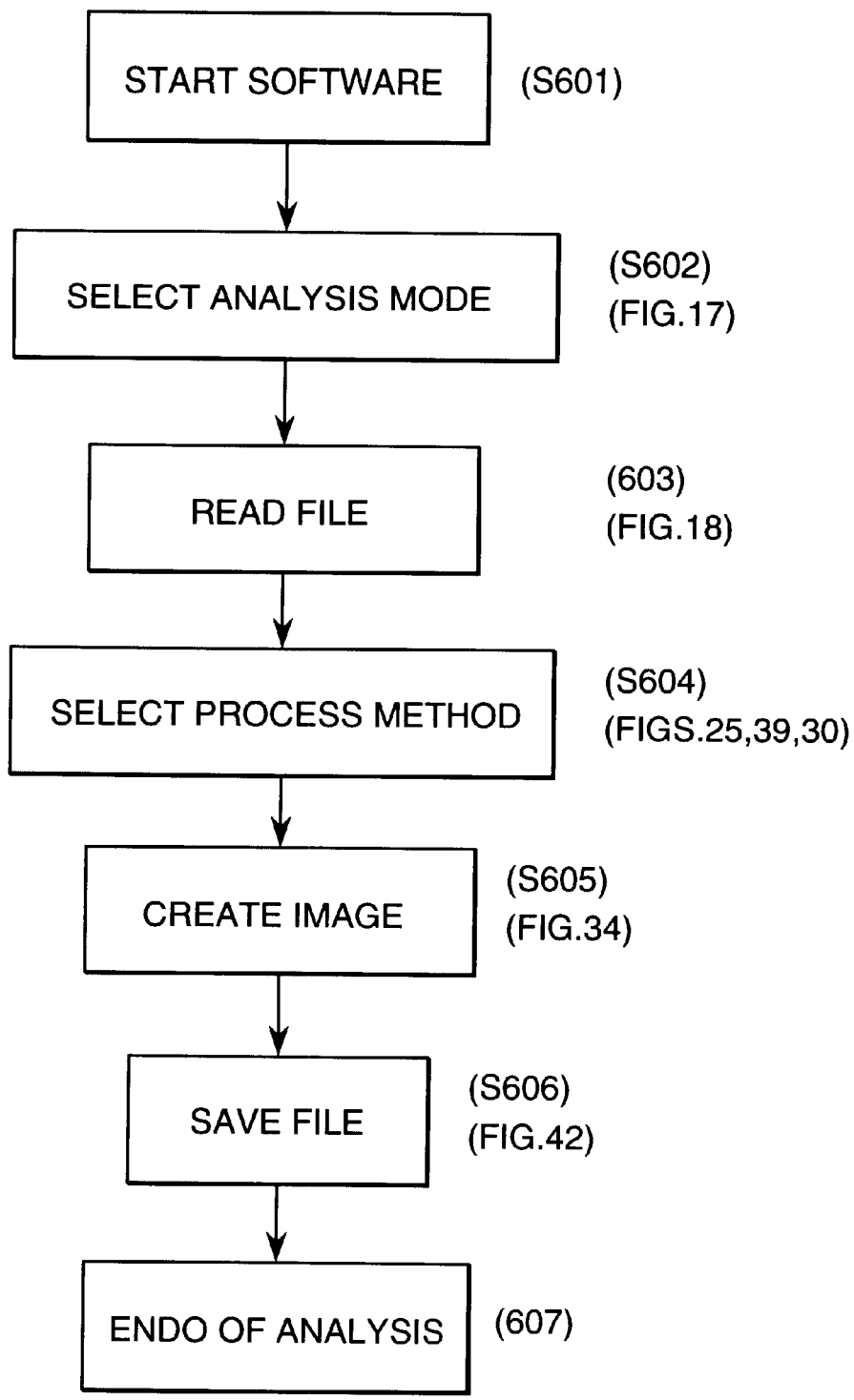
FIG. 60 is a sample process flow in accordance with the present invention which analyzes data obtained by the optical measuring apparatus shown in FIG. 1.

FIG. 60 shows a flow of data analysis (processing) after measurement by the optical measuring apparatus of FIG. 1, which is an embodiment of the present invention. The data analysis will be described in detail referring to FIG. 15 to FIG. 43. As seen from the data analysis flow of FIG. 60, the data analysis loosely comprises the steps of starting up an optical measuring program at step S601, changing windows at steps S602 to S606, and ending the data analysis at step S607. The window appearing at step S602 in FIG. 60 is for selection of a data analysis mode as shown in FIG. 17. The window appearing at step S603 is used to load a registered data file, as shown in FIG. 18. Windows appearing at step 604 are FIG. 25, FIG. 29, and FIG. 30 and used to set a method of data processing (arithmetic processing). The window appearing at step S605 is as shown in FIG. 34 and used to create a topographic image. The window appearing at step S606 is as shown in FIG. 42 and used to save the image as a file.

Figure 15:
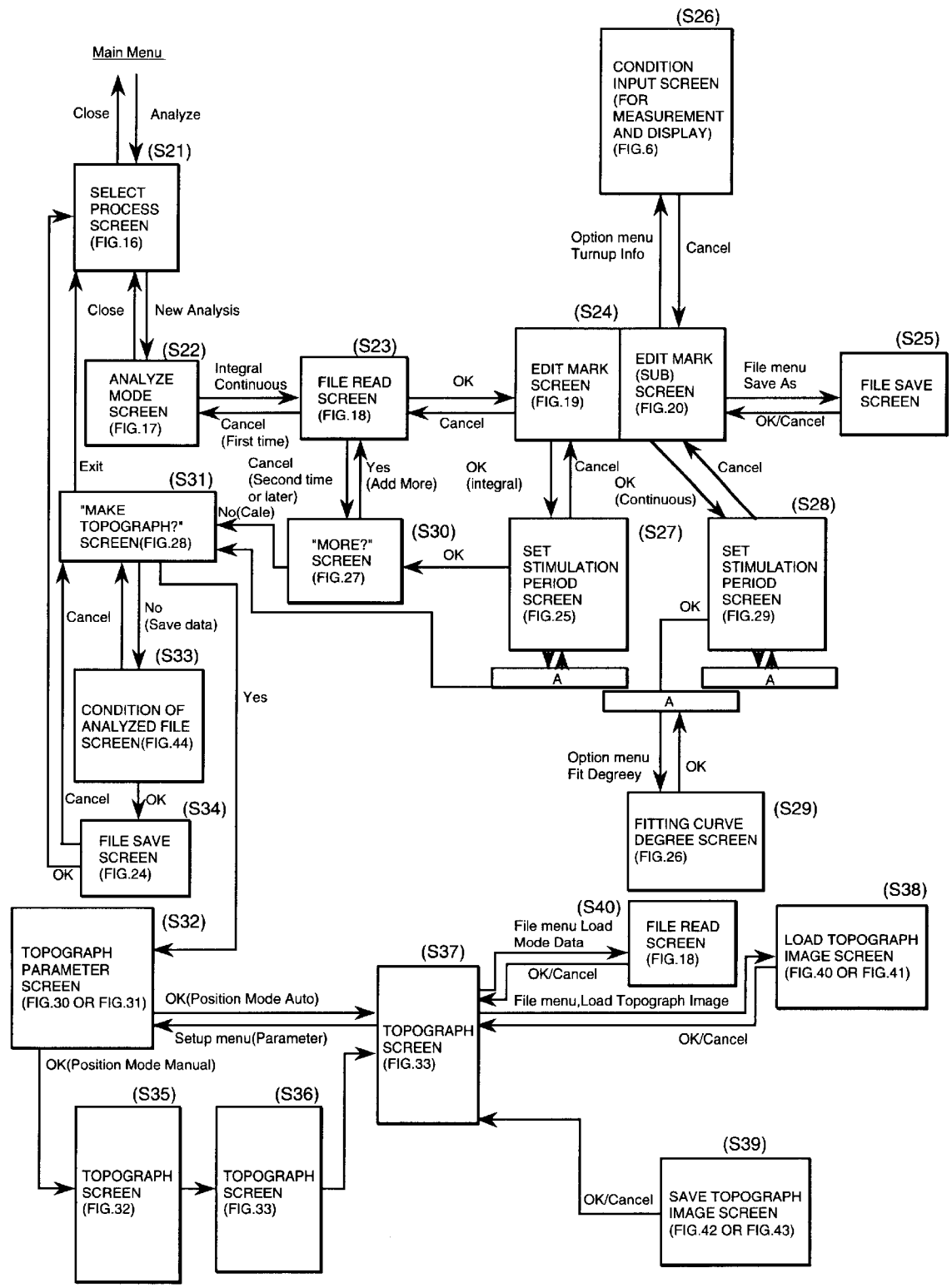
FIG. 15 is a sample process flow in accordance with the present invention which measures a sample and analyzes the resulting data by the optical measuring apparatus as shown in FIG. 1.

FIG. 15 shows a flow of data analysis (processing) after measurement by the optical measuring apparatus of FIG. 1, which is an embodiment of the present invention.

After the measurement is completed, the operator returns to the Main Menu window (see FIG. 2) and clicks the Analyze button 202, the system starts the data analysis step and displays the Select Process window (see FIG. 16) instead of the Main Menu window (see FIG. 2) (at S21). The Select Process window of FIG. 16 has the following items and functions:

1601: An option button to select creation of an image

1602: An option button to select a created or processed image and a graph display mode

1603: Click this button to start the selected process.

1604: Click this button to endl the setting on this window and return to the Main Menu window.

Figure 16:
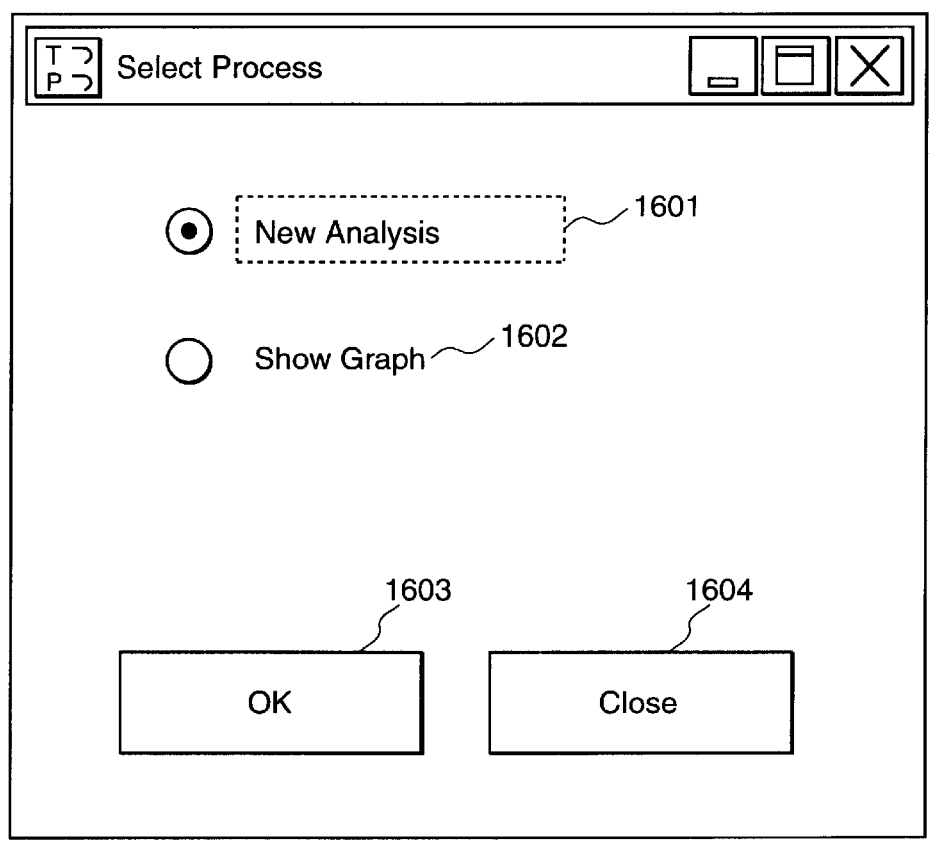
FIG. 16 is a dialog box for selecting a process for display.

When the operator clicks the OK button 1603 in FIG. 16, the Select Process window is replaced by the Analyze Mode window (see FIG. 17) (at S22). On the Analyze Mode window (see FIG. 17), the operator clicks the Integral button 1701 to go to the Summing Average Analyze mode, the Continuous button 1702 to the Non-Summing Average Analyze mode, or the Close button 1703 to return to the Select Process window. When the operator clicks the button 1701 or 1702, the Analyze Mode window is replaced by the File Load window (FIG. 18) (at S23). The File Load window of FIG. 18 has the following items and functions:

1801: A box to specify a folder (directory)

1802: A One-Up-Level button to go up to a folder on the one-up level in the "tree" structure

1803: A New Folder button to create a new folder

1804: A List button to display the contents of a specified directory

1805: A Details button to display the more details of a list displayed by the List button

1806: An area for displaying folders and files in the specified directory

1807: A box to enter a file name

This box automatically displays a file name which is selected in the list area 1806.

1808: A box to select a type of the file

The files of the type selected here are displayed in the list area 1806.

1809: A button to load a selected file and proceed

1810: A button to cancel the setting on this window and return to the window of FIG. 17.

When the operator clicks the Load button 1809, both the Edit Mark window (see FIG. 19) and the Edit Mark (Sub) window (see FIG. 20) appear on-screen (at S24). The Edit Mark window is placed in the right side of the Edit Mark (Sub) close to each other on the screen. The Edit Mark (Sub) window shows a listing of times or sampling counts of marks given on the Edit Mark window in the ascending order of mark values. The operator can delete marks on the Edit Mark window by clicking their check boxes on the Edit Mark (Sub) window to remove the check marks and clicking the Reflect button 2005. At the same time, their values on the Edit Mark (Sub) window disappear, too.

To add a mark to the graph on the Edit Mark window, the operator enters a time or sampling count of a mark to be added in the box 2003 and clicking the ADD button 2004. The specified mark appears in the graph on the Edit Mark window and its value also appears on the Edit Mark (Sub) window.

There is another way of editing marks; using a mouse line 1915 which is a line pointing to a position where the mouse pointer exists (and moves as the mouse moves on the window). The position (time and count) of the mouse line is given in the boxes 1904 and 1907 (to be explained later). To add a mark to the graph on the Edit Mark window, the operator drags the mouse line to a position on which the operator wants to put a mark and click the Add button 1909. The mark is added to the specified position in the graph on the Edit Mark window and its value is also displayed on the Edit Mark (Sub) window. When the mouse line 1915 is positioned on an existing mark, the Del button 1910 (to be explained later) becomes active (enabled). When the Del button 1910 is clicked, the mark disappears.

There is still another way of adding a mark. The operator enters the count of a mark that the operator wants to add in the box 1908 (to be explained later) and clicks the Add button 1909. The mark is added and the result is given to both the Edit Mark window and to the Edit Mark (Sub) window.

Figure 19:
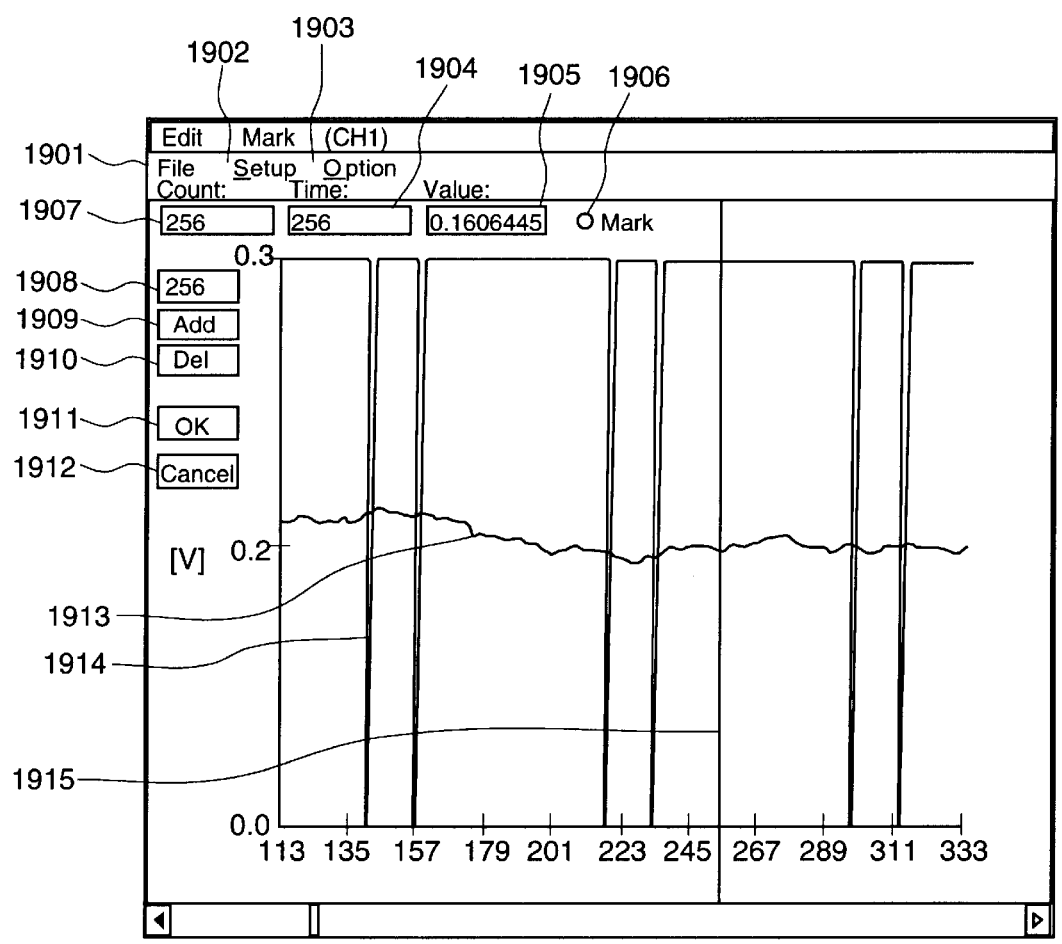
FIG. 19 is a mark edition widow displayed on the display unit.
Figure 21:
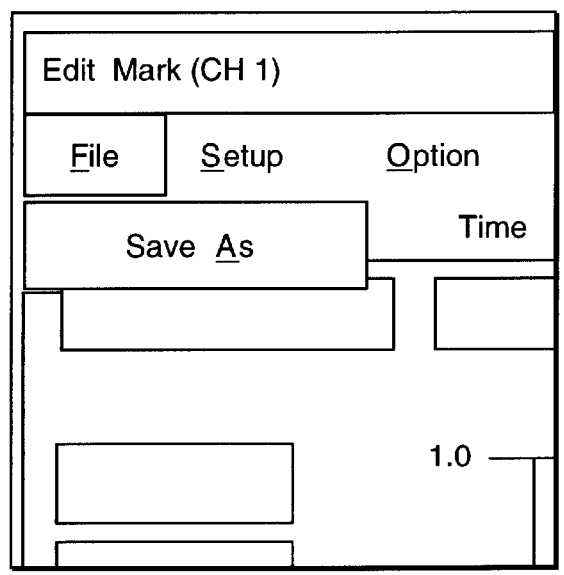
FIG. 21 is a File menu of the Edit Mark window as shown in FIG. 19 and FIG. 20.
Figure 22:
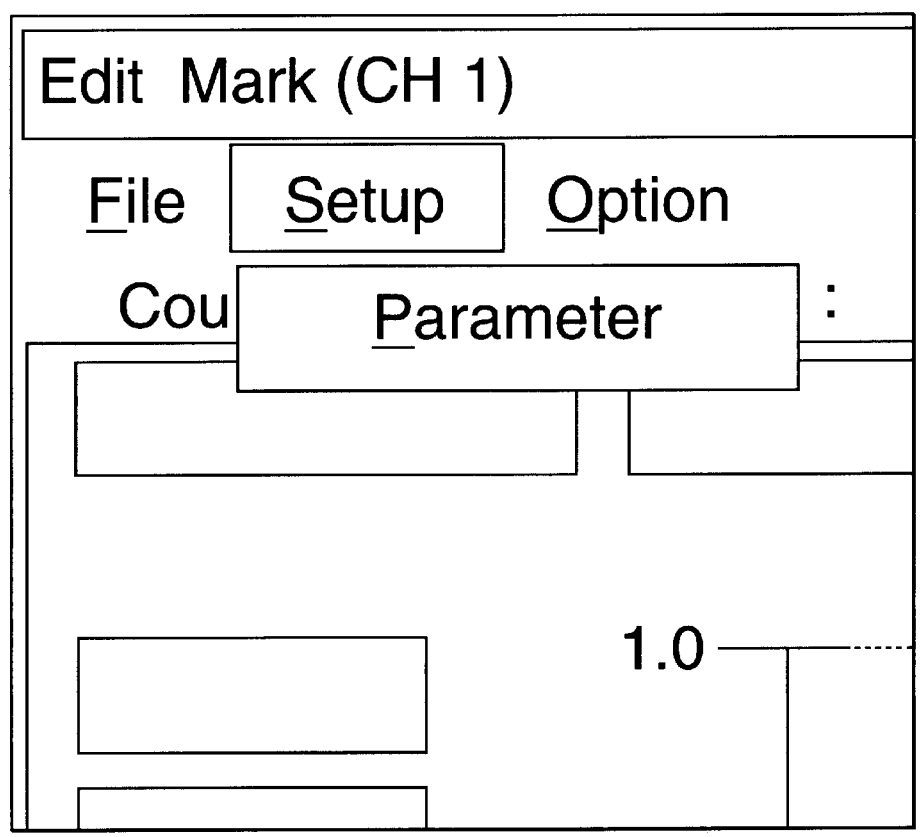
FIG. 22 is a Setup menu of the Edit Mark window as shown in FIG. 19 and FIG. 20.
Figure 23:
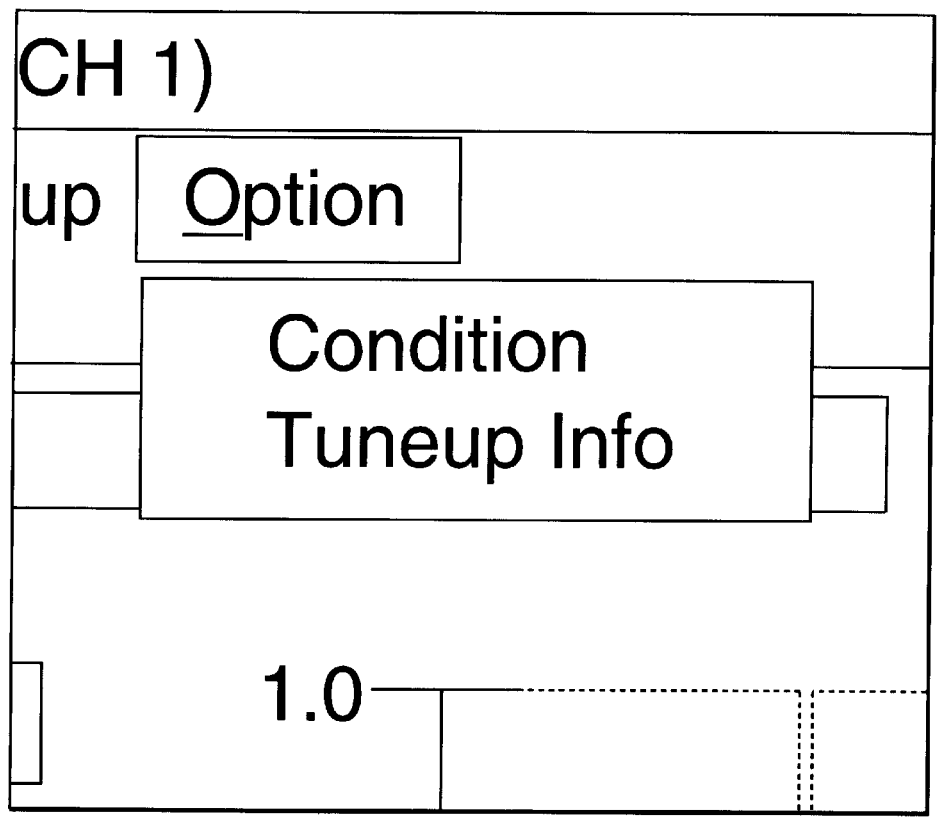
FIG. 23 is an option menu of the Edit Mark window as shown in FIG. 19 and FIG. 20.

Widows of FIG. 19 and FIG. 20 have the following items and functions:

1901: When this File button is clicked, a File menu (see FIG. 21) pops up. When the operator clicks "Save As" on this pop-up menu, the File Save window (see FIG. 24) appears. This window is used to save the result of data edition. In saving, the original data (before edition) is also saved with the extension of the file name changed to ".BAK." This prevents the original data from being lost.

1902: When this Setup button is clicked, a Setup menu (see FIG. 22) pops up. When the operator clicks "Parameter" on this pop-up menu, the graph display control window for mark edition appears. The operator can change magnifications of X- and Y-axes and time or count values of the X-axis on the Edit Mark window.

1903: When this Option button is clicked, an Option menu (see FIG. 23) pops up.

The Option menu contains selective items "Condition" and "Tuneup Info."

When the operator clicks "Tuneup Info" on this pop-up menu, the Tuneup window (see FIG. 6) appears to set measuring and display conditions. (When the Cancel button 615 is clicked on the Tuneup window, windows FIG. 19 and FIG. 20 return.)

1904: A field displaying a time on which the mouse line 1915 positions

1905: A field displaying a data value (a value on the Y-axis) corresponding to the mouse line 1915

1906: A check mark appears here when the mouse line 1915 positions on an existing mark.

1907: A field displaying a count at a position pointed to by the mouse line 1915

1908: An entry box for a count value of the mark position

1909: A button to add a mark to a position specified by a count value in the box 1908 or by the position of the mark line 1915

1910: A button to delete a mark

1911: A button to proceed to the next process

Figure 25:
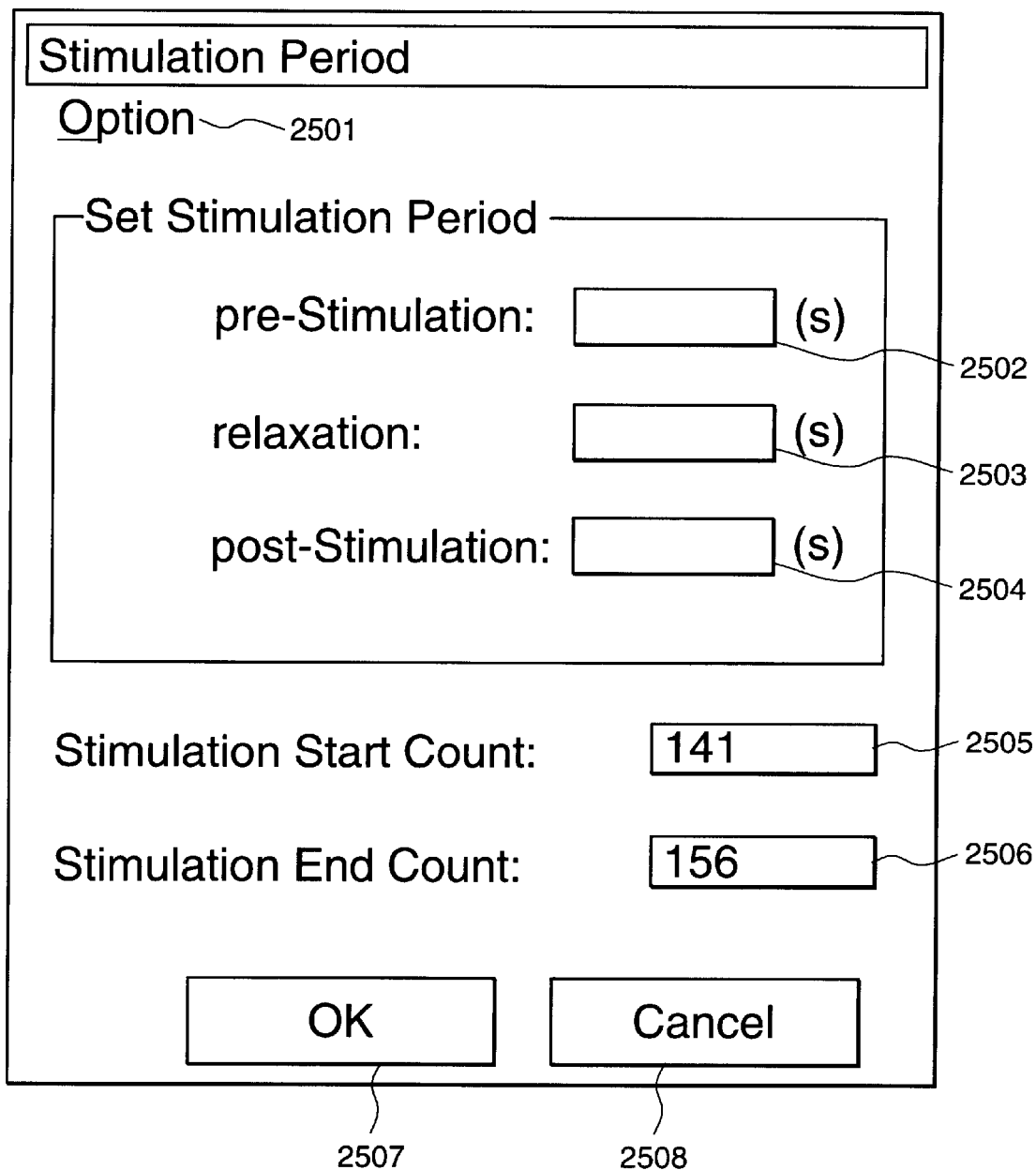
FIG. 25 is a dialog box for setting a stimulation period (process time for analysis of summing averages) displayed on the display unit.

When this button is clicked in the Summing Average Analysis mode, the Stimulation Period window (Process time definition window for summing average analysis) shown in FIG. 25 appears on screen. When this button is clicked in the Non-Summing Average Analysis mode, the Stimulation Period window shown in FIG. 29 appears on screen.

1912: A button to cancel

When this button is clicked, the Load File window (see FIG. 18) returns.

1913: A line of measured data on the graph

1914: Mark position

1915: A mouse line indicating the position of the mouse cursor (which moves as the mouse moves)

The position of the mouse line is given in the box 1907.

2001: A field to display a data count at the position of a left mark (odd-numbered) in a mark pair To delete this count, click its checkmark to remove

2002: A field to display a data count at the position of a right mark (even-numbered) in a mark pair To delete this count, click its checkmark to remove

2003: A box to enter a count value or time of the position of a mark to be added

2004: When this button is clicked, a mark is put on the position equivalent to a value entered in the box 2003.

2005: When this button is clicked, addition or deletion of data is reflected on the graph and processes.

Figure 24:
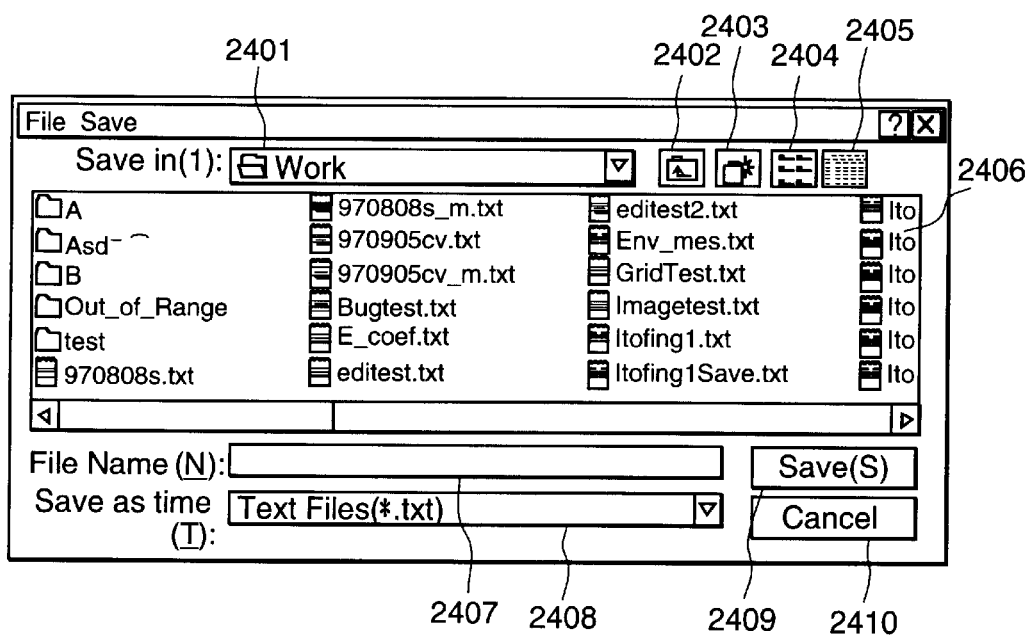
FIG. 24 is a File Save dialog box displayed on the display unit.
Figure 29:
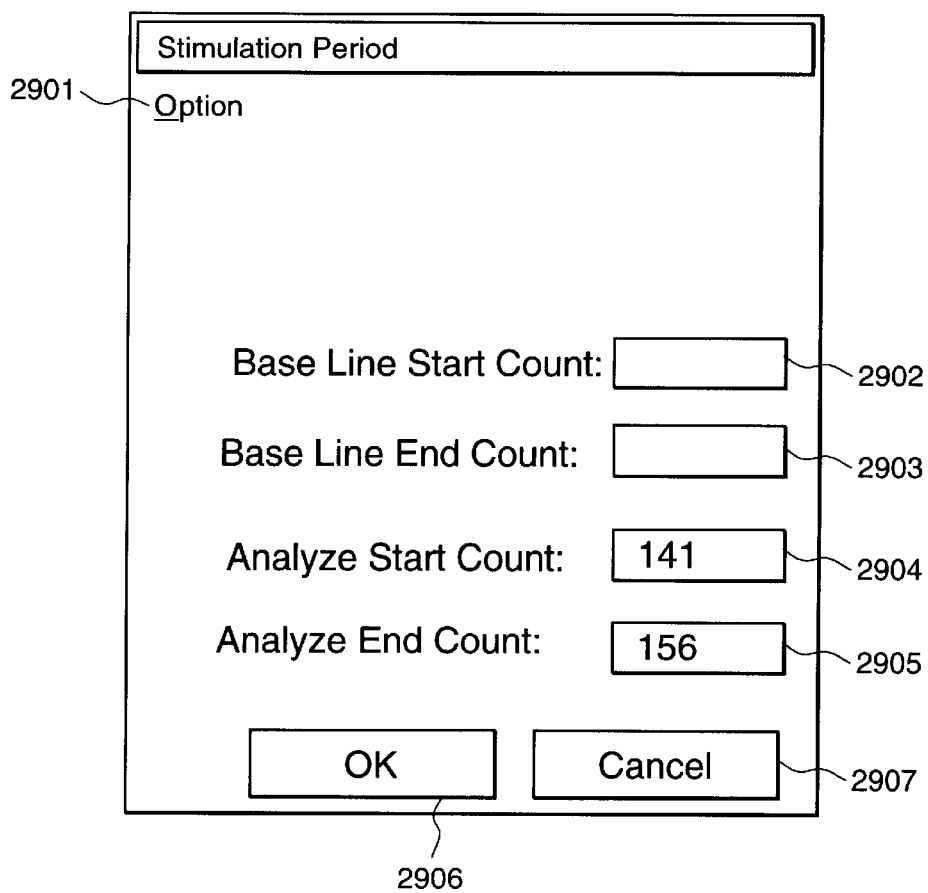
FIG. 29 is a dialog box for setting a stimulation period (process time for analysis of non-summing averages) displayed on the display unit.

FIG. 24, FIG. 25, and FIG. 29 which are selectively displayed in the edition of the Edit Mark window (see FIG. 19) have the following items and functions:

FIG. 24 (File Save window) (at S25)

2401: A box to specify a folder (directory)

2402: A One-Up-Level button to go up to a folder on the one-up level in the "tree" structure

2403: A New Folder button to create a new folder

2404: A List button to display the contents of a specified directory

2405: A Details button to display the more details of a list displayed by the List button

2406: An area for displaying folders and files in the specified directory

2407: A box to enter a file name

This box automatically displays a file name which is selected in the list area 2406.

2408: A box to select a type of the file

The files of the type selected here are displayed in the list area 2406.

2409: A button to save a selected file and proceed

2410: A button to cancel the setting on this window and return to the window of FIG. 19.

Figure 6:
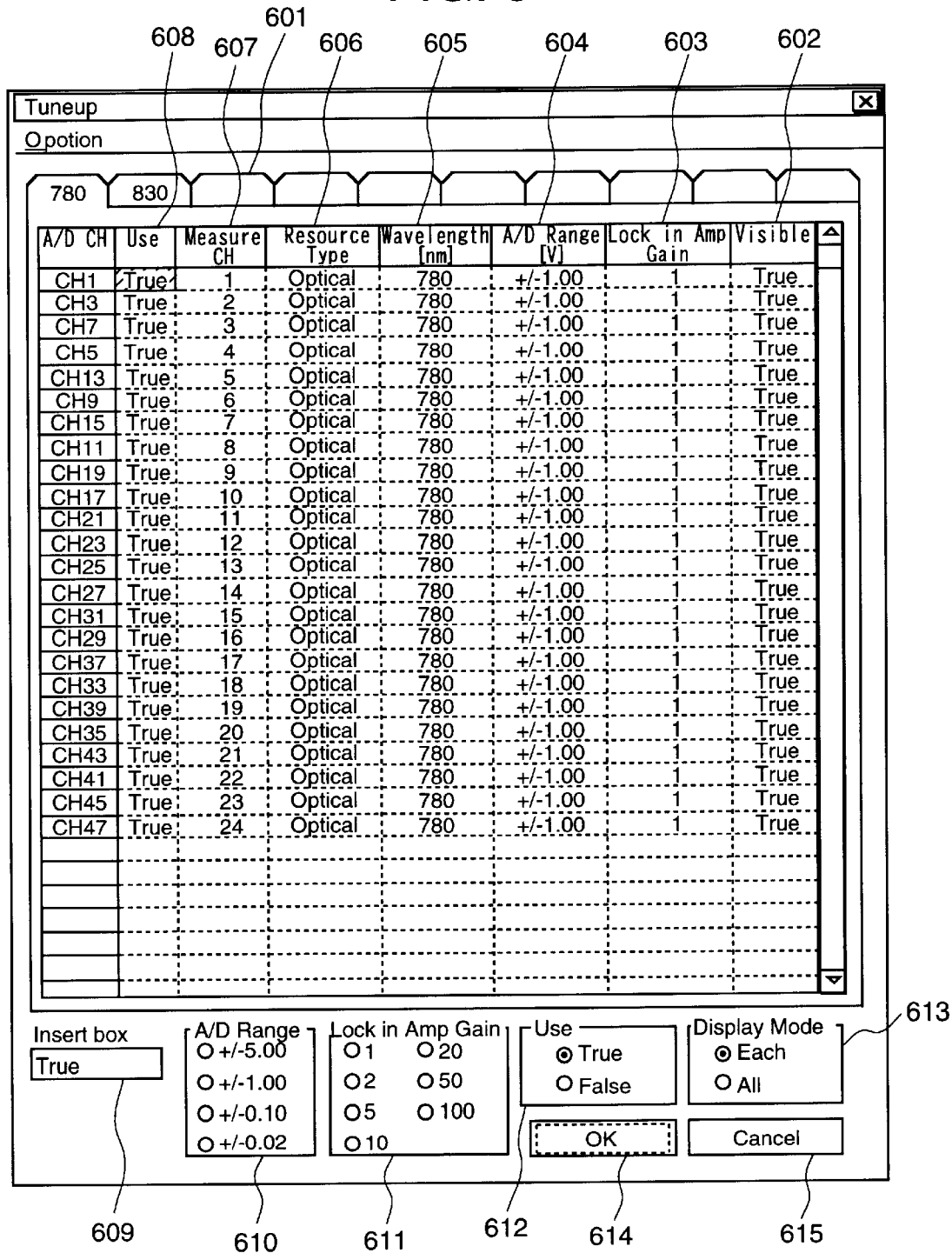
FIG. 6 is a window for entering conditions of measurement and display on the display unit.

FIG. 6 (Window to enter conditions of measurement and display) (at S26)

The items and functions of this window are those of step

FIG. 25 (Process time definition window for summing average analysis) (at S27)

2501: When this button is clicked, the Option menu appears and the Fitting Curve Degree window (see FIG. 26) can be displayed selectively.

2502: A box to enter a time period T1 before a load is applied in FIG. 11

2503: A box to enter a releasing time period T2 in FIG. 11

2504: A box to enter a time period after a load is applied in FIG. 11

2505: A box displaying a count value equivalent to the first mark position

No value can be entered in this box.

2506: A box displaying a count value equivalent to the second mark position

No value can be entered in this box.

Figure 27:
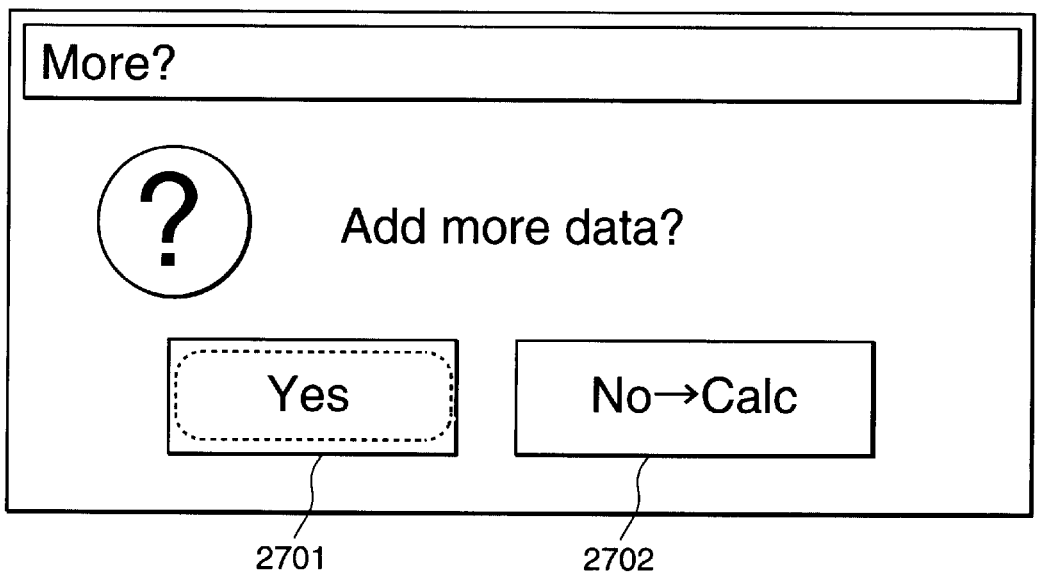
FIG. 27 is a dialog box for adding a process file displayed on the display unit.

2507: A button to end the setting on this window and call the "More?" window (to add another process file) as shown in FIG. 27.

2508: When this Cancel button is clicked, the Edit Mark and the Edit Mark (Sub) windows (see FIG. 19 and FIG. 20) return.

FIG. 29 (Process time definition window for non-summing average analysis) (at S28)

The non-summing average analysis unlike the summing average analysis requires a load application time T1 in FIG. 11. The data is obtained by extrapolation of the fitting curve.

2901: When this button is clicked, the Option menu appears and the Fitting Curve Degree window (see FIG. 26) can be displayed selectively.

2902: A box to enter a starting count or time of the load-application time period T1 in FIG. 11

2903: A box to enter an ending count or time of the load-application time period T1 in FIG. 11

2904: A box to enter an analysis starting count or time

2905: A box to enter an analysis ending count or time

2906: A button to end the setting on this window and proceed to the "Make Topograph?" window (see FIG. 28)

2907: When this Cancel button is clicked, the Edit Mark and the Edit Mark (Sub) windows (see FIG. 19 and FIG. 20) return.

Figure 26:
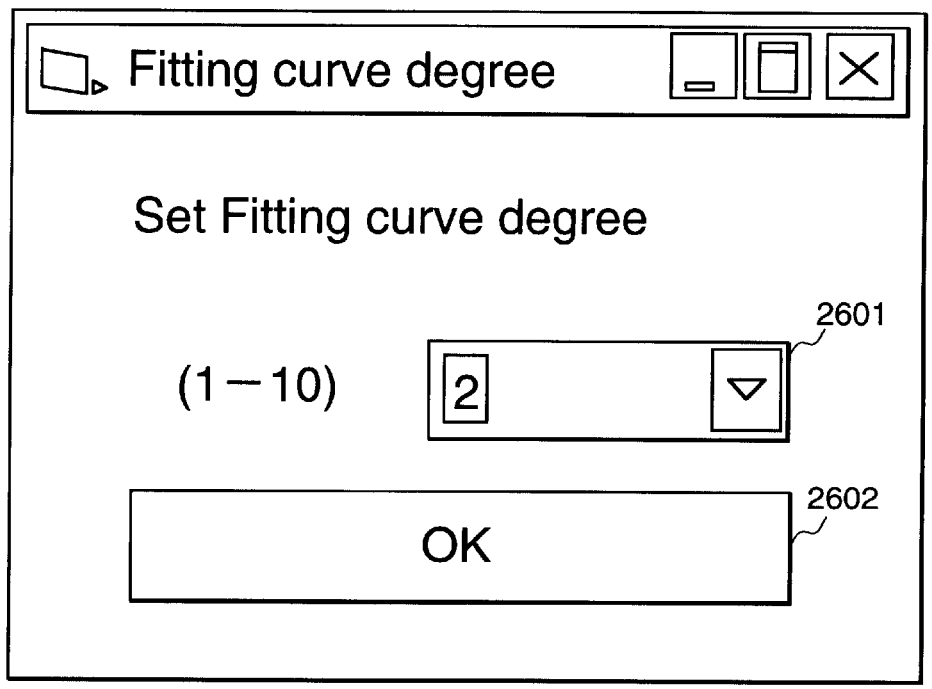
FIG. 26 is a dialog box for setting a fitting curve degree displayed on the display unit.

FIG. 26 and FIG. 27 which are selectively displayed in the edition of the stimulation Period windows (see FIG. 25 and FIG. 29) have the following items and functions:

FIG. 26 (Fitting Curve Degree window) (at S29)

2601: A box to enter the number of degrees of the fitting curve (approximate curve of measurement data) used for calculation of a change rate of hemoglobin Values of 0 to 9 can be specified as a degree. When no degree is specified, a value of 2 is automatically used as default. When a value of 10 to 19 is specified, fitting curves of degree 0 (for specification of a value of 10) to degree 9 (for specification of a value of 19) are determined as a baseline from the time period T1 (before load application) specified in FIG. 11. When a value of 99 is specified, the baseline is obtained from the measuring signal in the time period T1.

2602: A button to close this window and return to a window of FIG. 25 or FIG. 29

FIG. 27 ("More?" window) (at S30)

2701: Click this button to process measuring data of another file for summing average analysis. When this button is clicked, the File Load window (see FIG. 18) returns and the setting on FIG. 19, FIG. 20 and FIG. 25 is repeated. The second and later setting changes are disabled on the window of FIG. 25.

2702: When this button is clicked, the system starts to calculate the concentration of hemoglobin and displays the "More Topograph?" window (dialog box; see FIG. 28) (at S31).

Figure 28:
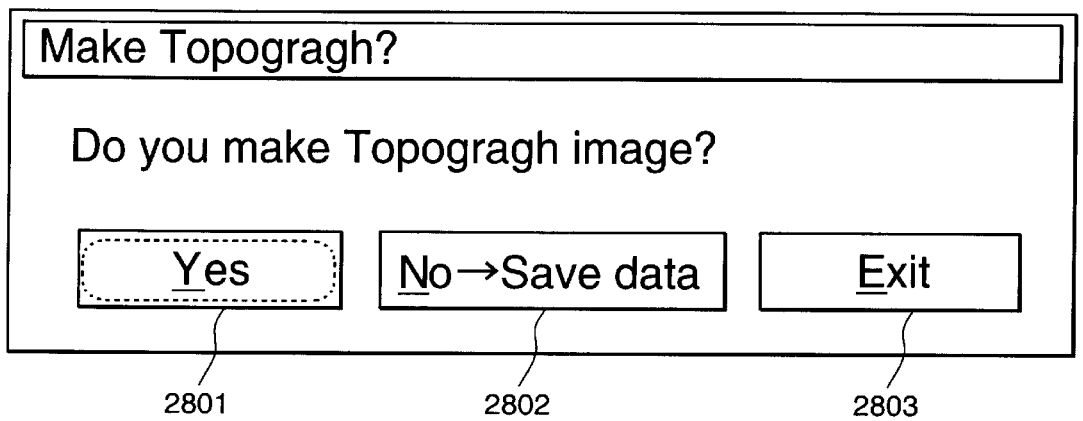
FIG. 28 is a dialog box for asking the operator whether the operator actually wants a topographic image.

The window of FIG. 28 has the following items and functions:

2801: Click this button to start creation of a topographic image (creation of a graph). When this button is clicked, the Topograph Parameter (Parameter) window (see FIG. 30) or the Topograph Parameter (A/D CH Combination) window (see FIG. 31) appears (S32).

Figure 44:
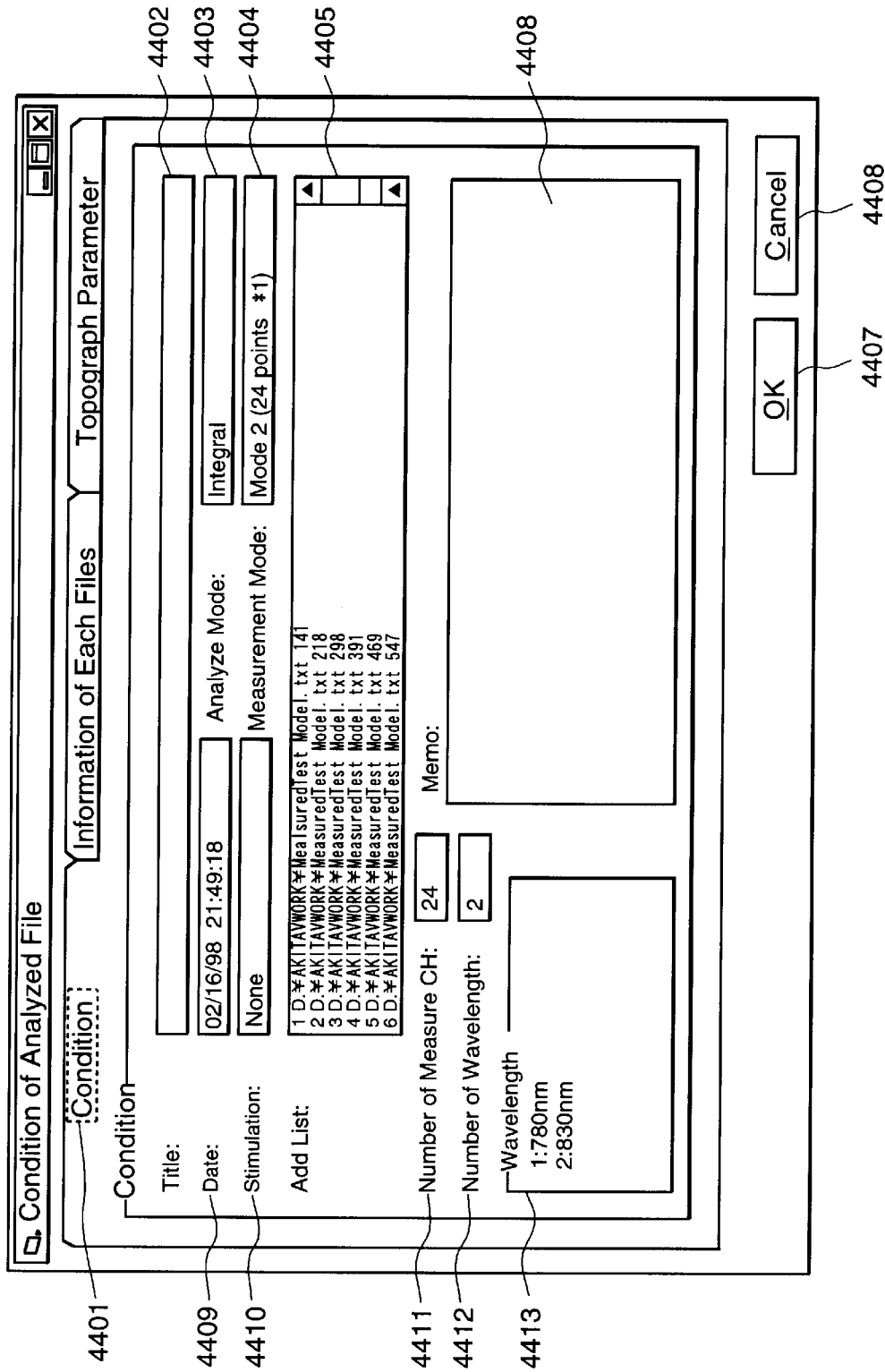
FIG. 44 is a Condition of Analyzed File dialog box displayed on the display unit.

2802: Click this button to save analysis data. When this button is clicked, the Condition of Analyzed File window (see FIG. 44) appears on-screen (at S33). When the operator clicks the Cancel button 4408, the Select Graph window (see FIG. 47) appears. When the operator clicks the OK button 4407, the File Save window (see FIG. 24) appears (at S34) to save the result of processing as a file. The content of the Condition of Analyzed File window (see FIG. 44) will be described in detail below. When the Save button 2409 on the File Save window (see FIG. 24) is clicked, the data is saved and the Select Process window (see FIG. 16) returns. When the Cancel button 2410 is clicked, the "Make Topograph?" window (see FIG. 28) returns.

2803: Click this button to exit to the Select Process window (see FIG. 16).

When the "Parameter" tab is clicked on the Topograph Parameter window (FIG. 30 or FIG. 31), the Topograph Parameter (Parameter) window (see FIG. 30) appears. When the "A/D CH Combination" tab is clicked, the Topograph Parameter (A/D CH Combination) window (FIG. 31) appears. The Topograph Parameter windows (FIG. 30 and FIG. 31) have the following items and functions:

3001: Select hemoglobin data whose topographic image you want to display in this field.

3002: Select whether statistic processing is required. Select "None" to create topographic images without statistic processing or "Mahalanobis" to create topographic images with statistic processing. The statistic processing is done with signal fluctuations as a variable. A typical statistic processing is the "t" test.

3003: Select a mode of setting the position of a measuring channel. Select "Auto" for automatic assignment of a channel position or "Manual" to set a channel position manually. The "Number of Face" box is used to specify a number of faces to be measured.

3004: Select an average mode here.

Natural: No averaging is done when this option is selected.

Average: Averaging is done at every specified count on the X-axis when this option is selected Averaging Counts: A box to enter a count at which averaging is done Splitting count: A box to enter a count which is placed in the center of an averaging area in which averaging is done at a value specified in the Averaging Counts box Moving average: A moving averaging is done when this option is selected.

The number of points for the moving average (generally called a cardinal number) can be entered in this box.

3005: A button to end the setting

When "Manual" is already selected as "Position Mode" 3003, a window for setting irradiating and detecting positions for creation of a topographic image (see FIG. 32) appears on screen (at S35). When "Auto" is already selected as "Position Mode" 3003, a window for setting irradiating and detecting positions for creation of a topographic image (see FIG. 33) appears on screen (at S37).

3006: A Cancel button

3101: A box used to specify a combination of A/D conversion channels

When one measuring channel has three or more wavelengths, you can select two wavelengths in combination for calculation of the concentration of hemoglobin.

Figure 32:
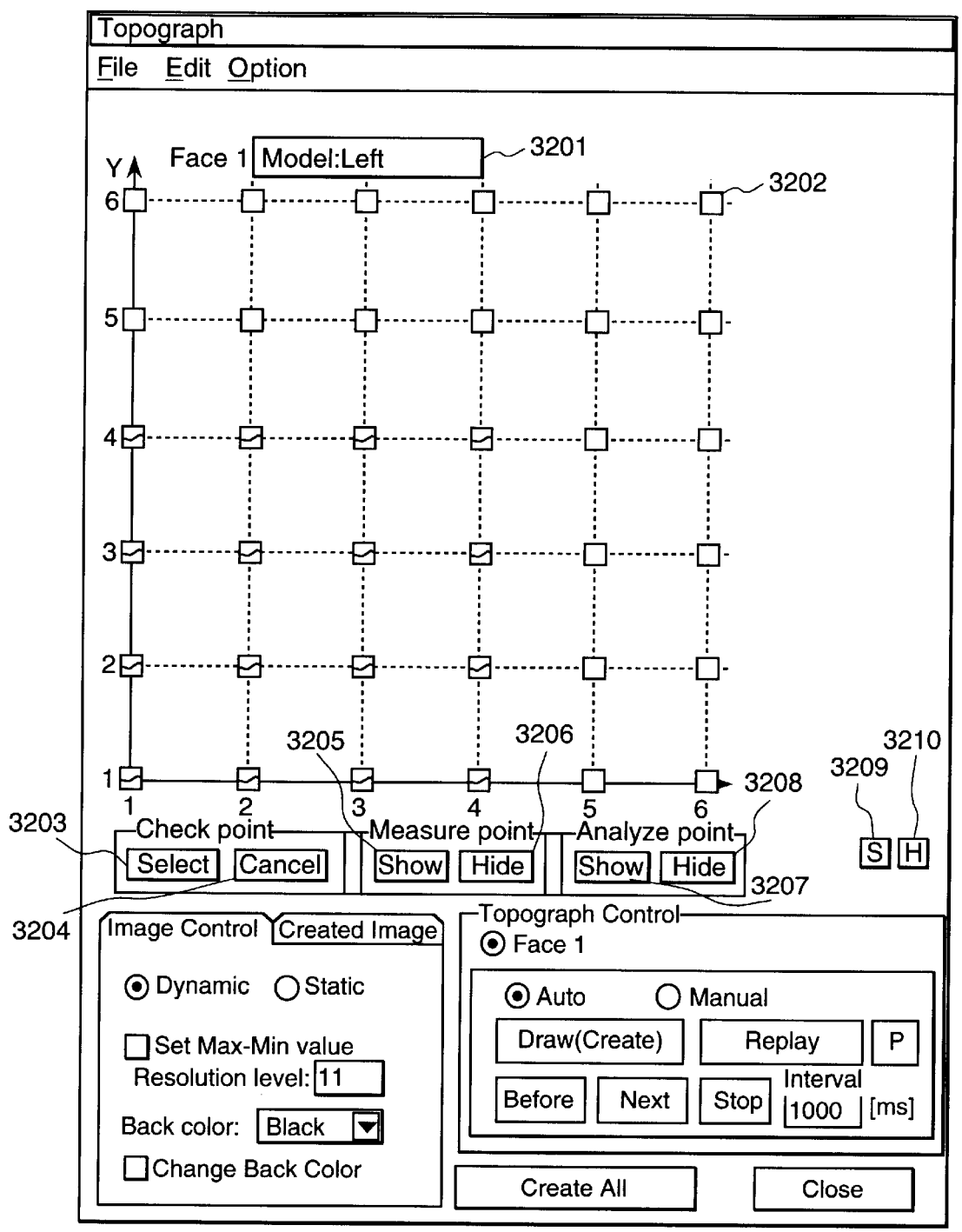
FIG. 32 is a window for setting positions of irradiation and detection for topographic images displayed on the display unit.

The window of FIG. 32 has the following items and functions:

3201: A box to input and display the title of the graph

3202: A check box used to select an irradiating or detecting position by giving a checkmark here To give a checkmark in the check box, position the mouse cursor in the check box and double-click. The check mark disappears when you double-click once more.

3203: When this Select button is clicked after positions for irradiation and detection are set, the Topograph window of FIG. 32 turns into the Topograph window of FIG. 33 (for setting measuring positions for creation of a topographic image) (at S36).

3204: When this Cancel button is clicked, the current setting is cancelled and the Topograph window of FIG. 32 turns into the Topograph window of FIG. 33.

3205: Click this Show button to show the irradiating and measuring positions you have selected.

3206: Click this Hide button to hide the irradiating and measuring positions you have selected.

3207: Click this Show button to show the measuring channels you have selected.

3208: Click this Hide button to hide the measuring channels you have selected.

3209: Click this S button to show the buttons 3203 to 3208.

3210: Click this H button to make the buttons 3203 to 3208 invisible.

Figure 33:
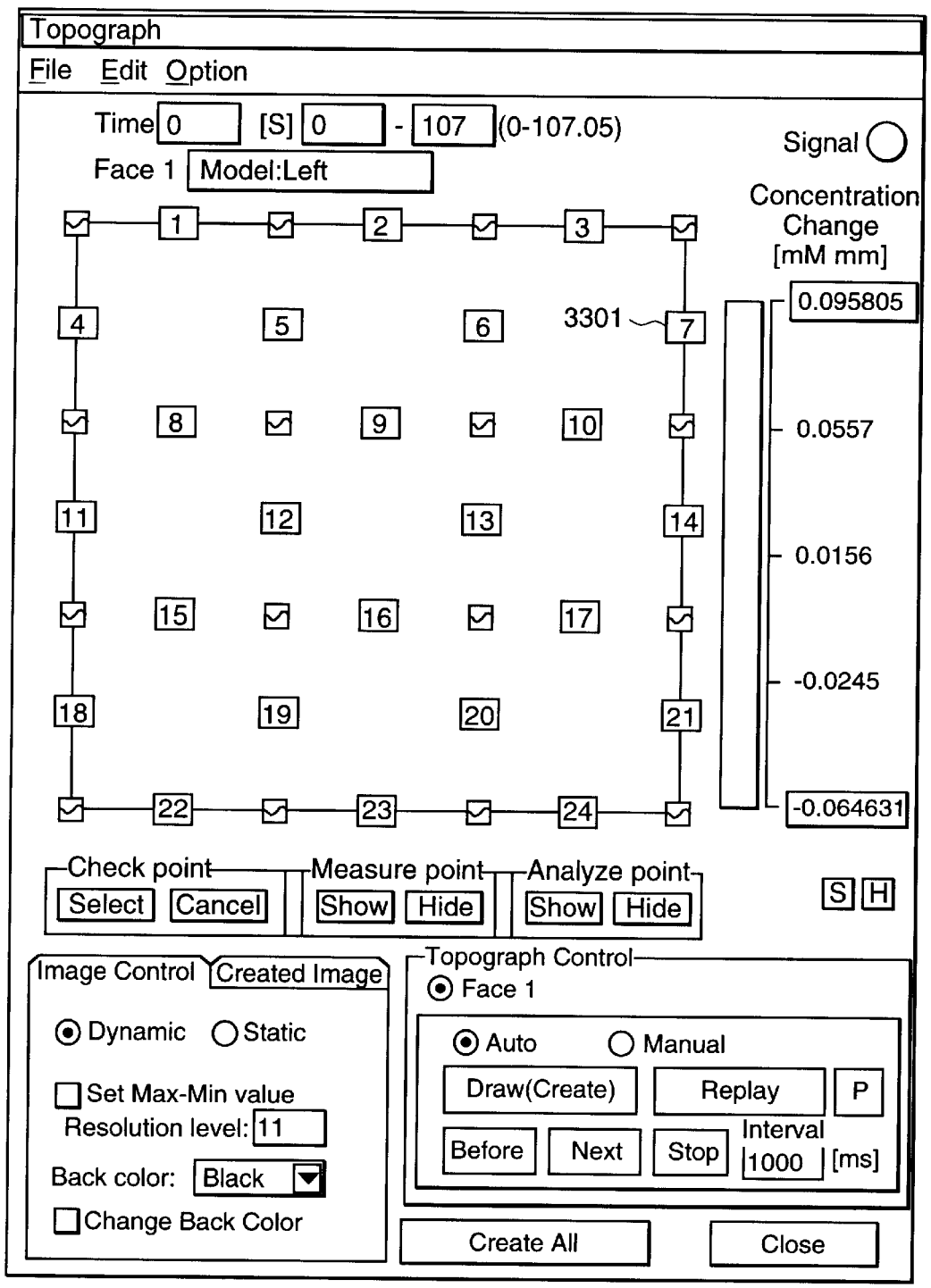
FIG. 33 is a window for setting positions of measurement for topographic images displayed on the display unit.
Figure 34:
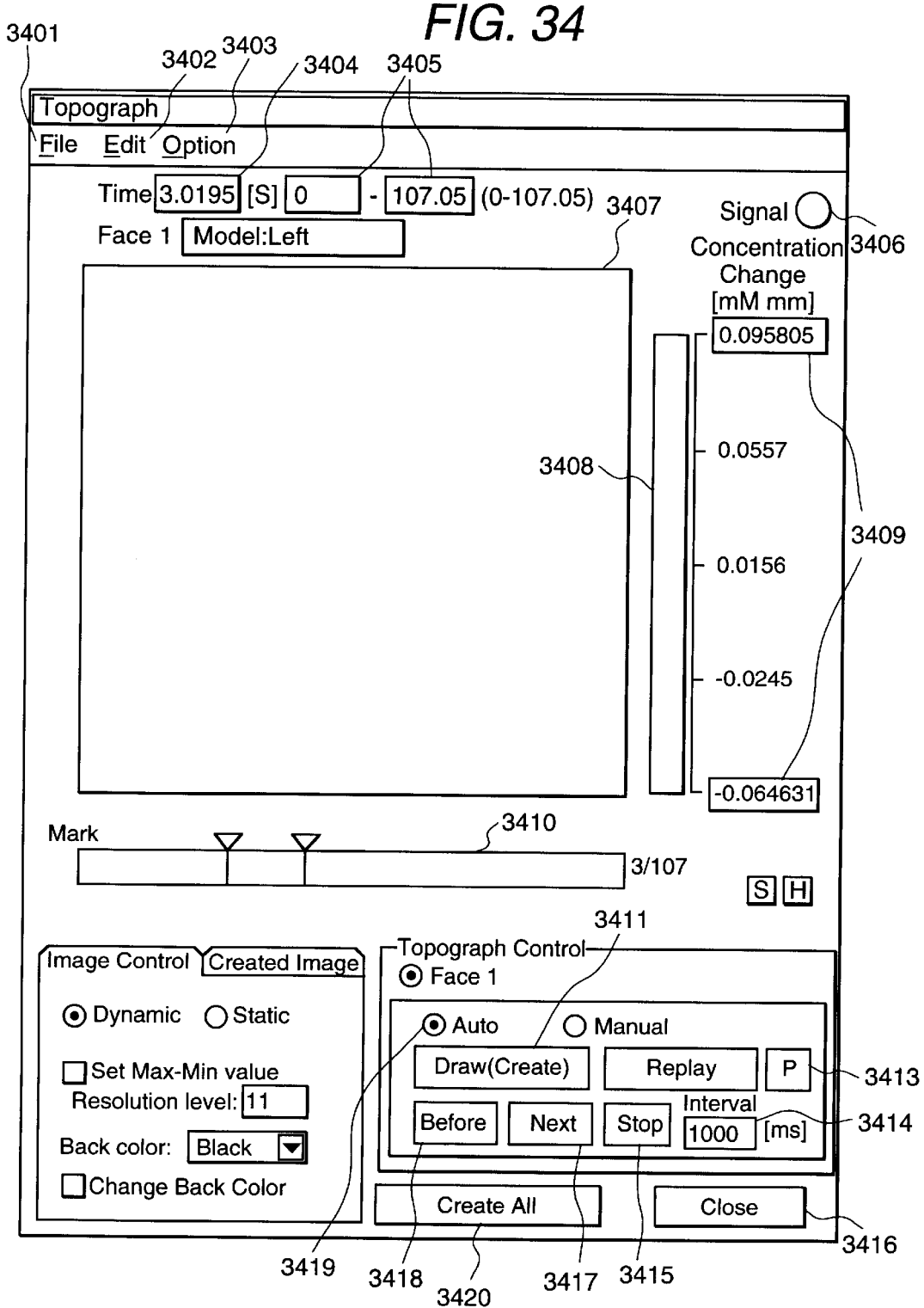
FIG. 34 is a window for editing and displaying topographic images on the display unit.
Figure 35:
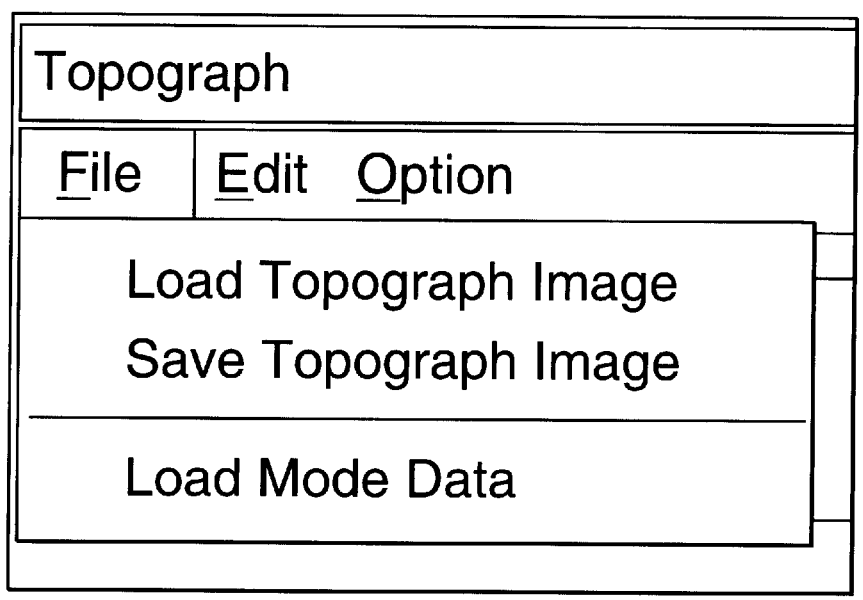
FIG. 35 is a File menu of the Topograph window as shown in FIG. 34.
Figure 36:
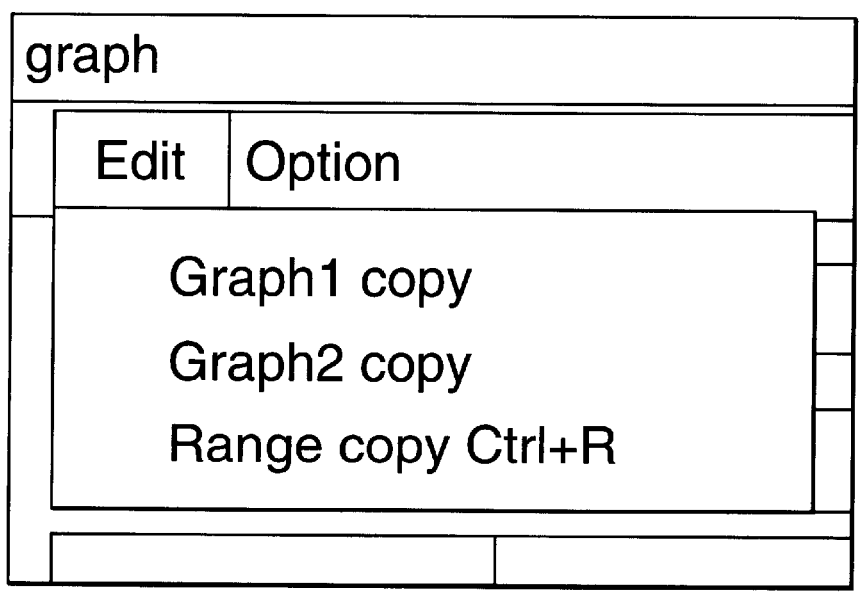
FIG. 36 is an Edit menu of the Topograph window as shown in FIG. 34.

The lower part of the window of FIG. 33 is the same as that of the window of FIG. 32. A measuring channel number is set in this box 3301. When the mouse's left button is double-clicked, the internal counter is incremented by one and thus serial numbers are automatically set in these boxes. To decrement the internal counter by one, click the mouse's left button once while pressing on the Shift key.

The window of FIG. 34 is used to create a topographic image of the concentration of hemoglobin (Hb) from the measured time-series signals, display static or animated images, and to save the data. This example shows one topographic image but it is possible to display two or more images simultaneously. The window of FIG. 34 has the following items and functions:

3401: When the File button is clicked, the File menu pops up. The File menu contains three options "Load Topograph Image" (to load a saved topographic image), "Save Topograph Image" (to save a created topographic image), and "Load Mode Data" (to load a mode file which contains conditional data representing a measurement mode). When "Load Topograph Image" is chosen, the Load Topograph Image window (see FIG. 40 or FIG. 41) appears on-screen (at S38). When "Save Topograph Image" is chosen, the Save Topograph Image window (see FIG. 42 or FIG. 43) appears on-screen (at S39). When "Load Mode Data" is chosen, the File Load window (see FIG. 24) appears on-screen (at S40).

3402: When the Edit button is clicked, the Edit menu pops up. The Edit menu contains three options "Graph1 copy," "Graph2 copy," and "Range copy." When "Graph1 copy" is chosen, the Face 1 image is displayed. When "Graph2 copy" is chosen, the Face 2 image is displayed. When "Range copy" is chosen, the color range is copied onto temporary storage of the computer.

3404: When "Manual" is chosen in "Topograph Control" area, a time on the time axis of the Hb concentration change rate data which is specified in FIG. 32 is entered in this box. When "Auto" is chosen in the "Topograph Control" area, this box also displays a processing time while image processing is in progress or an image display time while an already-created image is being displayed.

3405: When "Auto" in the "Topograph Control" area and "Create All" are chosen, these boxes input and display an image creation starting time (the left box) and an image creation ending time (the right box) on the time axis of the specified Hb concentration change rate data.

3406: An indicator to indicate the processing status by color: red for "Data processing in progress" (Topograph creation in progress) or red for the other states.

3407: An area for displaying a created topographic image

3408: A range of topographic colors (contrast width) (color bar relating hemoglobin concentrations to colors)

3409: Boxes to display the maximum Hb concentration (in the upper box) and the minimum Hb concentration (in the lower box) in relation to colors of topographic images To specify maximum and minimum Hb concentrations, click the "Set Max-Min value" checkbox on the Image Control tab and give a check mark in it.

3410: A bar indicating positions (time) and ranges of process data

The whole X-axis indicates a time period during which a topographic image is created. A red vertical line moves together with the displayed image time while the image creation or display is in progress. When the vertical line comes across a triangle mark, the system informs the operator of it by beeps or change of the background color. When an image creation period is specified by boxes 3405, the range is indicated by a horizontal line in cyan. A range enclosed in marks (see FIG. 19) is colored yellow. When "Average" is chosen in the "Average Mode" area of the Topograph Parameter window (see FIG. 30), a Split Count position is displayed.

3411: Click this Draw (Create) button to create a topographic image. When this button is clicked in the Manual mode, one topographic image of a time period specified by boxes 3405 is displayed and the time range for the image creation is indicated by a horizontal line in cyan in the time bar 3410.

3412: When this Replay button is clicked, a topographic image created in the "Auto" mode with "Create All" is redisplayed.

3413: Click the Pause button to temporarily stop image reproduction. Click this button again to restart image reproduction.

3415: Click the Stop button to stop image reproduction started by the Draw (Create) button or the Replay button.

3416: Click this Close button to close the Topograph window.

3417: When this Next button is clicked, the system creates and displays an image at the next sampling time in the Manual mode or an image at the next sampling time of the currently-displayed image in the image creation period in the Auto mode with "Create All." This means forward image reproduction.

3418: This Before button is functionally opposite to the Next button 3417 (playing the preceding frame). This means backward image reproduction.

3419: An area to select a topograph creation mode: "Auto" to create images in a specified range at a time and "Manual" to create one image at a time.

3420: When this button is clicked, the system shows the image type setting-window, creates a plurality of topographic images according to the conditions set on this window, and saves them as a file. The images which are saved here will be loaded and displayed.

Figure 37:
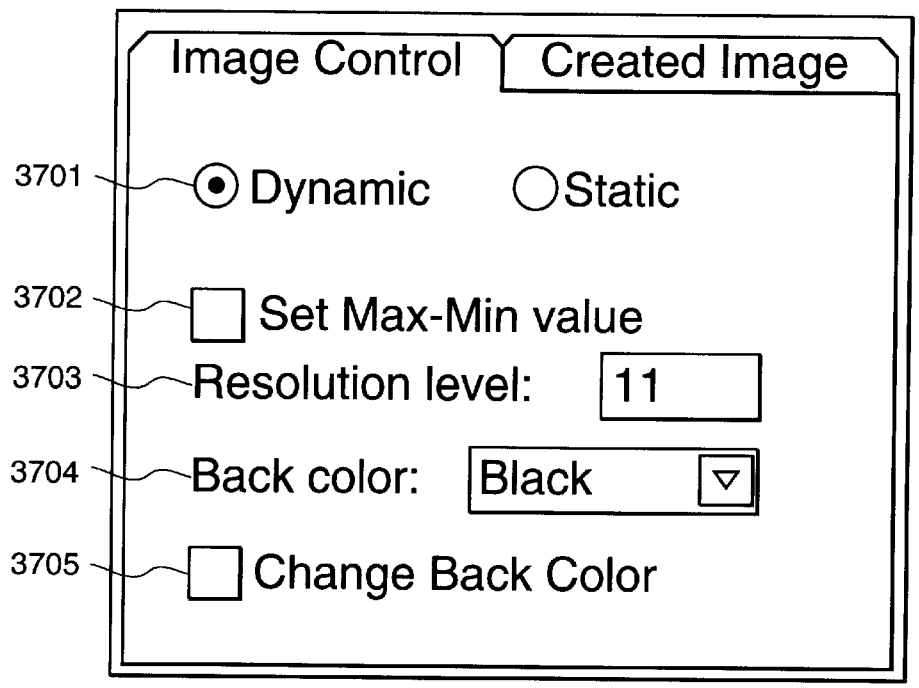
FIG. 37 is an Image Control tab for setting a condition of creating a topographic image as shown in the lower left corner of FIG. 34.
Figure 38:
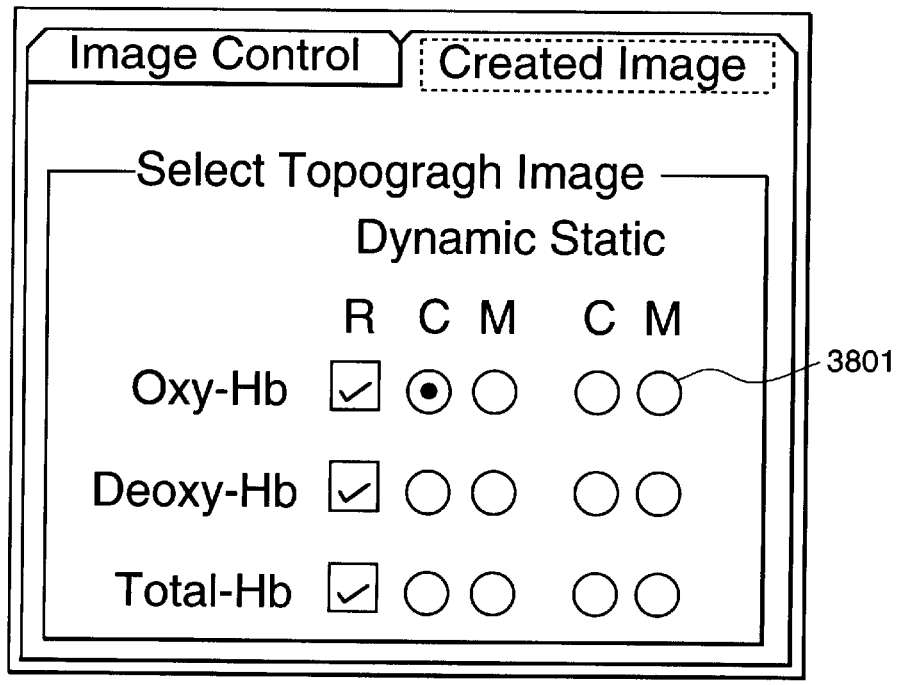
FIG. 38 is a Created Image tab for selecting an image as shown in the lower left corner of FIG. 34.

Windows of FIG. 37 and FIG. 38 appear on the lower left corner of the Topograph window (see FIG. 34). FIG. 37 shows the content of the Image Control tab window and FIG. 38 shows the content of the Created Image tab window. Click the Image Control tab to open the Image Control window or the Created Image tab to open the Created Image window. These windows have the following items and functions:

3701: Option buttons to select "Dynamic" (moving topograph) or "Static" (still topograph)

These options are not available when the "Create All" button is chosen.

3702: Double-click this checkbox (and give a checkmark here) to set the minimum and maximum Hb concentrations related to the colors on the color bar.

3703: A box to enter a resolution level of the topographic image

3704: A box to specify a color of the background of the topographic image

Colors available are black, gray, and white.

3705: Click this checkbox (and give a checkmark here) to change the background color to yellow when a topographic image of a time range enclosed marks is displayed.

3801: This area displays the type (Oxy, Deoxy, Total, Dynamic, Static, Color, or Monochrome) of a topographic image created by selection of the Create button. "C," "M," and "R" respectively stand for "Color," "Monochrome," and "Reversed colors on the color bar." These options are selectable when the type of the created image exists. To display the image, select the image type and click the Replay, Before, or Next button.

Figure 39:
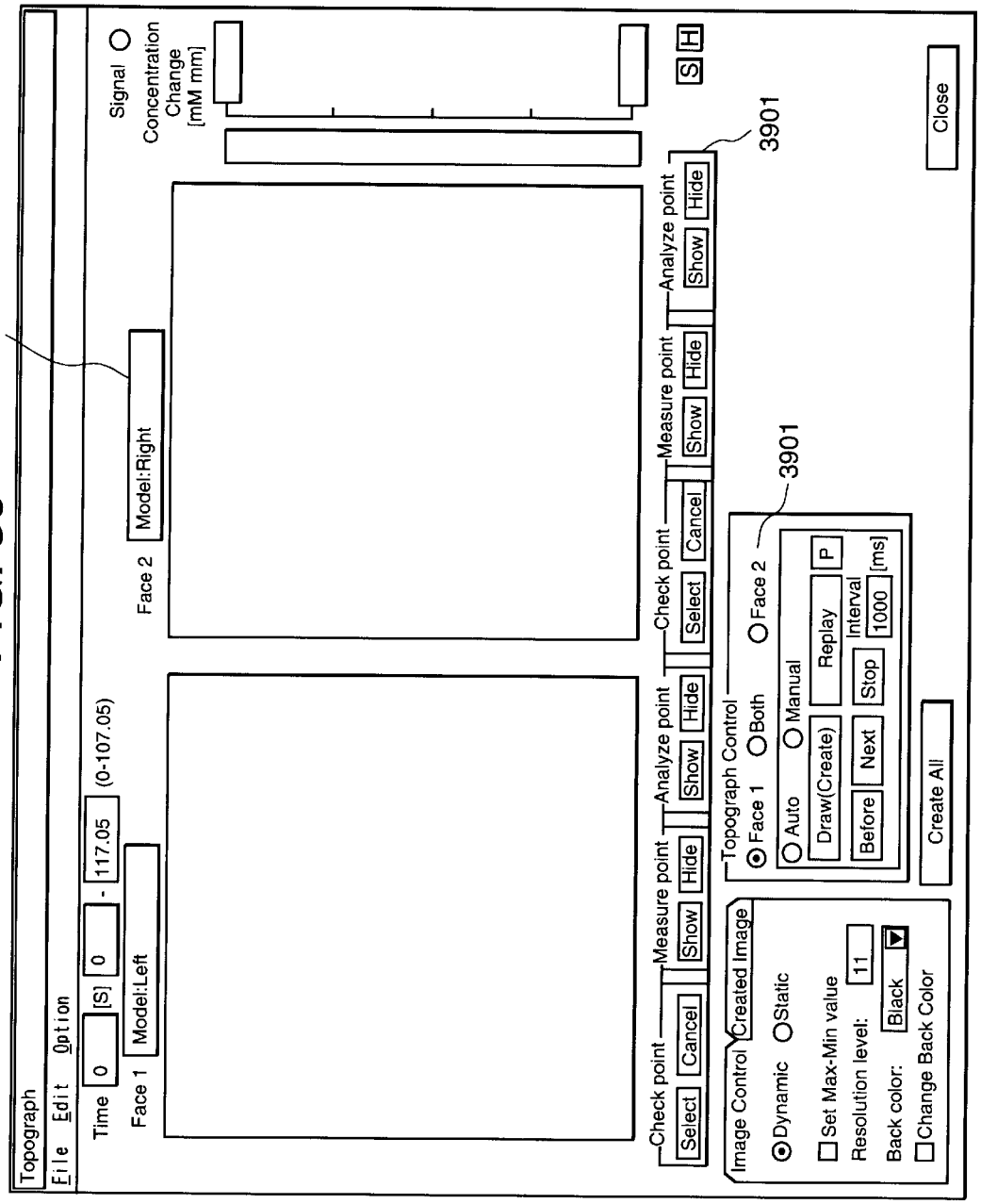
FIG. 39 is a 2-frame window for editing and displaying topographic images on the display unit.

The window of FIG. 39 is displayed instead of the window of FIG. 34 when two faces (measurement areas) are measured and this window is used to edit and display two topographic images. A box 3901 displays the title of the second window. For example, it is possible to measure the left and right cerebrums of the examinee individually and show their images at a time on a single window. Further for reproduction of moving images, a plurality of moving images can be reproduced in synchronism. The area 3902 contains a group of buttons to set measuring positions and others on the second window. These buttons are the same as those 3203 to 3208 of the Topograph window (see FIG. 32). The area 3903 is used to select a window of an image to be processed. Select "Face 1" to process the first image window, "Face 2" to process the second image window, or "Both" to process both first and second image windows.

Figure 40:
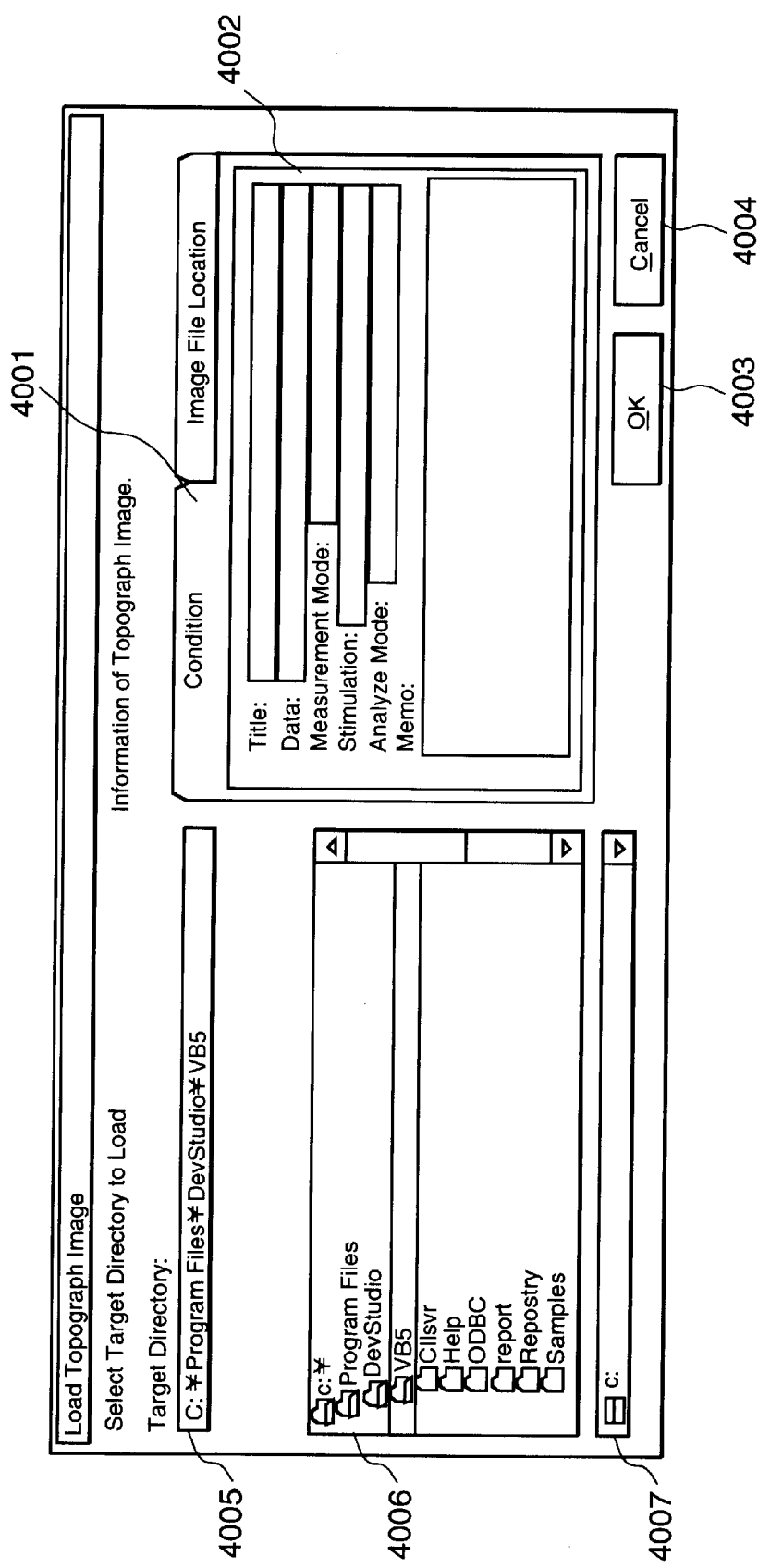
FIG. 40 is a Load Topograph Image dialog box displayed on the display unit.
Figure 41:
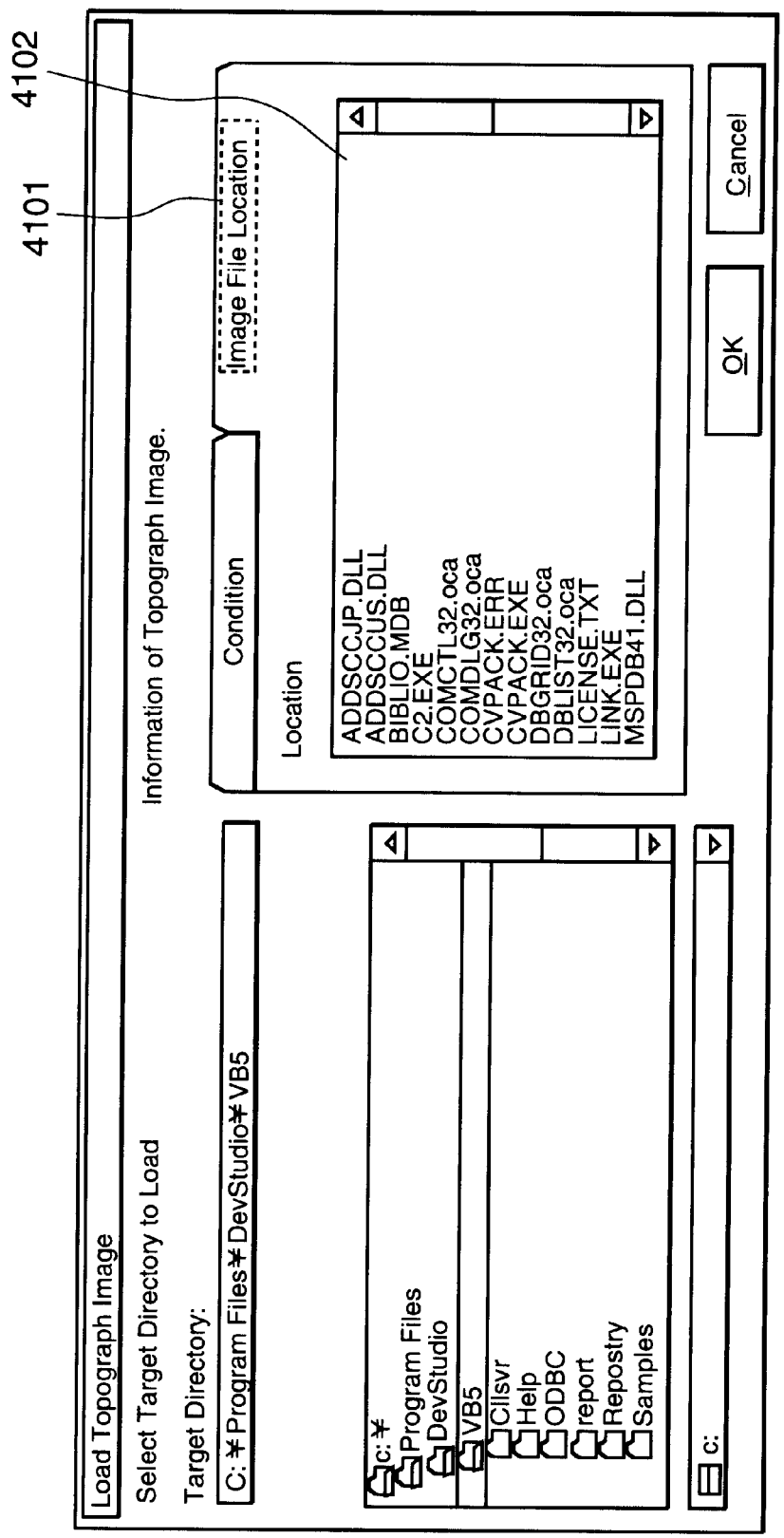
FIG. 41 is a Load Topograph Image dialog box displayed on the display unit.
Figure 42:
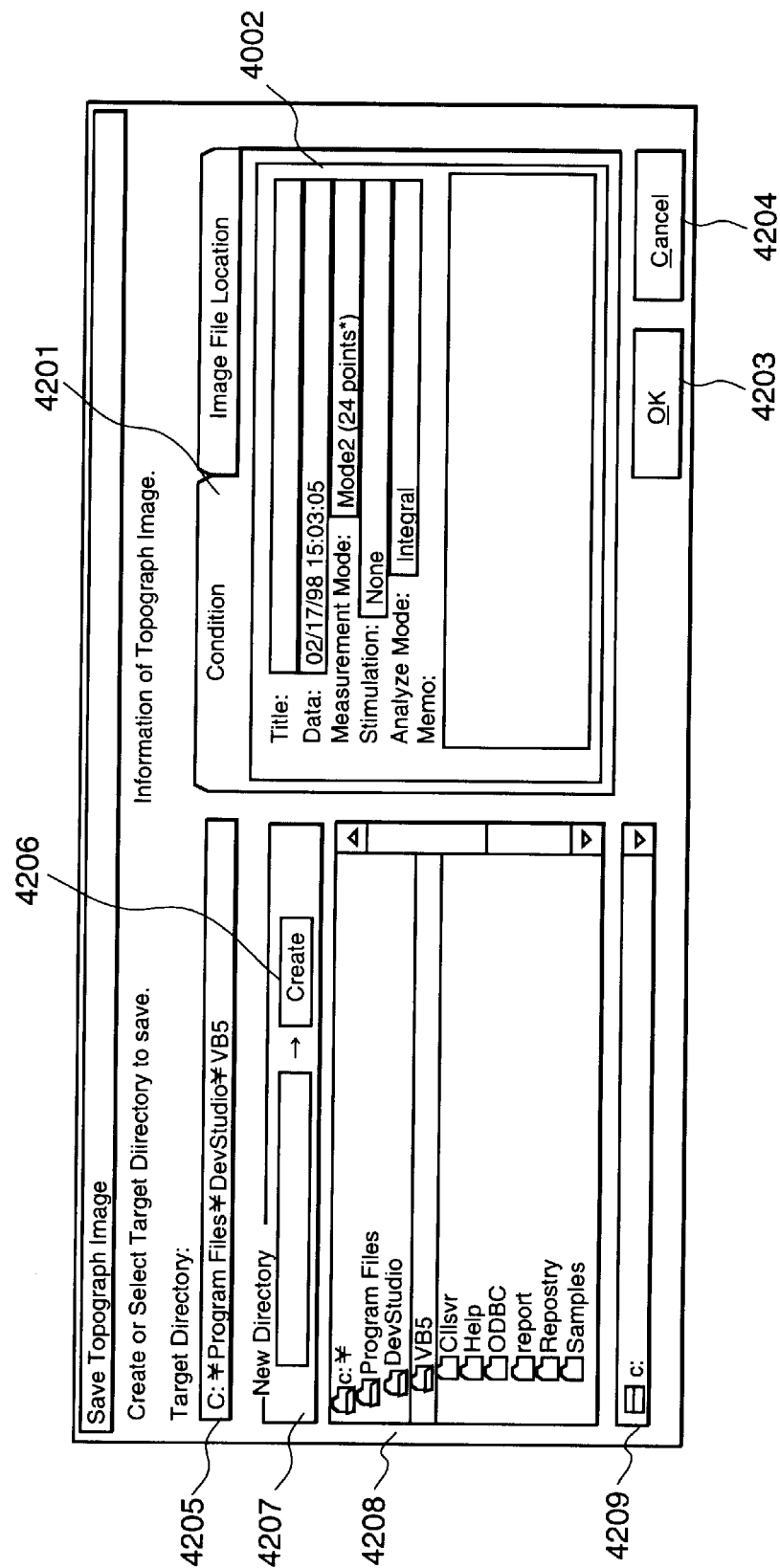
FIG. 42 is a Load Topograph Image dialog box displayed on the display unit.

Windows of FIG. 40 to FIG. 43 which are selectively displayed in windows of FIG. 33 to FIG. 38 have the following items and functions:

FIG. 40 and FIG. 41 (Load Topograph Image window) (S38)

The operator can specify a directory of the topographic image data that the operator wants to load as shown below.

4001: When this Condition tab is clicked, the window of FIG. 40 appears on-screen.

4002: This field displays information of image data to be loaded. The "Analyze Mode" field displays a process mode (Integral or Continuous).

4003: When this OK button is clicked, the system starts to load the specified image data.

4004: A cancel button

When this button is clicked, the Topograph window (see FIG. 34) returns.

4005: This box enters or displays the name of data to be loaded. (The name is saved as a directory name.) Information of image data specified here is displayed in the field 4002.

4006: This field displays a directory or image data names for selection. Select and click an image data name. The path name of the selected directory is displayed in the box 4005.

4007: This field is used to select a storage medium (floppy disk, hard disk, or MO) from which image data is loaded. The directory in the specified storage medium is displayed in the field 4006.

4101: When this Image File Location tab is clicked, the window of FIG. 41 appears on-screen.

4102: This field lists file names which are in the directory specified by the box 4005.

Figure 43:
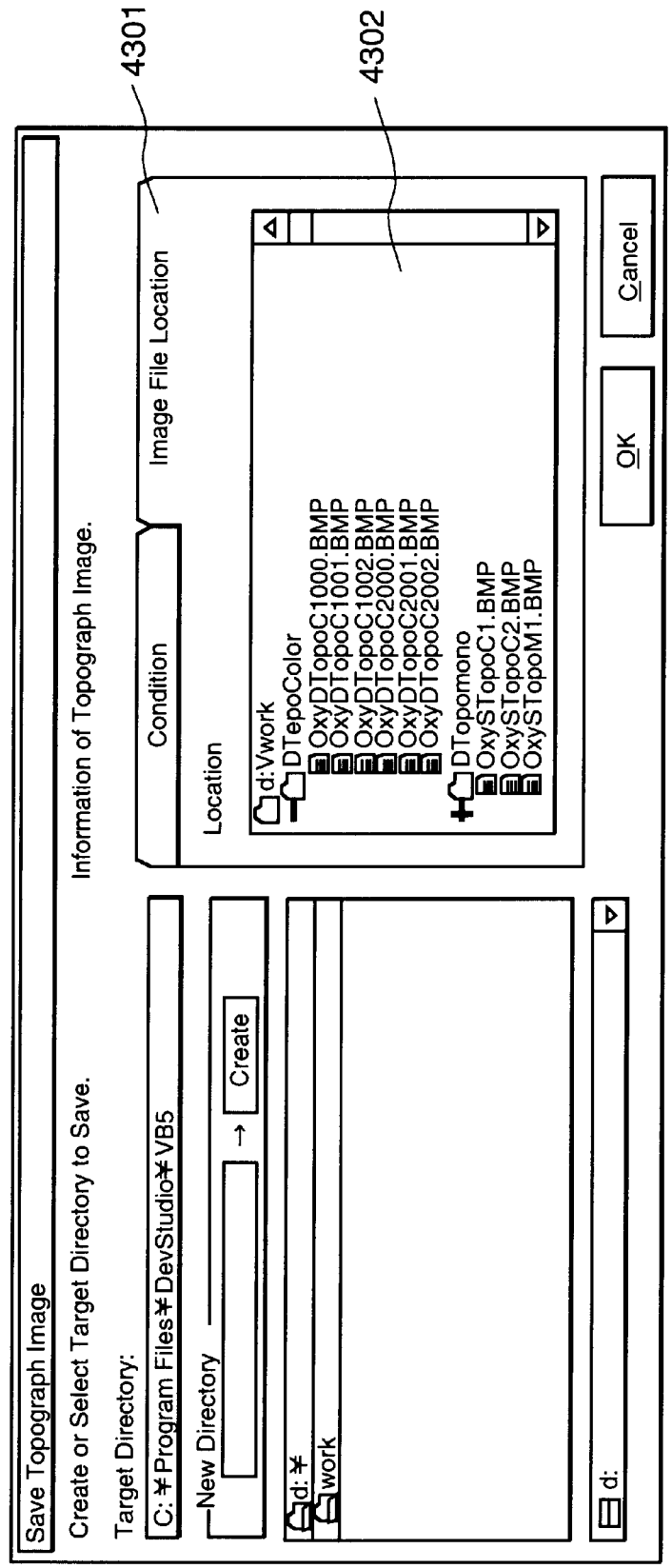
FIG. 43 is a Load Topograph Image dialog box displayed on the display unit.

FIG. 42 and FIG. 43 (Save Topograph Image window) (S39) The operator can specify a directory to which the operator can save the topographic image data as shown below.

4201: When this Condition tab is clicked, the window of FIG. 43 appears on-screen.

4202: This field displays information of topographic image data to be saved.

4203: Click this OK button to save the topographic image data to the specified directory.

4204: A cancel button

When this button is clicked, the Topograph window (see FIG. 34) returns.

4205: This box enters or displays a directory to which the topographic image data is saved.

4206: When this button is clicked, a new directory of a directory name specified by the box 4207 is created under the directory specified by the box 4205.

4207: A box to enter the name of a new directory.

4208: This field lists directories for selection. Select and click a directory. The selected directory is displayed in the box 4205.

4209: This field is used to select a drive. The directory in the specified drive is displayed in the field 4208.

4301: When this Image File Location tab is clicked, the window of FIG. 43 appears on-screen.

4302: This field displays the structure of topographic image data to be saved.

The windows FIG. 42 and FIG. 43 are almost the same as those of FIG. 40 and FIG. 41 except that the windows FIG. 42 and FIG. 43 have the field 4207 and the box 4206 and that letters "Load" are substituted by letters "Save."

FIG. 18 (File Load window) (S40)

The contents of this window are already described. (See S23.)

Figure 61:
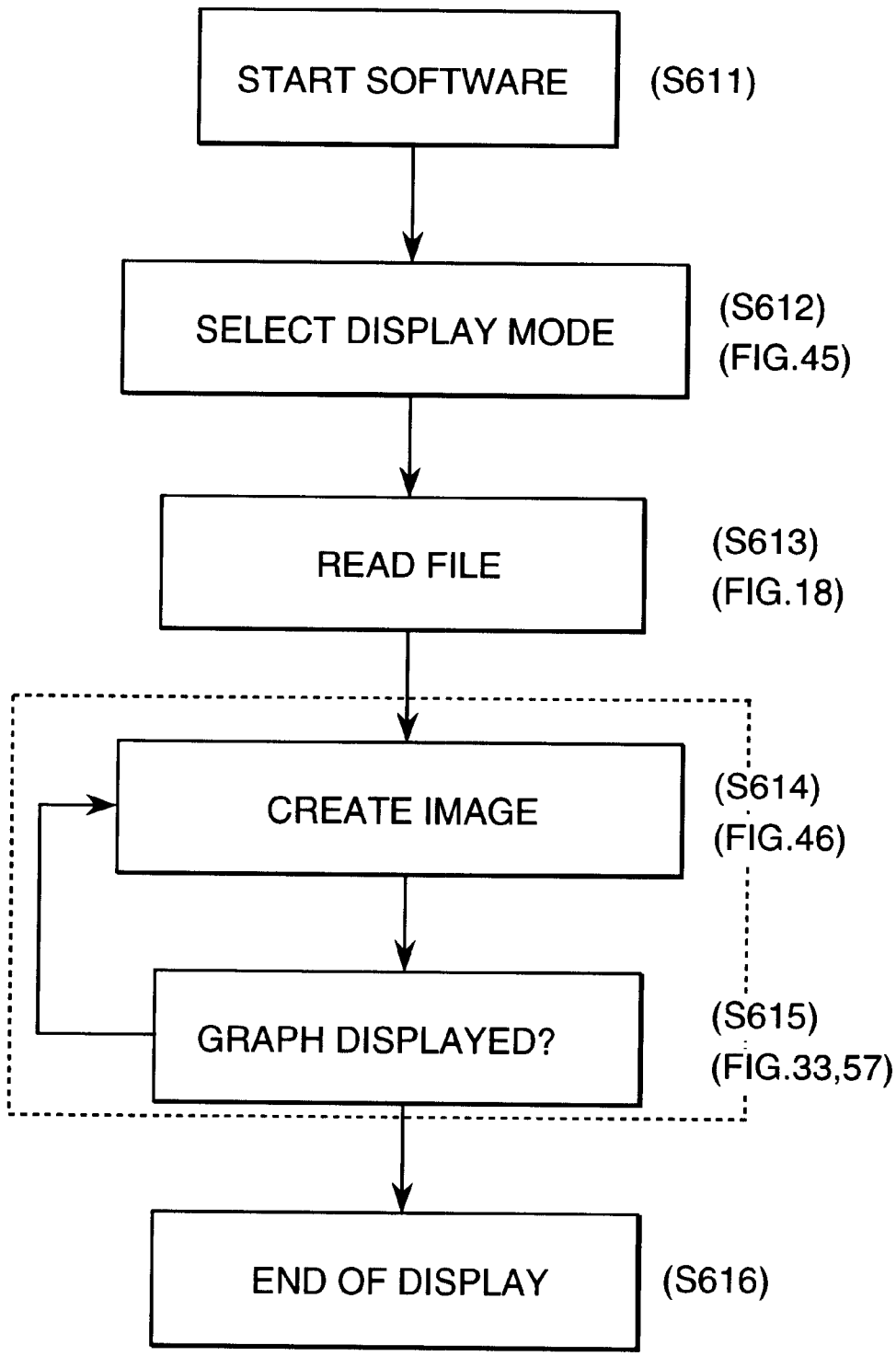
FIG. 61 is a sample process flow in accordance with the present invention which displays data analyzed by the optical measuring apparatus shown in FIG. 1.

FIG. 61 shows a flow of displaying data analyzed by an optical measuring apparatus shown in FIG. 1, which is one embodiment of the present invention. Items related to display will be described in detail referring to FIG. 47 to FIG. 57. As seen from FIG. 61, this flow loosely comprises the steps of starting up an optical measuring program at step S611, changing windows at steps S612 to S615, and ending display at step S616.

Figure 45:
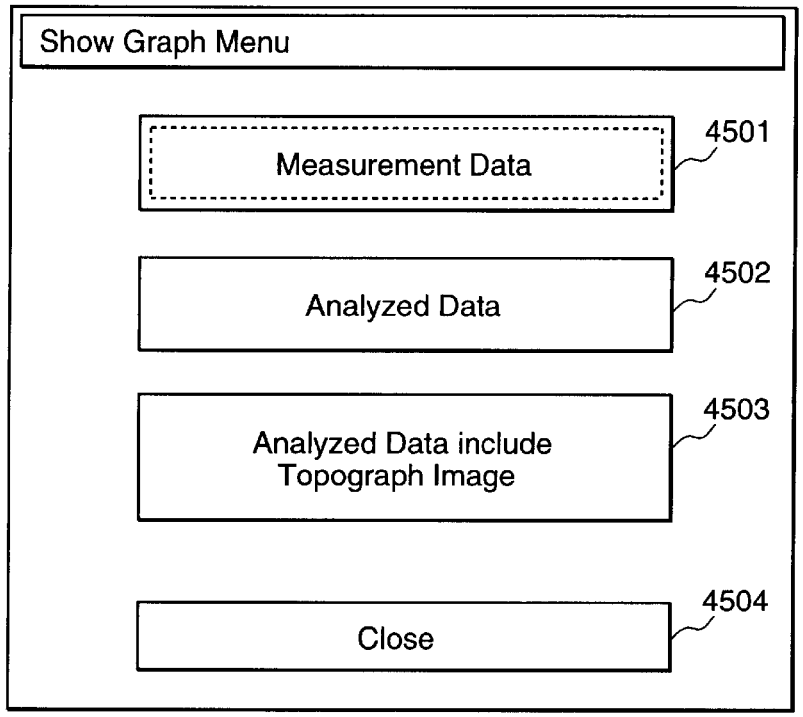
FIG. 45 is a Graph Menu window displayed on the display unit.
Figure 46:
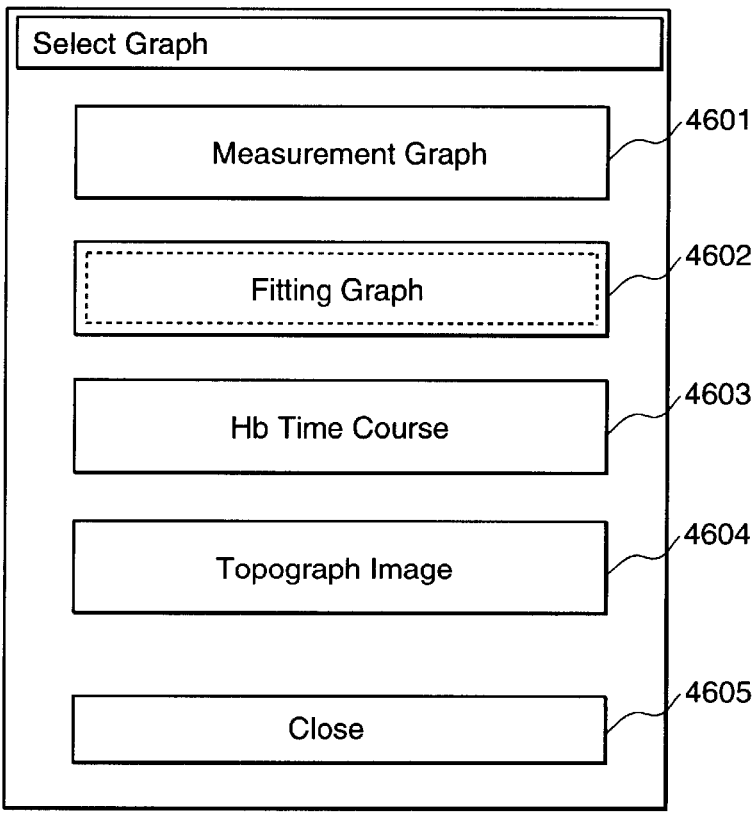
FIG. 46 is a Select Graph window for selecting a graph displayed on the display unit.

The window appearing at step S612 in FIG. 61 is for selection of a display mode as shown in FIG. 45. The window appearing at step S613 is a File Load window as shown in FIG. 18 and used to load a stored data file. The window appearing at step S614 is a Select Graph window as shown in FIG. 46 and used to select a graph to be displayed. The selected graph is displayed at step 615 as shown in FIG. 32 and FIG. 57.

Figure 62:
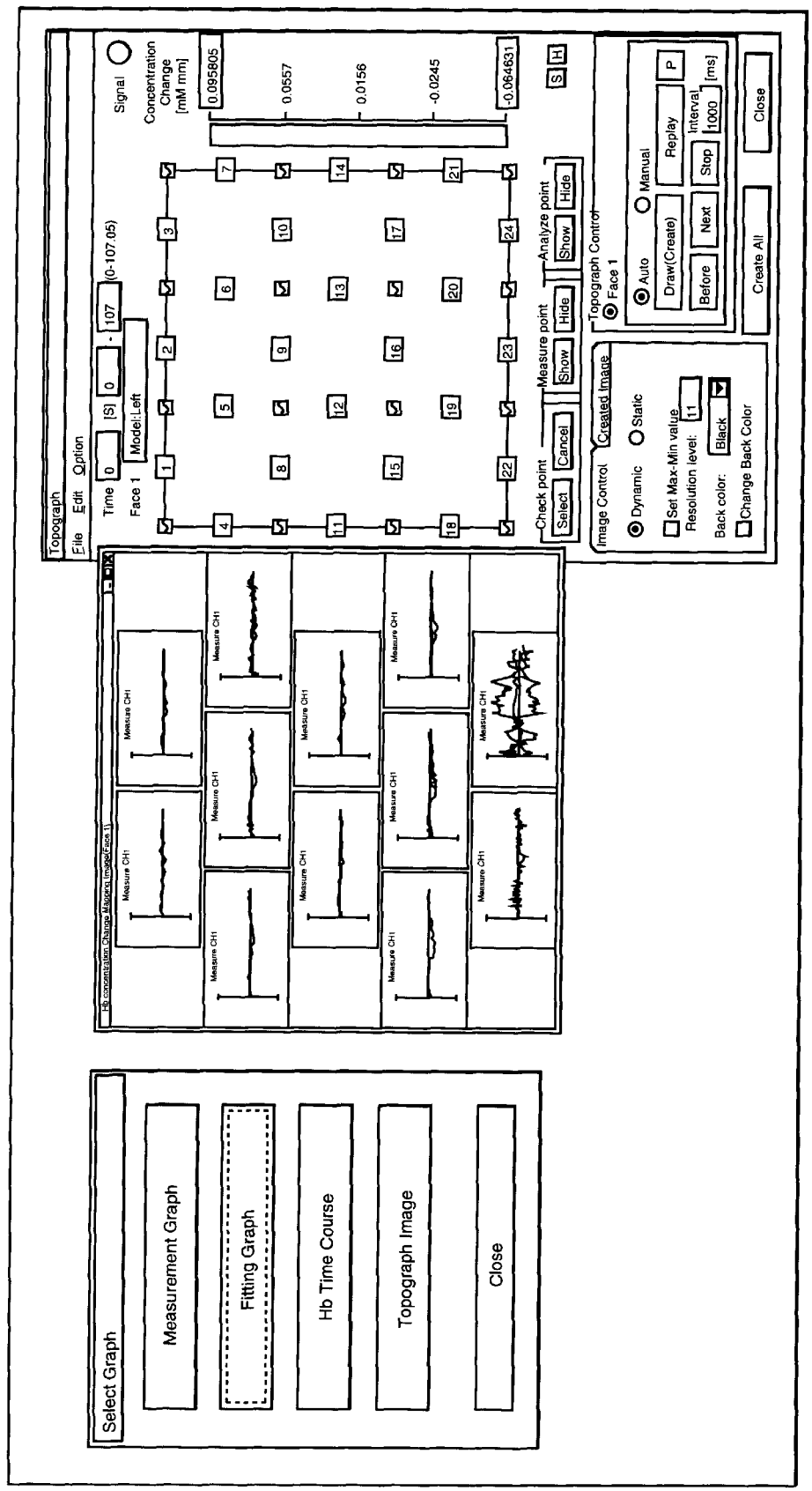
FIG. 62 shows graphic windows displayed on the display unit.

In this case, the Select Graph window (as shown in FIG. 46) and graphs selected by the operator (for example, the Topograph window of FIG. 33 and the Hb concentration graph mapping window of FIG. 57) are displayed on a single window as shown in FIG. 62. With this, the operator can grasp the relationship between measuring positions given by FIG. 33 and Hb concentration changes at a glance.

Figure 57:
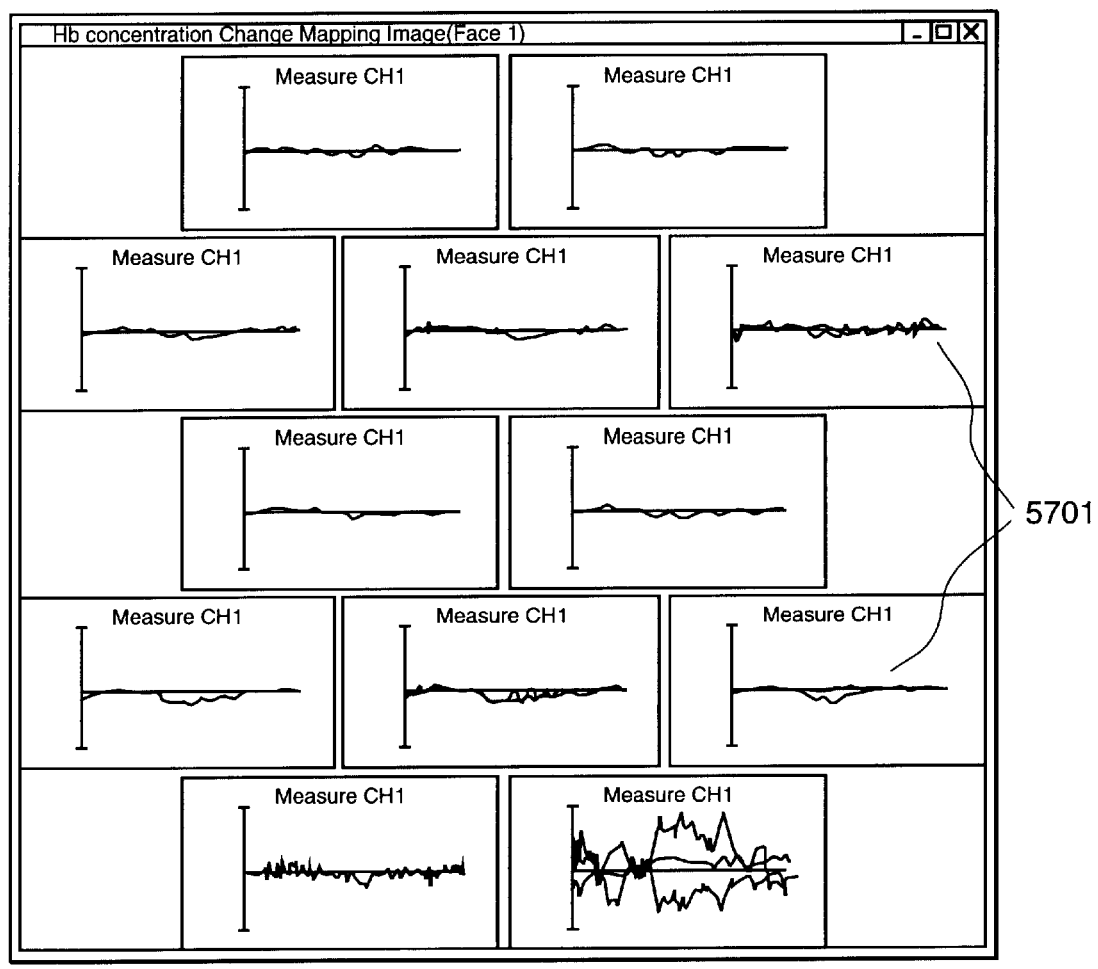
FIG. 57 is a window showing a map of the hemoglobin concentration graphs on the display unit.

If necessary, it is possible to set so that both windows of FIG. 33 and FIG. 57 may be on a single window.

After measurement and data analysis are completed, go back to the initial window (Main Menu window) of FIG. 2 and click the Analyze button 202. The Main Menu window is substituted by the Select Process window (see FIG. 16). The items and functions of the Select Process window (see FIG. 16) are already described above. When the Show Graph button 1602 is clicked on the Select Process window, the Show Graph Menu window (see FIG. 45) appears on-screen.

On the Show Graph Menu window (see FIG. 45), the Measurement Data button 4501 is used to load the measured data and the Analyzed Data button is used to load the analyzed data. Either of these buttons is clicked, the File Load window (see FIG. 18) appears on screen. The "Analyzed Data include Topograph image" button 4503 is used to load analyzed data including topographic image data. When this button is clicked, the Load Topograph Image window (see FIG. 40) appears on-screen. The Close button 4504 is to close the Show Graph Menu window. When this button is clicked, the Select Process window (see FIG. 16) returns. The File Type box 1808 on the window of FIG. 18 or the OK button 4003 on the Load Topograph Image window of FIG. 40 is clicked, the select Graph window (see FIG. 46) appears on-screen.

Figure 47:
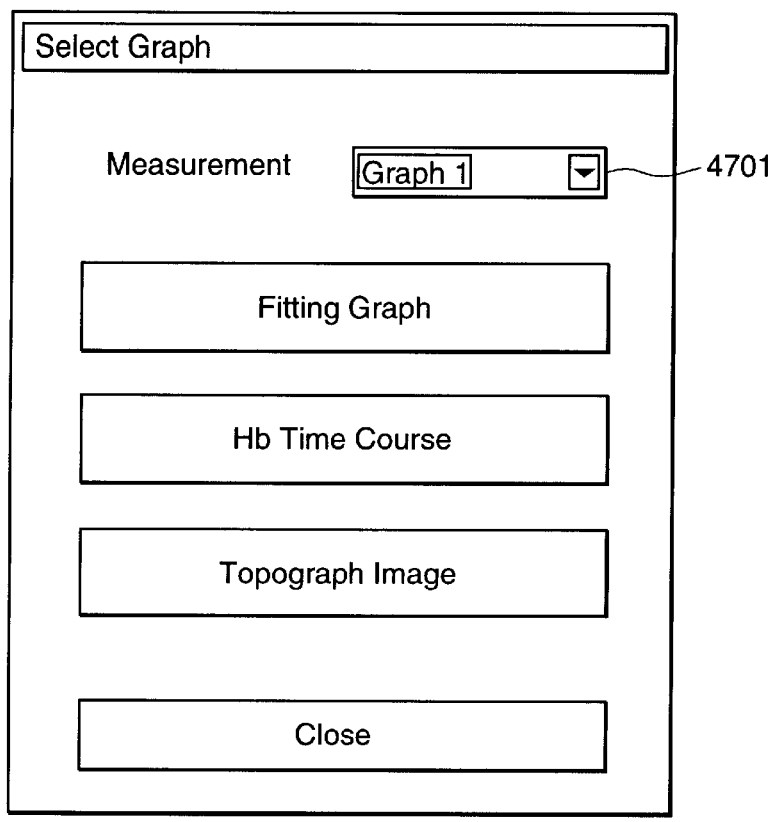
FIG. 47 is a Select Graph window for selecting a graph displayed on the display unit.
Figure 48:
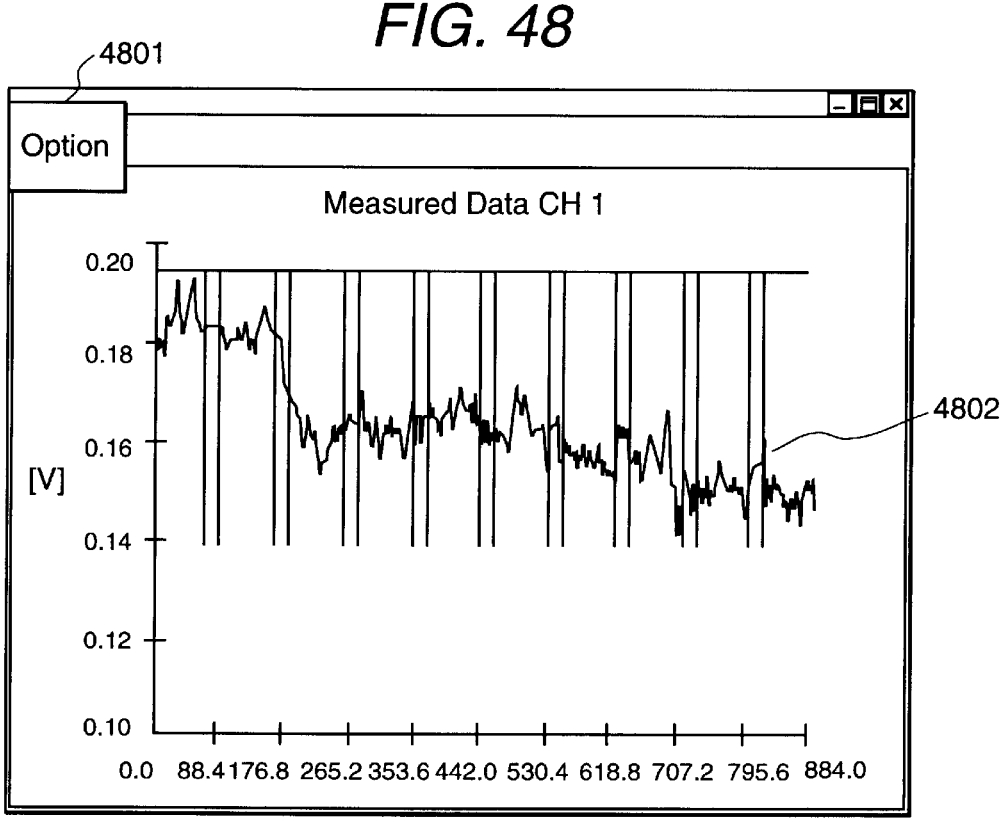
FIG. 48 is a window showing a graph of measured data on the display unit.

The window of FIG. 46 has the following items and functions:

4601: This Measurement Graph button 4601 is used to display a graph of measured time-series data. It is possible to simultaneously display graphs of data measured on a plurality of A/D converter channels. When this button is clicked, the graph display control window appears. After the setting on this window is completed, the Measured Data window (see FIG. 48) appears on-screen. The area 4802 on this window shows a measurement graph. After the Measurement Graph button is clicked, the Select Graph window of FIG. 46 turns as shown in FIG. 47.

4602: This Fitting Graph button 4602 is used to display a graph of a fitting curve (baseline) and measured data (called a fitting graph). When this button is clicked, the Fitting Graph Parameter window (see FIG. 49) appears on-screen.

4603: This Hb Time Course button is used to display a graph of a time-series data of the concentration of hemoglobin.

When this button is clicked, the Hb Time Course Parameter window (see FIG. 54) appears on-screen.

4604: This Topograph Image button is used to display a topographic image. When this button is clicked, the Topograph window for edition and display of a topographic image.

4605: This Close button is used to end graphic display. When this button is clicked, the Show Graph Menu window (see FIG. 45) appears on-screen.

The button 4701 of the Select Graph window (see FIG. 47) is used to select a number of a graph of data measured on a plurality of A/D converter channels. Available graph numbers are Graph1 to Graphn (where "n" is a maximum A/D converter channel number).

Figure 49:
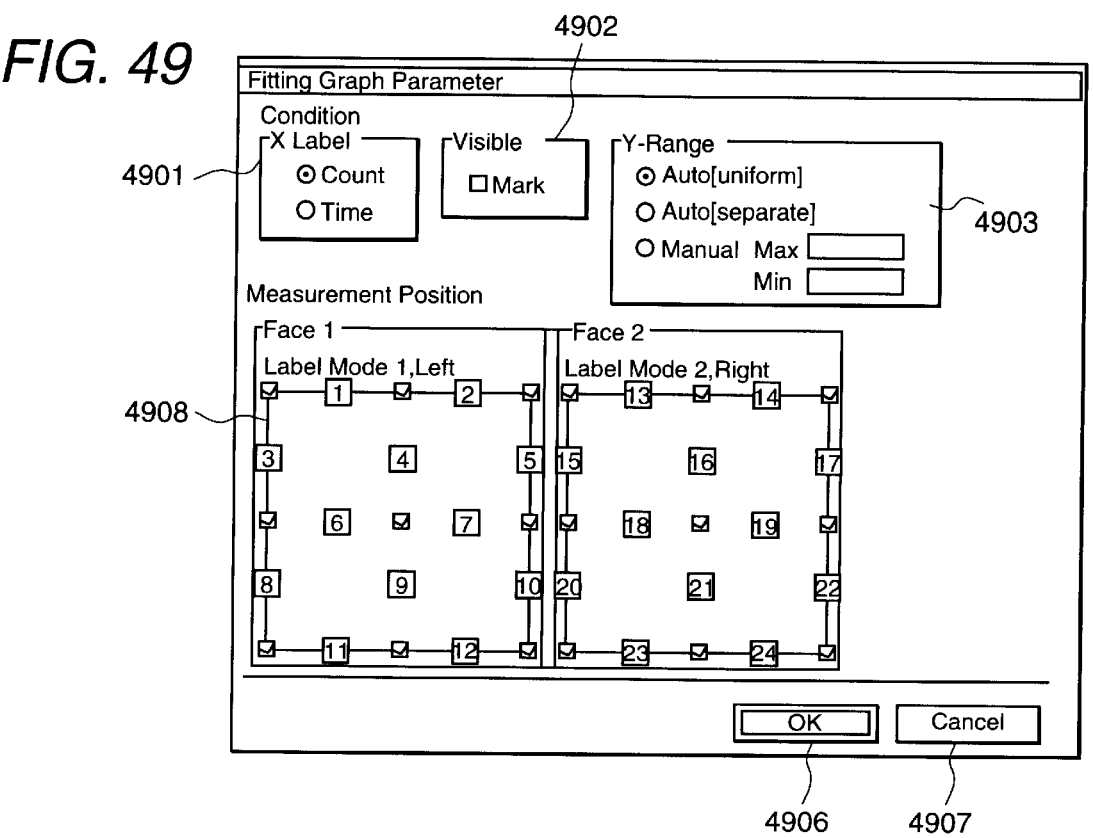
FIG. 49 is a window for setting a condition of displaying a fitting graph on the display unit.

The window of FIG. 49 is displayed when the Fitting Graph button 4602 is clicked and has the following items and functions:

4901: This field is used to select a label of the X axis (Time or Sampling count).

4902: This field is used to make marks visible or invisible.

4903: This field is used to specify a range of the Y axis.

Auto (uniform): Automatically assigns optimum maximum and minimum values so that all graphs may have the same maximum value and the same minimum value.

Auto (separate): Automatically assigns maximum and minimum values so that each graph may have its own optimum maximum and minimum values.

Manual: Allows the operator to manually assign maximum and minimum Y-axis values to each graph.

4906: This button is used to end the setting. When this button is clicked, the Fitting Graph window (see FIG. 50) appears on-screen.

4907: This button is used to cancel the setting on this window. When this button is clicked, the Fitting Graph window (see FIG. 50) appears on-screen.

4908: This field shows the positions of measuring channels. A measuring channel number appears on a measuring position having measuring position data.

When the mouse cursor is positioned on a measuring channel number, an A/D converter channel number corresponding to the measuring channel appears under the mouse cursor.

Figure 50:
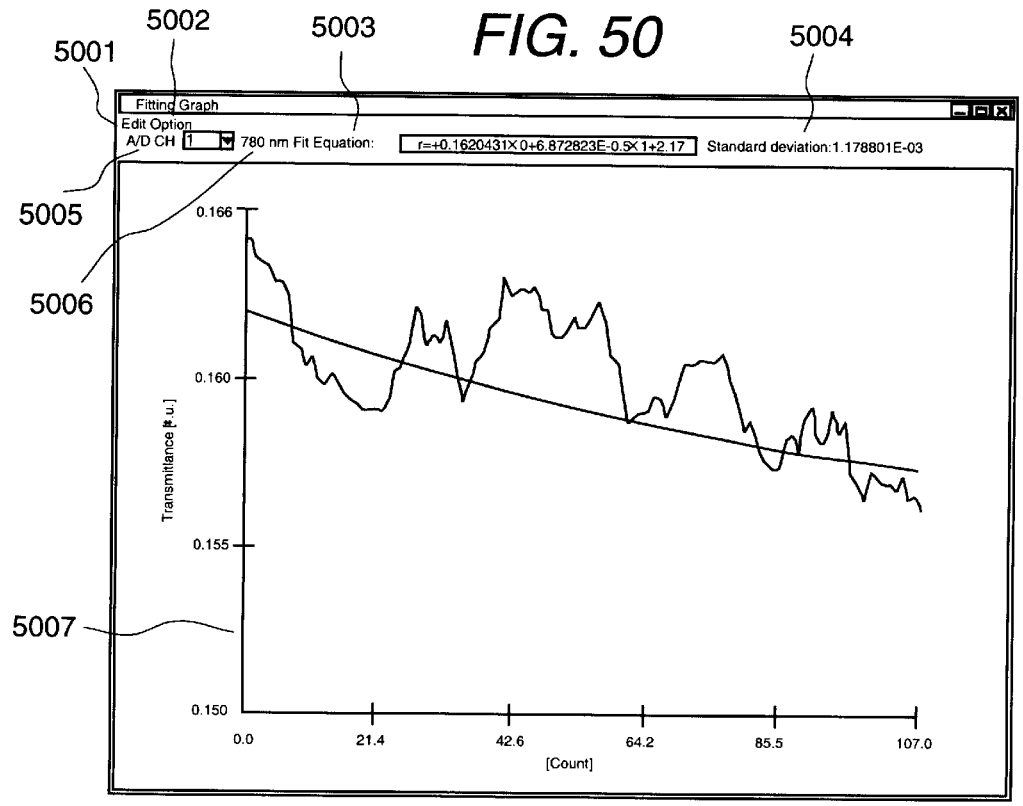
FIG. 50 is a window showing a fitting graph on the display unit.

As already explained, when the OK button 4906 or the Cancel button 4907 is clicked on the Fitting Graph Parameter window (see FIG. 49), the Fitting Graph window of FIG. 50 appears on-screen. The Fitting Graph window has the following items and functions.

5001: A button to call the Edit pop-up menu (see FIG. 51)

5002: A button to call the Option pop-up menu (see FIG. 52)

5003: An area for displaying a fitting curve equation

5004: An area for displaying a standard square-law deviation of the fitting curve

5005: An area used to display or select an A/D converter channel number which measured data on the graph When the A/D converter channel number in this area is changed, the graph is updated.

5006: An area for displaying the wavelength of the measuring light

Figure 51:
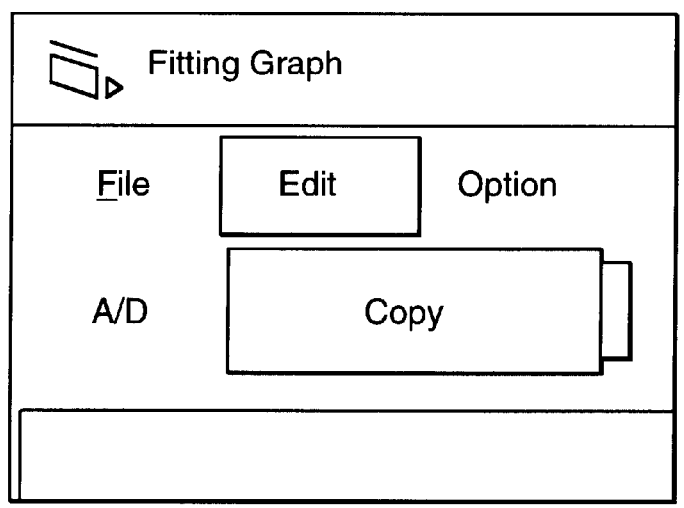
FIG. 51 is an Edit menu window displayed on the display unit.

5007: An area for displaying a graph (baseline) of the measured data and a fitting curve FIG. 51 shows the Edit menu which pops up when the Edit button 5001 of the Fitting Graph window (FIG. 50) is chosen. When the "Copy" button is clicked on this pop-up menu, the fitting graph is copied to the clipboard (which is a storage area of the storage unit in the computer).

Figure 52:
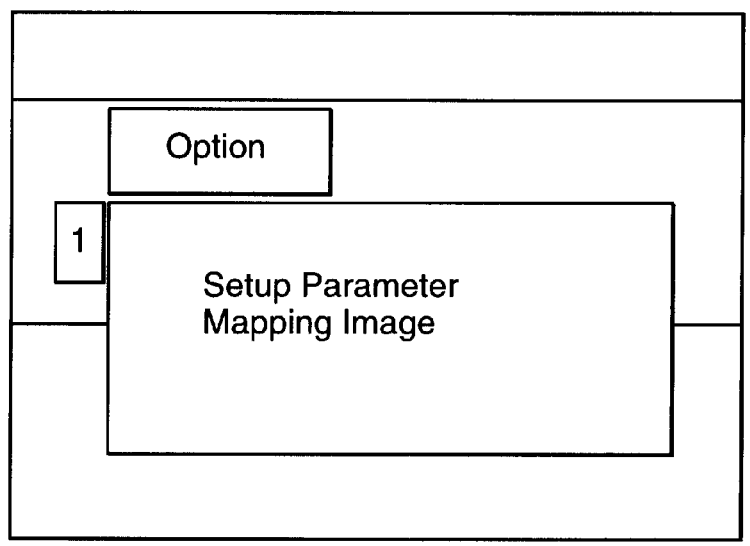
FIG. 52 is an Option menu window displayed on the display unit.

FIG. 52 shows the Option menu which pops up when the Option button 5002 of the Fitting Graph window (FIG. 50) is chosen. The Option menu has options "Setup Parameter," "Mapping Image," and "Condition." When "Setup Parameter" is chosen, the Fitting Graph Parameter window (see FIG. 49) appears on-screen. When "Mapping Image" is chosen, the Fitting Curve Mapping Image window(see FIG. 53) appears on-screen.

The area 5301 on the Fitting Curve Mapping Image window (see FIG. 53) shows fitting graphs of the A/D converter channels corresponding to measuring positions.

This example shows fitting graphs of the A/D converter channels corresponding to measuring positions. Different windows or colors are given to different wavelengths. Naturally, different line types can be given to different wavelengths.

When the Hb Time Course button 4603 (see FIG. 46) on the Select Graph window (see FIG. 46), the Hb Time Course Parameter window (see FIG. 54) appears on-screen. This window has the following items and functions:

5401: This field is used to select types of hemoglobin data and marks displayed in a graph. Select types and click their check boxes.

5402: A Condition/Position tab

5403: This field is used to specify a range of the Y axis

Auto (uniform): Automatically assigns optimum maximum and minimum values so that all graphs may have the same maximum value and the same minimum value.

Auto (separate): Automatically assigns maximum and minimum values so that each graph may have its own optimum maximum and minimum values.

Manual: Allows the operator to manually assign maximum and minimum Y-axis values to each graph.

5404: This field is used to select a label of the X axis (Time or Sampling count).

5405: Select a timewise averaging mode here.

Natural: No averaging is done when this option is selected.

Average: Averaging is done at every specified count on the X-axis when this option is selected Averaging Counts: A box to enter a count at which averaging is done Splitting count: A box to enter a count which is skipped and not included in averaging.

Moving average: A moving averaging is done when this option is selected.

Averaging counts: A box to enter the number of points for the moving average.

5406: Select whether statistic processing is required. Select "None" to create topographic images without statistic processing or "Mahalanobis" to create topographic images with statistic processing.

5407: When this Load Mode File button is clicked, the File Load window (see FIG. 18) appears on-screen. From this File Load window, the operator can load a measurement mode file to specify positions of measuring channels.

5409: Click this OK button to end the setting. When this button is clicked, the Change Concentration of Hb window (see FIG. 56) appears on-screen.

5410: This button is used to cancel the setting on this window. When this button is clicked, the Change Concentration of Hb window (see FIG. 56) appears on-screen.

5411: This area shows the positions of measuring channels.

Figure 54:
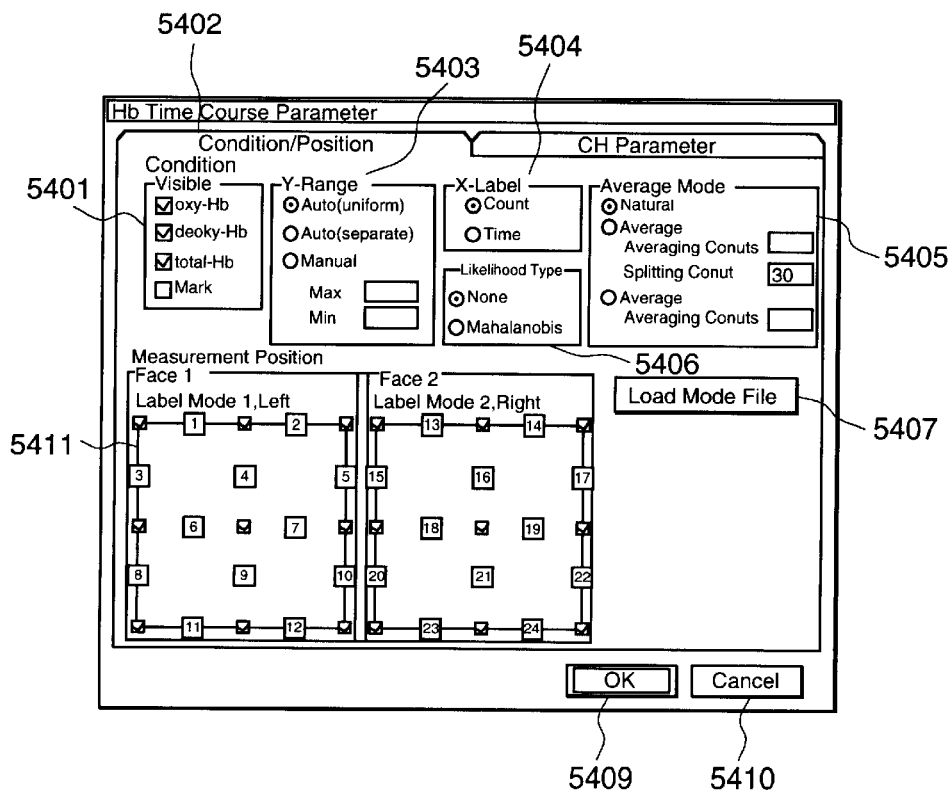
FIG. 54 is a Condition/Position tab window for setting conditions of displaying a hemoglobin graph.
Figure 55:
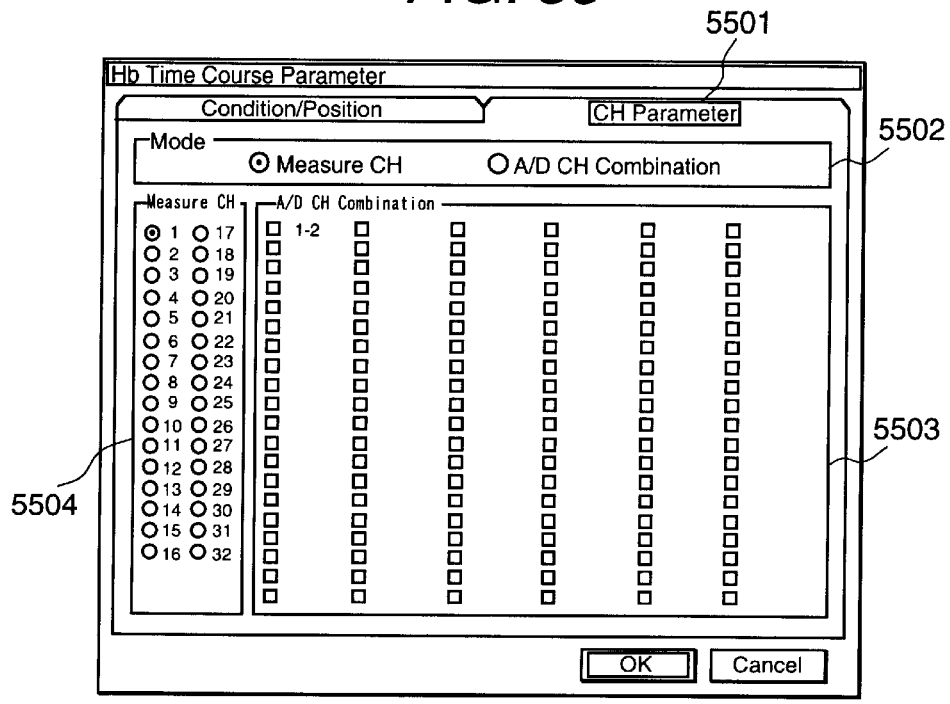
FIG. 55 is an OA/D CH Combination tab window for setting conditions of displaying a hemoglobin graph.
Figure 56:
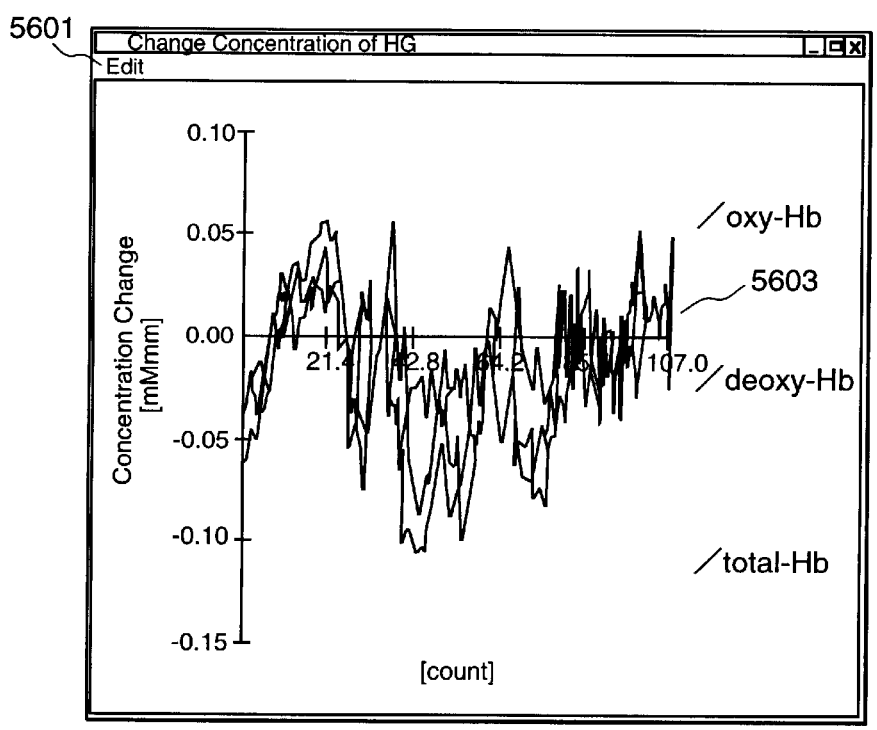
FIG. 56 is a window showing a hemoglobin concentration graph on the display unit.

When the mouse cursor is positioned on a measuring channel. The window of FIG. 56 has the following items and functions:

FIG. 55 shows another Hb Time Course Parameter window and has the following items and functions:

5501: This is a CH Parameter tab which is the same as that of FIG. 54. When the CH Parameter tab of the Hb Time Course Parameter window of FIG. 54 is clicked, the Hb Time Course Parameter window of FIG. 55 appears on-screen. When the Condition/Position tab of FIG. 55 is clicked, the Hb Time Course Parameter window of FIG. 54 appears on-screen.

5502: Click "Measure CH" to specify measuring channel numbers in the area 5504 and click "A/D CH Combination" to specify combinations of A/D converter channels in the area 5503.

5503: This area is used to specify a combination of two or more A/d converter channels to measure Hb concentrations f or each measuring channel which is specified in the area 5504.

5504: This is an area to specify measuring channels to be given to graphs.

As seen from the above, when the OK button 5409 or the Cancel button 5410 on the window of FIG. 54 is clicked, the Change Concentration of Hb (see FIG. 56) appears on-screen. The window of FIG. 56 has the following items and functions:

5601: A button to open the Edit pop-up menu (see FIG. 51)

5603: An area to display a Hb concentration change graph
On the window of FIG. 56, examples of data "/oxy-Hb," "/deoxy-Hb," and "/total-Hb" have different line colors and types (slanted parts).

When the operator double-clicks the top bar on any of the above-described windows, a Print command menu appears. Select a command to print.

With this, the detailed explanation of the embodiment of the present invention is completed. The features of the optical measuring apparatus will be summarized below. It is to be understood that the present invention is not intended to be limited to these features.

1) For display of a plurality of time-series graphs as the results of measurement and data analysis, measuring wavelengths and target data kinds are given different line colors or types (as shown in FIGS. 7, 11, 12, 48, 50, 53, 56, and 57).

1a) The optical measuring apparatus of the present invention comprises means of adding marks automatically or manually during measurement. The line color and type of the mark are different from those of the graph (as shown in FIGS. 5 and 7).

1aa) The mark positions (times values) entered in measurement can be added, deleted, and moved after measurement (as shown in FIG. 19).

Figure 53:
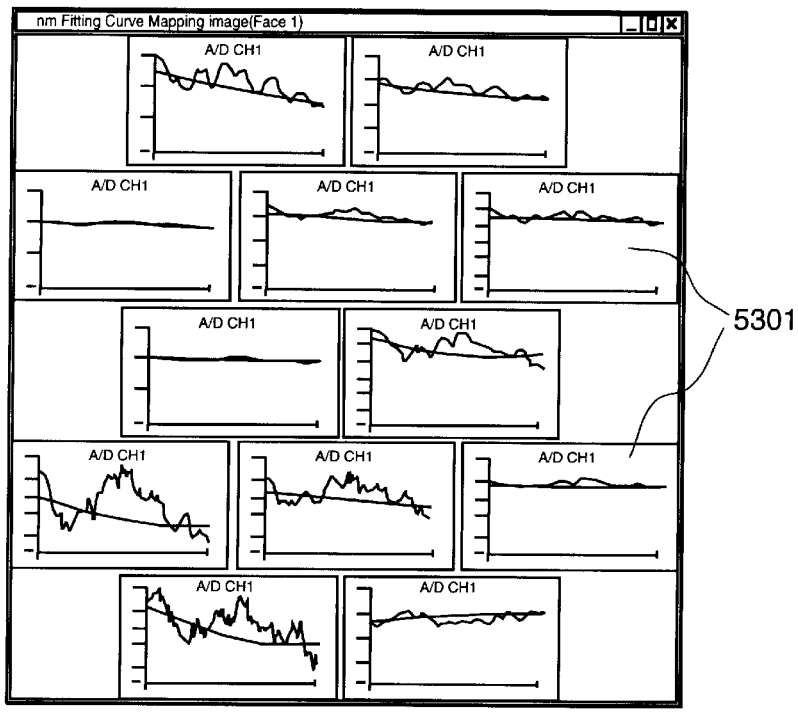
FIG. 53 is a window showing a map of the fitting graphs on the display unit.

1b) For display of a plurality of time-series graphs, the graphs are displayed at positions corresponding to the measuring positions from which signals are obtained (as shown in FIGS. 53, 57, and 62).

1c) For display of a plurality of time-series graphs, the system of the optical measuring apparatus of the present invention contains a window for specifying so that the graphs may have the same Y-axis values or that the graphs may have their own optimum Y-axis values (as shown in FIGS. 53, 54, and 57).

6) The system of the optical measuring apparatus of the present invention stores variables obtained in the preceding measurement and analysis and loads the stored variables for substitution and addition in the next measurement and analysis.

8) The system of the optical measuring apparatus of the present invention contains a window which displays a plurality of measuring positions and a plurality of light emitting and receiving positions for measurement and analysis of data (as shown in FIGS. 3, 33, and 62).

8a) The system of the optical measuring apparatus of the present invention has a function of using colors, symbols, or numeric characters to represent the status of each signal from each measuring or light emitting and receiving position on a window which displays a plurality of measuring positions and a plurality of light emitting and receiving positions (as shown in FIGS. 3, 33, and 62).

9) The system of the optical measuring apparatus of the present invention has a window of selecting to make a plurality of measuring, light-emitting, and light-receiving positions visible or invisible on a created image (as shown in FIGS. 33 and 39).

10) The system of the optical measuring apparatus of the present invention has a window of displaying moving images. The window comprises an area for displaying the time of a reproduced moving image and a rectangular area to display the whole image reproduction time. The rectangular area contains a line representing the corresponding time of the image (as shown in FIG. 34).

10a) The window for reproducing moving images contains a window for specifying Stop, Pause, Forward, Backward, and Repeat functions (as shown in FIG. 34).

10b) The window for reproducing moving images contains a window for displaying a plurality of images in synchronism (as shown in FIG. 39).

10c) The window for reproducing moving images contains a window for displaying a figure which represents a mark setting time specified during measurement in a rectangular area to display the whole image reproduction time (as shown in FIG. 34).

10ca) The window for reproducing moving images contains a window for changing the color of an area enclosed in marks when there are two or more figures each of which represents a mark setting time specified during measurement in a rectangular area to display the whole image reproduction time (as shown in FIG. 34).

10d) The system of the optical measuring apparatus of the present invention has a function of beeping when a line representing the time of the image on-screen in a rectangular area to display the whole image reproduction time crosses a mark on the moving image window (as shown in FIG. 34).

10e) The system of the optical measuring apparatus of the present invention contains a window having a function of changing the color of the background when a line representing the time of the image on-screen in a rectangular area to display the whole image reproduction time crosses a mark on the moving image window (as shown in FIG. 34).

11) The image displaying window has a window containing parts for setting a contrast range and a hue of the window (as shown in FIG. 34).

Figure 30:
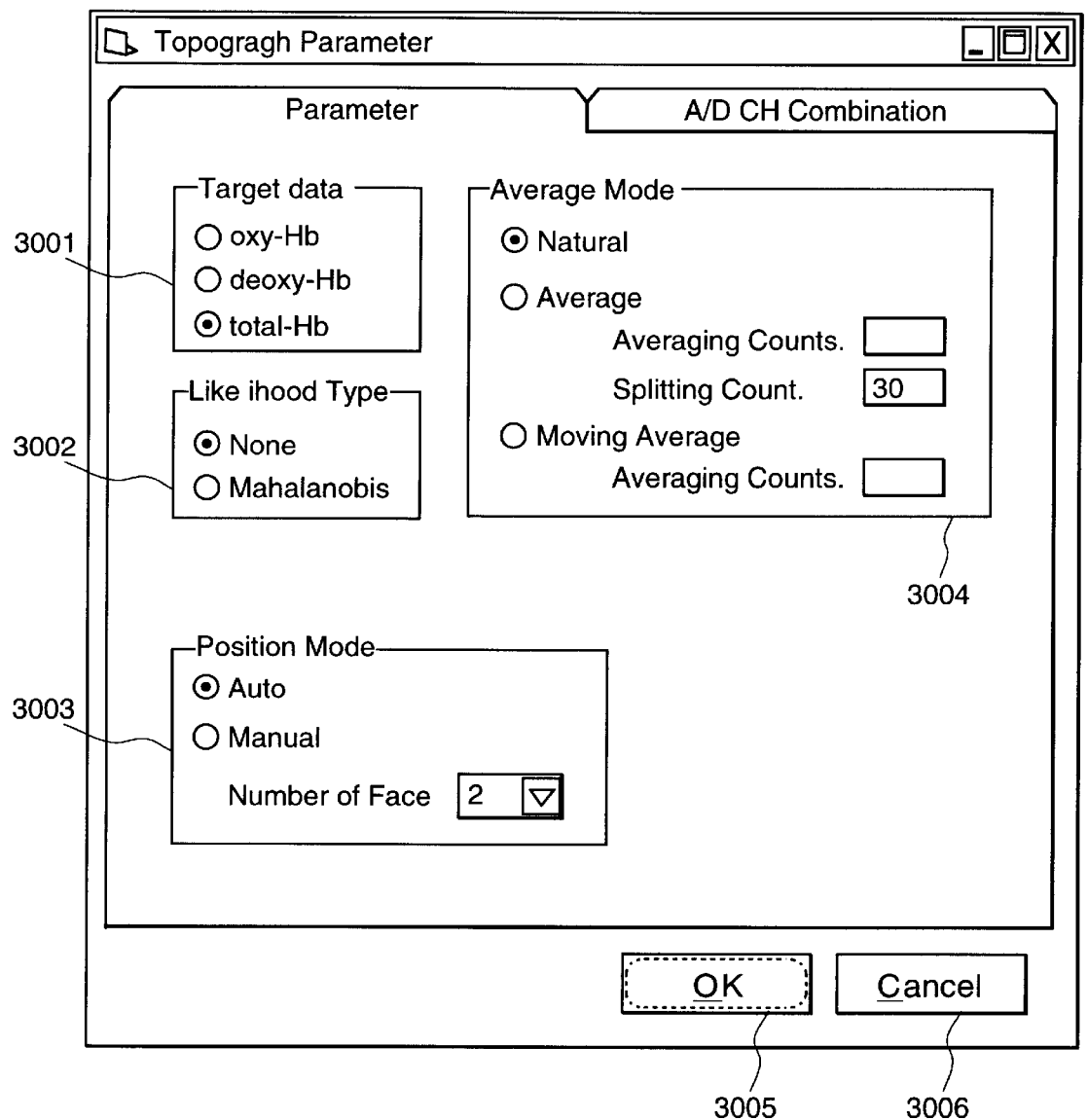
FIG. 30 is a dialog box for setting topograph parameters displayed on the display unit.
Figure 31:
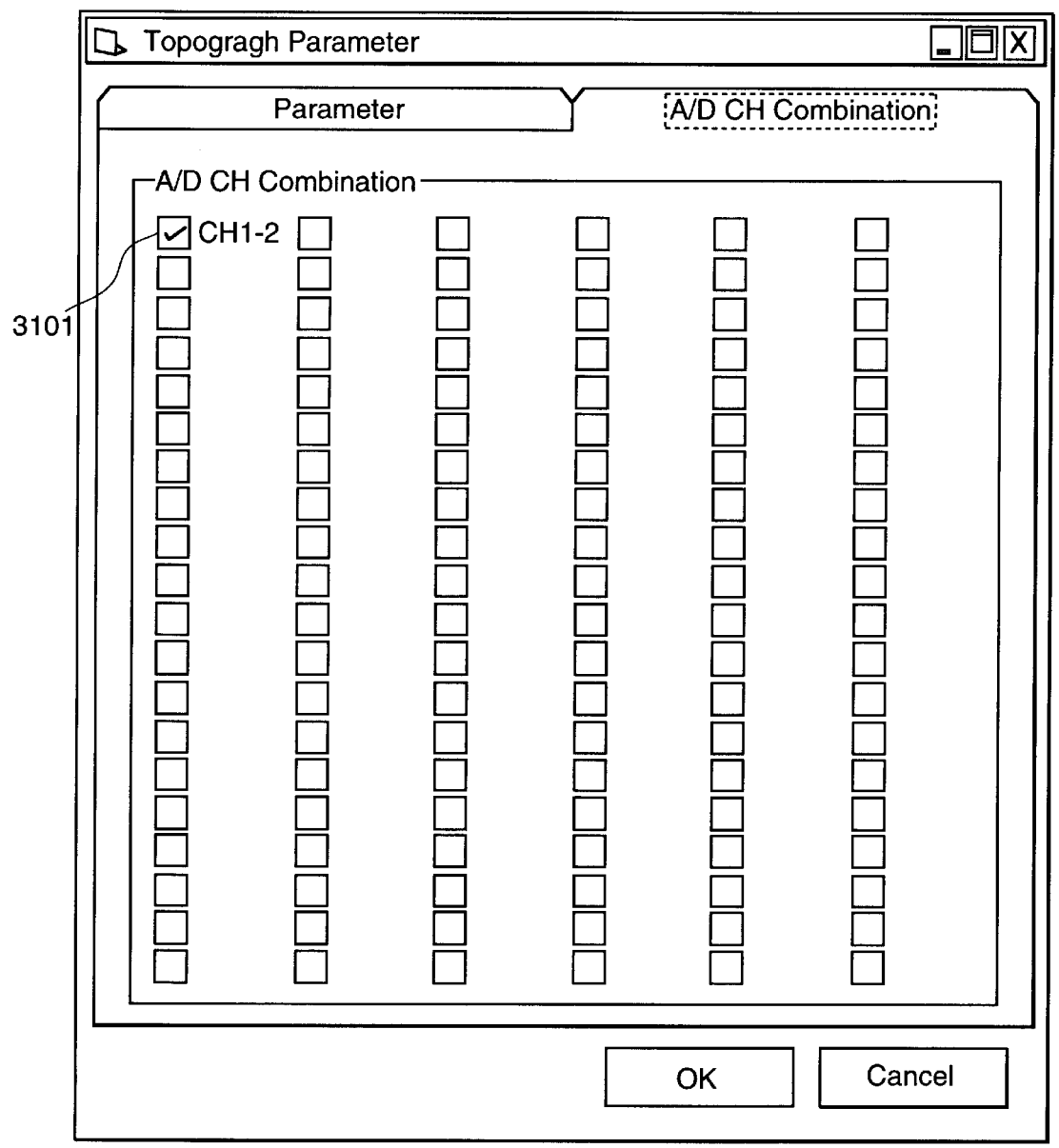
FIG. 31 is a dialog box for setting topograph parameters (A/D CH Combination) displayed on the display unit.

12) The system of the optical measuring apparatus of the present invention contains a window for setting an average at a preset time interval or a moving average of an arbitrary cardinal number at means to analyze signals (as shown in FIG. 30).

12a) The system of the optical measuring apparatus of the present invention has, as a signal analyzing means, a window of selecting a statistic analyzing method such as a "t" test which uses signal fluctuations as a variable (as shown in FIG. 30).

In accordance with the embodiment of the present invention, even a beginning operator can obtain reliable data by simple and quick operations.

FIELD OF THE INVENTION

The present invention provides an optical measuring apparatus fit for optically measuring a sample, easily processing, and displaying images of predetermined items according to information obtained by the measurement.

What we claim is:

1. An optical measuring apparatus having a measuring device for optically measuring density or variation of an in-vivo metabolic material of a sample, comprising:

a pair of a first irradiation part for applying a light beam on said sample and a first detection part provided corresponding to said first irradiation part so as to detect said light beam through said sample, wherein a first measuring position is obtained as substantially a mid point between said first irradiation part and said first detection part;

a pair of a second irradiation part for applying a light beam and a second detection part provided corresponding to said second irradiation part so as to detect said light beam through said sample, wherein a second measuring position is obtained as substantially a mid point between said second irradiation part and said second detection part;

a first display window for displaying representations of said first and second irradiation parts, said first and second detection parts and said first and second measuring positions corresponding to positions thereof on said sample; and a second display window for displaying respective time-series graphs of measurements of said in-vivo metabolic material of said sample corresponding to said first and second measuring positions displayed on said first display window.

2. An optical measuring apparatus as defined in claim 1, wherein said first and second irradiation parts, and said first and second detection parts are arranged on a substantially a rectangular lattice.

3. An optical measuring apparatus as defined in claim 2, wherein said first and second irradiation parts, and said first and second detection parts are arranged on a substantially a square lattice.

4. An optical measuring apparatus as defined in claim 1, wherein said sample is a head portion of a living body.

5. An optical measuring apparatus as defined in claim 1, comprising a means for selecting an averaging analysis mode or a non-added analysis mode.

6. An optical measuring apparatus as defined in claim 1, comprising a means for selecting an averaging analysis mode or a non-added analysis mode.

7. An optical measuring apparatus having a measuring device for optically measuring density or variation of an in-vivo metabolic material of a sample, comprising:

a plurality of irradiation parts for applying a light beam on said sample and a plurality of detection parts for detecting said light beam obtained through said sample being arranged in a lattice shape on said sample, said plurality of irradiation parts and said plurality of detection parts being constructed with a pair of a first irradiation part for applying a light beam on said sample and a first detection part provided corresponding to said first irradiation part, and a pair of a second irradiation part for applying a light beam and a second detection part provided corresponding to said second irradiation part, wherein a first measuring position is obtained as substantially a mid point between said first irradiation part and said first detection part, and a second measuring position is obtained as substantially a mid point between said second irradiation part and said second detection part;

a first display window for displaying representations of said first and second irradiation parts, said first and second detection parts and said first and second measuring positions corresponding to positions thereof on said sample; and a second display window for displaying respective time-series graphs of measurement of said in-vivo metabolic material of said sample corresponding to said first and second measuring positions displayed on said first display window.

8. An optical measuring apparatus as defined in claim 7, wherein said sample is a head portion of a living body.

9. An optical measuring apparatus having a measuring device for optically measuring density or variation of an in-vivo metabolic material of a sample, comprising:

a pair of a first irradiation part for applying a light beam on said sample and a first detection part provided corresponding to said first irradiation part so as to detect said light beam through said sample, wherein a first measuring position is obtained as substantially a mid point between said first irradiation part and said first detection part;

a pair of a second irradiation part for applying a light beam and a second detection part provided corresponding to said second irradiation part so as to detect said light beam through said sample, wherein a second measuring position is obtained as substantially a mid point between said second irradiation part and said second detection part;

a display window for displaying positions of said first and second irradiation parts, said first and second detection parts and said first and second measuring positions corresponding to positions thereof on said sample, or an optical topography image corresponding to said first and second measuring positions; and a switching means for selecting to display both of, or arbitrarily any one of, said positions and said optical topography image corresponding to said first and second measuring positions.

10. An optical measuring apparatus having a measuring device for optically measuring density or variation of an in-vivo metabolic material of a sample, and a display means for displaying an optical image based on said density or variation thereof, comprising a plurality of irradiation parts for applying a light beam on said sample and a plurality of detection parts for detecting said light beam through said sample being arranged in a lattice shape, wherein measuring positions obtained as substantially mid points between respective said irradiation parts and respective said detection parts are arranged in a lattice shape, and respective time-series graphs of measurement of said in-vivo metabolic material of said sample are displayed on said display means at display positions corresponding to said measuring positions.

\* \* \* \* \*